United States Patent
Mikkelsen et al.

(10) Patent No.: US 8,581,021 B2
(45) Date of Patent: Nov. 12, 2013

(54) PIG WHOSE GENOME COMPRISES A HETEROLOGOUS SITE-SPECIFIC RECOMBINATION SITE AND A TRANSPOHON TAG

(75) Inventors: Jacob Giehm Mikkelsen, Silkeborg (DK); Brian Moldt, San Diego, CA (US); Anders Lade Nielsen, Åbyhøj (DK); Lars Axel Bolund, Skødstrup (DK); Peter Michael Kragh, Trondheim (NO); Jannik Ejnar Jakobsen, Trige (DK); Arne Lund Jørgensen, Højbjerg (DK)

(73) Assignee: Aarhus Universitet (DK)

( * ) Notice: Subject to any disclaimer, the term of this patent is extended or adjusted under 35 U.S.C. 154(b) by 111 days.

(21) Appl. No.: 12/529,958

(22) PCT Filed: Mar. 7, 2008

(86) PCT No.: PCT/DK2008/050058
§ 371 (c)(1),
(2), (4) Date: Jan. 7, 2010

(87) PCT Pub. No.: WO2008/106985
PCT Pub. Date: Sep. 12, 2008

(65) Prior Publication Data
US 2010/0154069 A1 Jun. 17, 2010

(30) Foreign Application Priority Data

| Mar. 7, 2007 | (DK) | 2007 00349 |
| May 1, 2007 | (DK) | 2007 00659 |
| Jul. 13, 2007 | (DK) | 2007 01039 |

(51) Int. Cl.
*A01K 67/00* (2006.01)
*C12N 15/00* (2006.01)

(52) U.S. Cl.
USPC .................... 800/17; 800/25; 435/455

(58) Field of Classification Search
None
See application file for complete search history.

(56) References Cited

FOREIGN PATENT DOCUMENTS

| WO | WO 2004/111252 | 12/2004 |
| WO | WO 2007/002372 | 1/2007 |

OTHER PUBLICATIONS

Huang et al. Stable gene transfer and expression in human primary T cells by the Sleeping Beauty transposon system. Blood, 2006, vol. 107, 483-491.*
Lai et al. Production of a-1,3-Galactosyltransferase Knockout Pigs by Nuclear Transfer Cloning Science, 2002, vol. 295, pp. 1089-1092.*
Merrihew et al. Efficient Modification of the APRT Gene by FLP/FRT Site-Specific Targeting. Somatic Cell and Molecular Genetics, 1999, vol. 21, pp. 299-307.*
Booth et al. (2001), Simplification of Bovine Somatic Cell Nuclear Transfer by Application of a Zona-Free Manipulation Technique, Cloning and Stem Cells, vol. 3, No. 3, p. 139-150.
Branda CS et al. (Jan. 2004), "Talking about a revolution: The impact of site-specific recombinases on genetic analyses in mice.", Dev Cell, 6, 7-28.
Broach JR et al. (1980), "Replication and recombination functions associated with the yeast plasmid, 2µ circle.", Cell, 21, 501-508.
Buchholz R et al. (Jul. 1998), "Improved properties of FLP recombinase evolved by cycling mutagenesis.", Nat Biotechnol, 16, 657-662.
Chen ZY et al. (Jan. 2005), "Improved production and purification of minicircle DNA Vector free of plasmid bacterial sequences and capable of persistent transgene expression in vivo.", Hum Gene Ther, 16 (1), 126-131.
Chen ZY et al. (Sep. 2003), "Minicircle DNA vectors devoid of bacterial DNA result in persistent and high-level transgene expression in vivo.", Mol Ther, 8 (3), 495-500.
Chung JH et al. (Aug. 13, 1993), "A 5' element of the chicken β-globin domain serves as an insulator in human erythroid cells and protects against position effect in drosophila.", Cell, 74, 505-514.
Clark et al. (2007), Enzymatic engineering of the procine genome with transposons and recombinases, BMC Biotechnology, vol. 7, No. 42, p. 42.
Clark K et al. (Oct. 2007), Transposons and recombinases for engineering the pig genome, Transgenic Research, vol. 16, p. 840.
Clark Karl J et al.(2007), Pigs takling wing transposons and recombinases, Genome Biology, vol. 8 Suppl. 1, Article S13.
Collier LS et al. (Jul. 2005), "Cancer gene discovery in solid tumors using transposon-based somatic mutagenesis in the mouse.", Nature, 436 (7048), 272-276.
Craig NL (2002), Transposases and Integrases, Enclyclopedia of Life Sciences, pp. 1-7.
Dobrinsky et al. (1996), Development of a Culture Medium (BECM-3) for Porcine Embryos: Effect of Bovine Serum Albumin and Fetal Bovine Serum on Embryo Development, Biol Reprod, vol. 55, p. 1069-1074.
Dorer DR et al. (Jul. 1, 1994), "Expansions of transgene repeats cause heterochromatin formation and gene silencing in drosophilia.", Cell, 77 (7), 993-1002.
Du et al. (2005), High overall In Vitro Efficiency of Porcine Handmade Cloning (HMC) Combining Partial Zona Digestion and Oocyte Trisection with Sequential Culture, Cloning and Stem Cells, vol. 7, No. 3, p. 199-204.

(Continued)

*Primary Examiner* — Deborah Crouch
(74) *Attorney, Agent, or Firm* — McLane, Graf, Raulerson & Middleton, PA

(57) ABSTRACT

The present invention relates to a genetically modified pig comprising at least one site for integration of at least one transgene. The invention also pertains to a porcine embryo, blastocyst, fetus, donor cell and/or cell nucleus, derived from said genetically modified pig. In another aspect, the invention relates to any genetically modified porcine blastocyst, wherein the genetically modified genome comprises at least one site for integration of at least one transgene.

14 Claims, 28 Drawing Sheets

(56) References Cited

OTHER PUBLICATIONS

Du et al. (Oct. 4, 2007), Piglets born from handmade cloning, an innovative cloning method without micromanipulation, Theriogenology, vol. 68, No. 8, p. 1104-1110.
Dupuy AJ et al. (Apr. 2, 2002), "Mammalian germ-line transgenesis by transposition.", Proc nat acad sci USA, 99 (7), 4495-4499.
Dupuy AJ et al. (Jul. 14, 2005), "Mammalian mutagenesis using a highly mobile somatic sleeping beauty transposon system.", Nature, 436 (7048), 221-226.
Esaki et al. (2004), Cryopreservation of Porcine Embryos Derived from In Vitro-Matured Oocytes, Biology of Reproduction, vol. 71, p. 432-437.
Feltrin C et al. (2006), "Invitro bovine embryo development after nuclear transfer by handmade cloning using a modified wow culture system.", Reprod Fertil Dev, 18, 126.
Fischer SE et al. (Jun. 5, 2001), "Regulated transposition of a fish transposon in the mouse germ line.", Proc nat acad sci USA, 98 (12), 6759-6764.
Garcia-Otin L et al. (2006), "Mammalian genome targeting using site-specific recombinases.", Front Biosci, 11, 1108-1136.
Garrick D et al. (Jan. 18, 1998), "Repeat-induced gene silencing in mammals", Nature Genetics, 18 (1), 56-59.
Geurts AM et al. (May 22, 2006), "Structure-based prediction of insertion-site preferences of transposons into chromosomes,", Nucleic Acids Res, 34 (9), 2803-2811.
Geurts et al. (Jun. 2006), Conditional gene expression in the mouse using a Sleeping Beauty gene-trap transposon, BMC Biotechnology, vol. 6, No. 30.
Geurts et al. (Sep. 2006), Gene mutations and genomic rearrangements in the mouse as a result of transposon mobilization from chromosomal concatemers, PLOS Genetics, vol. 2, No. 9, p. 1413-1423.
Henikoff S (1998), "Conspiracy of silence among repeated transgenes.", Bioessays, 20 (7), 532-535.
Horie K et al. (Jul. 31, 2001), "Efficient chromosomal transposition of a Tc1/mariner-like transposon Sleeping Beauty in mice.", Proc Nat Acad Sci USA, 98 (16), 9191-9196.
Hoshino et al. (2005), Developmental Competence of Somatic Cell Nuclear Transfer Embryos Reconstructed from Oocytes Matured In Vitro with Follicle Shells in Miniature Pig, Cloning and Stem Cells, vol. 7, No. 1, p. 17-27.
Ivics et al. (Nov. 1997),Molecular Reconstruction of Sleeping Beauty, a Tc1-like Transposon from Fish, and Its Transposition in Human Cells, Cell, vol. 91, p. 501-510.
Ivics Z et al. (Jun. 2007), "Targeted Sleeping Beauty, transposon in human cells.", Mol Ther, 15 (6), 1137-1144.
Izsvak Z et al. (2000), "Sleeping Beauty, a wide host-range transposon vector for genetic transformation in vertebrates.", J Mol Biol, 302 (1), 93-102.
Kikuchi et al. (1999), Developmental Competence, after Transfer to Recipients, of Porcine Oocytes Matured, Fertilized, and Cultured In Vitro, Biology of Reproduction, vol. 60, P. 336-340.
Kikuchi et al. (2002), Successful Piglet Production after Transfer of Blastocysts Produced by a Modified In Vitro System, Biology of Reproduction, vol. 66, p. 1033-1041.
Kragh et al. (2004), Production of transgenic porchine blastocysts by hand-made cloning, Reprod. Fert. Dev. 16. p. 315-318.
Kragh et al. (2005), Efficient in vitro production of porcine blastocysts by handmade cloning with a combined electrical and chemical activation, Theriogenology 64, p. 1536-1545.
Kwan et al. (Nov. 1, 2007), The Tol2kit: a Multisite Gateway-Based Construction Kit for Tol2 Transposon Transgenesis Constructs, Developmental Dynamics, vol. 236, No. 11, p. 3088-3099.
Landy A (1993), "Mechanictic and Structural complexity in the site-specific recombination pathways of int and FLP.", Curr Opin Genet Dev, 3 (5), 699-707.
Largaespada David A (Nov. 7, 2003), Generating and manipulatin transgenic animals using transposable elements, Reproductive Biology and Endocrinology, vol. 1, No. 1.

Luo G et al. (Sep. 1998), "Chromosomal transposition of a Tc1/mariner-like element in mouse embryonic stem cells.", Proc Nat Acad Sci USA, 95 (18), 10769-10773.
Manuelidis L (Feb. 1991), "Heterochromatic features of an 11-megabase transgene in brain cells.", Prec Natl Acad Sci USA, 88 (3), 1049-1053.
Mikkelsen JG et al. (Oct. 2003), "Helper-independent Sleeping Beauty transposon-transposase vectors for efficient nonviral gene delivery and persistent gene expression in vivo.", Mol Ther, 8 (4), 654-665.
Moldt B et al. (Aug. 9, 2008), "Genomic insertion of lentiviral DNA circles directed by the yeast Flp recombinase.", BMC Biotechnology, 8, 60-70.
Needleman SB et al. (1970), A General Method Applicable to the Search for Similarities in the Amino Acid Sequence of Two Proteins, J. Mol. Biol. 48, p. 443-453.
Oback et al. (2003), Cloned Cattle Derived from a Novel Zona-Free Embryo Reconstruction System, Cloning and Stem Cells, vol. 5, No. 1, p. 3-12.
O'Gorman S et al. (1991), "Recombinase-mediated gene activation and site-specific integration in mammalian cells.", Science, 251 (4999), 1351-5.
Onishi A et al. (Aug. 18, 2000), "Pig cloning by microinjection of fetal fibroblast nuclei.", Science, 289 (5482), 1118-1190.
Peura et al. (1998), The Effect of Recipient Oocyte Volume on Nuclear Transfer in Cattle, Molecular Reproduction and Development, vol. 50, p. 185-191.
Peura et al. (2003), A Comparison of Established and New Approaches in Ovine and Bovine Nuclear Transfer, Cloning and Stem Cells, vol. 5, No. 4, . 257-277.
Polejaeva IA et al. (Sep. 7, 2000), "Cloned pigs produced by nuclear transfer from adult somatic cells.", Nature, 407 (6800), 86-90.
Reed et al. (Jan. 1992), In Vitro Culture of Pig Embryos, Theriogeneology, vol. 37, No. 1, p. 95-109.
Riu E et al. (Jul. 2007), "Histone modifications are associated with the persistence or silencing of vector-mediated transgene expression in vivo.", 15 (7), 1348-1355.
Robertson G et al. (1996), "Age-dependent silencing of globine transgenes in the mouse.", Nucleic Acids Res, 24 (8), 1465-1471.
Sarkar et al. (Jun. 2006), Insulated piggyBag vectors for insect trangenesis, BMC Biotechnology, vol. 6 No. 27.
Sauer B (1994), "Site specific recombination: developments and applications.", Curr Opin Biotech, 5, 521-527.
Schröder AR et al. (Aug. 2002), "HIV-1 integration in the human genome favors active genes and local hotspots.", Cell, 110 (4), 521-529.
Sherrer et al. (2004), Fertilization and blastocyst development in oocytes obtained from prepubertal and adult pigs, J Anim Sci, vol. 82, p. 102-108.
Smith et al. (1981), Comparison of Biosequences, Advances in Applied Mathematics 2, p. 482-489.
Sorrell et al. (Nov. 1, 2005), Targeted modification of mammalian genomes, Biotechology Advances vol. 23, No. 7-8, p. 431-469.
Thyagarajan B et al. (Jun. 2001), "Site-specific genomic integration in mammalian cells mediated by phage fC31 integrase.", 21 (12), 3926-3934.
Vajta et al. (1997), Survival and development of bovine blastocysts produced in vitro after assisted hatching, vitrification and in-straw direct rehydration, Journal of Reproduction and Fertility, vol. 111, p. 65-70.
Vajta et al. (2004), Production of a healthy calf by somatic cell nuclear transfer without micromanipulators and carbon dioxide incubators using the Handmade Cloning (HMC) and the Submarine Incubation System (SIS), Theriogenology, vol. 62, p. 1465-1472.
Vajta et al. (Jan. 29, 2007), Somatic cell nuclear transfer in pigs: recent achivements and future possibilities, Reproduction, Fertility, and Delevopment, vol. 19, No. 2, p. 403-423.
Vajta et. al (2003), Handmade Somatic Cell Cloning Cattle: Analysis of Factors Contributing to High Efficiency In Vitro, Biology of Reproduction, vol. 68, p. 571-578.
Vajta G. (2004), Oocyte and Embryo Vitrification, Annual ESDAR Conference 1999, p. 45-48.

(56) References Cited

OTHER PUBLICATIONS

Vigdal TJ et al. (2002), "Common physical properties of DNA affecting target site selection of Sleeping Beauty and other Tc1/ mariner transposable elements.", J Mol Biol, 323, 441-452.
Wilber A et al. (2007) "Efficient and stable transgene expression in human embryonic stem cells using transposon-mediated gene transfer.", Stem Cells, 25 (11), 2919-2927.
Wilson MH et al. (Jan. 2007), "PiggyBac transoson-mediated gene transfer in human cells.", Mol Ther, 15 (1), 139-145.
Wirth et al. (Jan. 1, 2004), Flp-Mediated Integration of Expression Methods Cassettes into FRT-Tagged Chromosomal Loci in Mammalian Cells, Molecular Biology vol. 267, p. 467-476.
Wu et al. (2004), Birth of Piglets by in vitro fertilization of zona-free porcine oocytes, Theriogenology, vol. 62, p. 1544-1556.
Wu X et al. (Jun. 2003), "Transcription start regions in the human genome are favored targets for MLV integration.", Science, 300 (5626), 1749-1751.
Yanez-Munoz RJ et al. (Mar. 2006), "Effective gene therapy with nonintegrating lentiviral vectors.", Nat Med, 12, 348-353.
Yant et al. (2004), Mutational Analysis of the N-Terminal DNA-Binding Domain of Sleeping Beauty Transposase: Critical Residues for DNA Binding and Hyperactivity in Mammalian Cells, Mol. Cell. Biol., vol. 24, No. 20, p. 9239-9247.
Yant et al. (May 2000), Somatic integration and long-term transgene expression in normal and haemophilic mice using a DNA transposon system, Nature Genetics, vol. 24, p. 35-41.
Yant SR et al. (Mar. 2005), "High-resolution genome-wide mapping of transposon integration in mammals.", Mol Cell Biol, 25 (6), 2085-2094.
Yant SR et al. (Mar. 2007), "Site-directed transposon integration in human cells.", Nucleic Acids Res, 35 (7), e50.
Yoshioka et al. (2002), Birth of Piglets Derived from Porcine Zygotes Cultured in a Chemically Defined Medium, Biology of Reproduction, vol. 66, p. 112-119.
Yusufzai TM et al. (Jun. 2004), "The 5'-HS4 chicken β-globin insulator is a CTCF-dependent nuclear matrix-associated element.", Proc Natl Acad Sci USA, 101 (23), 8620-8624.

\* cited by examiner

Transposition into minipig cells using a
short PGK- puromycin transposon

Transposition into minipig cells using
the presented transposon

A colony of green fluorescent minipig cells, containing the presented transposon. The cells were selected with puromycin for 10 days A green fluorescent blastocyst made from minipig cells containing the presented transposon

A

B

SEQUENCE LISTING

```
<160> NUMBER OF SEQ ID NOS: 21

<210> SEQ ID NO 1
<211> LENGTH: 48
<212> TYPE: DNA
<213> ORGANISM: Artificial
<220> FEATURE:
<223> OTHER INFORMATION: FRT site

<400> SEQUENCE: 1
gaagttacta ttccgaagtt cctattctct agaaagtata ggaacttc                48

<210> SEQ ID NO 2
<211> LENGTH: 200
<212> TYPE: DNA
<213> ORGANISM: Artificial
<220> FEATURE:
<223> OTHER INFORMATION: Wt loxP

<400> SEQUENCE: 2
ggaaagtccc caggctcccc aggcaggcag aagtatgcaa agcatcgagg atgtacgggc    60
```

| | |
|---|---|
| cagatatacg cgataacttc gtataatgta tgctatacga agttatacgc gtgaggtttt | 120 |
| caccgtcatc accgaaacgc gcgaggcagc tgtggaatgt gtgtcagtta gggtgtggaa | 180 |
| agtccccagg ctccccagca | 200 |

```
<210> SEQ ID NO 3
<211> LENGTH: 34
<212> TYPE: DNA
<213> ORGANISM: Artificial
<220> FEATURE:
<223> OTHER INFORMATION: Wt loxP core

<400> SEQUENCE: 3
```

| | |
|---|---|
| ataacttcgt ataatgtatg ctatacgaag ttat | 34 |

```
<210> SEQ ID NO 4
<211> LENGTH: 200
<212> TYPE: DNA
<213> ORGANISM: Artificial
<220> FEATURE:
<223> OTHER INFORMATION: LoxP257

<400> SEQUENCE: 4
```

| | |
|---|---|
| ttctattctg gggggtgggg tgggcagga cagcaagggg gaggattggg aagacaatag | 60 |
| caggcatgct gggatgcgg tgggctctat ggaaccagct ggggcgcgcc attaacttcg | 120 |
| tataaagtct cctatacgaa gttatattct agttgtggtt tgtccaaact catcaatgta | 180 |
| tcttatcatg tctggatccc | 200 |

```
<210> SEQ ID NO 5
<211> LENGTH: 38
<212> TYPE: DNA
<213> ORGANISM: Artificial
<220> FEATURE:
<223> OTHER INFORMATION: LoxP 257 core

<400> SEQUENCE: 5
```

| | |
|---|---|
| attaacttcg tataaagtct cctatacgaa gttatatt | 38 |

```
<210> SEQ ID NO 6
<211> LENGTH: 293
<212> TYPE: DNA
<213> ORGANISM: Artificial
<220> FEATURE:
<223> OTHER INFORMATION: attB full length

<400> SEQUENCE: 6
```

| | |
|---|---|
| gtcgacatgc cgccgtgac cgtcgagaac ccgctgacgc tgccccgcgt atccgcaccc | 60 |
| gccgacgccg tcgcacgtcc cgtgctcacc gtgaccaccg cgcccagcgg tttcgagggc | 120 |
| gagggcttcc cggtgcgccg cgcgttcgcc gggatcaact accgccacct cgacccgttc | 180 |
| atcatgatgg accagatggg tgaggtggag tacgcgcccg gggagcccaa gggcacgccc | 240 |
| tggcacccgc accgcggctt cgagaccgtg acctacatcg tcgacggtac ctg | 293 |

```
<210> SEQ ID NO 7
<211> LENGTH: 34
<212> TYPE: DNA
<213> ORGANISM: Artificial
<220> FEATURE:
<223> OTHER INFORMATION: attB core

<400> SEQUENCE: 7
```

| | |
|---|---|
| gtgccagggc gtgcccttgg gctccccggg cgcg | 34 |

<210> SEQ ID NO 8
<211> LENGTH: 39
<212> TYPE: DNA
<213> ORGANISM: Artificial
<220> FEATURE:
<223> OTHER INFORMATION: AttP core

<400> SEQUENCE: 8
cccccaactg agagaactca aaggttaccc cagttgggg                          39

<210> SEQ ID NO 9
<211> LENGTH: 600
<212> TYPE: DNA
<213> ORGANISM: Artificial
<220> FEATURE:
<223> OTHER INFORMATION: Puromycin resistance gene

<400> SEQUENCE: 9
atgaccgagt acaagcccac ggtgcgcctc gccacccgcg acgacgtccc ccgggccgta    60
cgcaccctcg ccgccgcgtt cgccgactac cccgccacgc gccacaccgt cgatccggac   120
cgccacatcg agcgggtcac cgagctgcaa gaactcttcc tcacgcgcgt cgggctcgac   180
atcggcaagg tgtgggtcgc ggacgacggc gccgcggtgg cggtctggac cacgccggag   240
agcgtcgaag cggggggcgt gttcgccgag atcggcccgc gcatggccga gttgagcggt   300
tcccggctgg ccgcgcagca acagatggaa ggcctcctgg cgccgcaccg gcccaaggag   360
cccgcgtggt tcctggccac cgtcggcgtc tcgcccgacc accagggcaa gggtctgggc   420
agcgccgtcg tgctccccgg agtggaggcg gccgagcgcg ccggggtgcc cgccttcctg   480
gagacctccg cgccccgcaa cctccccttc tacgagcggc tcggcttcac cgtcaccgcc   540
gacgtcgagg tgcccgaagg accgcgcacc tggtgcatga cccgcaagcc cggtgcctga   600

<210> SEQ ID NO 10
<211> LENGTH: 717
<212> TYPE: DNA
<213> ORGANISM: Artificial
<220> FEATURE:
<223> OTHER INFORMATION: eGFP gene coding sequence

<400> SEQUENCE: 10
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctacgg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacaacag ccacaacgtc tatatcatgg ccgacaagca gaagaacggc   480
atcaaggtga acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg    660 ctggagttcg tgaccgccgc cgggatcact ctcggcatgg acgagctgta caagtaa     717

<210> SEQ ID NO 11
<211> LENGTH: 552

<212> TYPE: DNA
<213> ORGANISM: Artificial
<220> FEATURE:
<223> OTHER INFORMATION: IRES element

<400> SEQUENCE: 11

```
cccectaacg ttactggccg aagccgcttg gaataaggcc ggtgtgcgtt tgtctatatg    60
ttattttcca ccatattgcc gtcttttggc aatgtgaggg cccggaaacc tggccctgtc   120
ttcttgacga gcattcctag gggtctttcc cctctcgcca aggaatgcaa ggtctgttg    180
aatgtcgtga aggaagcagt tcctctggaa gcttcttgaa gacaaacaac gtctgtagcg   240
accctttgca ggcagcggaa ccccccacct ggcgacaggt gcctctgcgg ccaaaagcca   300
cgtgtataag atacacctgc aaaggcggca acccccagt gccacgttgt gagttggata    360
gttgtggaaa gagtcaaatg gctctcctca agcgtattca acaaggggct gaaggatgcc   420
cagaaggtac cccattgtat gggatctgat ctggggcctc ggtgcacatg ctttacatgt   480
gtttagtcga ggttaaaaaa cgtctaggcc ccccgaacca ggggacgtg gttttccttt    540
gaaaaacacg at                                                       552
```

<210> SEQ ID NO 12
<211> LENGTH: 397
<212> TYPE: DNA
<213> ORGANISM: Artificial
<220> FEATURE:
<223> OTHER INFORMATION: RSV promoter

<400> SEQUENCE: 12

```
ggatgtacgg gccagatata cgcgtatctg aggggactag ggtgtgttta ggcgaaaagc    60
ggggcttcgg ttgtacgcgg ttaggagtcc cctcaggata tagtagtttc gcttttgcat   120
agggaggggg aaatgtagtc ttatgcaata cacttgtagt cttgcaacat ggtaacgatg   180
agttagcaac atgccttaca aggagagaaa aagcaccgtg catgccgatt ggtggaagta   240
aggtggtacg atcgtgcctt attaggaagg caacagacag gtctgacatg gattggacga   300
accactgaat tccgcattgc agagataatt gtatttaagt gcctagctcg atacaataaa   360
cgccatttga ccattcacca cattggtgtg cacctcc                            397
```

<210> SEQ ID NO 13
<211> LENGTH: 327
<212> TYPE: DNA
<213> ORGANISM: Simian virus 40

<400> SEQUENCE: 13

```
cagctgtgga atgtgtgtca gttagggtgt ggaaagtccc caggctcccc agcaggcaga    60
agtatgcaaa gcatgcatct caattagtca gcaaccaggt gtggaaagtc cccaggctcc   120
ccagcaggca gaagtatgca aagcatgcat ctcaattagt cagcaaccat agtcccgccc   180
ctaactccgc ccatcccgcc cctaactccg cccagttccg cccattctcc gccccatggc   240
tgactaattt ttttatttta tgcagaggcc gaggccgcct cggcctctga gctattccag   300
aagtagtgag gaggcttttt tggaggc                                       327
```

<210> SEQ ID NO 14
<211> LENGTH: 1543
<212> TYPE: DNA
<213> ORGANISM: Artificial
<220> FEATURE:
<223> OTHER INFORMATION: Ubiquitin promoter

<400> SEQUENCE: 14

-continued

```
tctgccgagt cattgtcctt gtcccgcggc cccgggagcc cccgcgaccc ggcctgggag      60
gctcagggag gttgaagggg gctgagcaaa ggaagccccg tcattacctc aaatgtgacc     120
caaaaataaa gacccgtcca tctcgcaggg tgggccaggg cgggtcagga gggaggggag     180
ggagaccccg actctgcaga aggcgctcgc tgcgtgcccc acgtccgccg aacgcggggt     240
tcgcgacccg aggggaccgc gggggctgag gggaggggcc gcggagccgc ggctaaggaa     300
cgcgggccgc ccacccgctc cgggtgcagc ggcctccgcg ccgggttttg gcgcctcccg     360
cgggcgcccc cctcctcacg gcgagcgctg ccacgtcaga cgaagggcgc agcgagcgtc     420
ctgatccttc cgcccggacg ctcaggacag cggcccgctg ctcataagac tcggccttag     480
aaccccagta tcagcagaag gacattttag gacgggactt gggtgactct agggcactgg     540
ttttcttttcc agagagcgga acaggcgagg aaaagtagtc ccttctcggc gattctgcgg     600
agggatctcc gtggggcggt gaacgccgat gattatataa ggacgcgccg ggtgtggcac     660
agctagttcc gtcgcagccg ggattttggt cgcggttctt gtttgtggat cgctgtgatc     720
gtcacttggt gagtagcggg ctgctgggct ggccggggct ttcgtggccg ccgggccgct     780
cggtgggacg gaagcgtgtg gagagaccgc caagggctgt agtctgggtc cgcgagcaag     840
gttgccctga actgggggtt gggggggagcg cagcaaaatg gcggctgttc ccgagtcttg     900
aatgaaagac gcttgtgagg cgggctgtga ggtcgttgaa acaaggtggg gggcatggtg     960
ggcggcaaga acccaaggtc ttgaggcctt cgctaatgcg ggaaagctct tattcgggtg    1020
agatgggctg gggcaccatc tggggaccct gacgtgaagt tgtcactga  ctggagaact    1080
cggtttgtcg tctgttgcgg gggcggcagt tatggcggtg ccgttgggca gtgcacccgt    1140
acctttggga gcgcgcgccc tcgtcgtgtc gtgacgtcac ccgttctgtt ggcttataat    1200
gcagggtggg gccacctgcc ggtaggtgtg cggtaggctt ttctccgtcg caggacgcag    1260
ggttcgggcc tagggtaggc tctcctgaat cgacaggcgc cggacctctg gtgagggag    1320
ggataagtga ggcgtcagtt tctttggtcg gtttatgta cctatcttct taagtagctg    1380
aagctccggt tttgaactat gcgctcgggg ttggcgagtg tgttttgtga agttttttag    1440
gcaccttttg aaatgtaatc atttgggtca atatgtaatt ttcagtgtta gactagtaaa    1500
ttgtccgcta aattctggcc gttttttggct tttttgttag acg                     1543
```

<210> SEQ ID NO 15
<211> LENGTH: 455
<212> TYPE: DNA
<213> ORGANISM: Artificial
<220> FEATURE:
<223> OTHER INFORMATION: SB inverted repeats
<220> FEATURE:
<221> NAME/KEY: misc_feature
<222> LOCATION: (229)..(229)
<223> OTHER INFORMATION: n is a, c, g, or t

<400> SEQUENCE: 15

```
tacagttgaa gtcggaagtt tacatacact taagttggag tcattaaaac tcgttttca      60
actactccac aaatttcttg ttaacaaaca atagttttgg caagtcagtt aggacatcta     120
ctttgtgcat gacacaagtc attttttccaa caattgttta cagacagatt atttcactta     180
taattcactg tatcacaatt ccagtgggtc agaagtttac atacactand gtatgttaac     240
ttctgaccca ctgggaatgt gatgaaagaa ataaaagctg aaatgaatca ttctctctac     300
tattattctg tatatttcaca ttcttaaaat aaagtggtga tcctaactga ccttaagaca    360
gggaatcttt actcggatta aatgtcagga attgtgaaaa agtgagttta aatgtatttg    420
```

```
gctaaggtgt atgtaaactt ccgacttcaa ctgta                              455

<210> SEQ ID NO 16
<211> LENGTH: 6307
<212> TYPE: DNA
<213> ORGANISM: Artificial Sequence
<220> FEATURE:
<223> OTHER INFORMATION: Plasmid vector

<400> SEQUENCE: 16
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcggggctgg cttaactatg cggcatcaga gcagattgta ctgagagtgc   180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgaatt cgagctcggt accctacagt   420
tgaagtcgga gtttacata cacttaagtt ggagtcatta aaactcgttt ttcaactact   480
ccacaaattt cttgttaaca aacaatagtt ttggcaagtc agttaggaca tctactttgt   540
gcatgacaca agtcattttt ccaacaattg tttacagaca gattatttca cttataattc   600
actgtatcac aattccagtg ggtcagaagt ttacatacac taagttgact gtgcctttaa   660
acagcttgga aaattccaga aaatgatgtc atggctttag aagcttctga tagactaatt   720
gacatcattt gagtcaattg gaggtgtacc tgtggatgta tttcaaggga attctgtgga   780
atgtgtgtca gttagggtgt ggaaagtccc caggctcccc aggcaggcag aagtatgcaa   840
agcatcgagg atgtacgggc cagatatacg cgataacttc gtataatgta tgctatacga   900
agttatcgcg tgaggttttc accgtcatca ccgaaacgcg cgaggcagct gtggaatgtg   960
tgtcagttag ggtgtggaaa gtccccaggc tccccagcag gcagaagtat gcaaagcatg   1020
catctcaatt agtcagcaac caggtgtgga aagtccccag gctccccagc aggcagaagt   1080
atgcaaagca tgcatctcaa ttagtcagca accatagtcc cgcccctaac tccgcccatc   1140
ccgcccctaa ctccgcccag ttccgcccat tctccgcccc atggctgact aatttttttt   1200
atttatgcag aggccgaggc cgcctcggcc tctgagctat tccagaagta gtgaggaggc   1260
ttttttggag gctaccatgg agaagttact attccgaagt tcctattctc tagaaagtat   1320
aggaacttca agcttggcac tggtgagcaa gggcgaggag ctgttcaccg gggtggtgcc   1380
catcctggtc gagctggacg gcgacgtaaa cggccacaag ttcagcgtgt ccggcgaggg   1440
cgagggcgat gccacctacg gcaagctgac cctgaagttc atctgcacca ccggcaagct   1500
gcccgtgccc tggcccaccc tcgtgaccac cctgacctac ggcgtgcagt gcttcagccg   1560
ctaccccgac cacatgaagc agcacgactt cttcaagtcc gccatgcccg aaggctacgt   1620
ccaggagcgc accatcttct tcaaggacga cggcaactac aagacccgcg ccgaggtgaa   1680
gttcgagggc gacaccctgg tgaaccgcat cgagctgaag ggcatcgact tcaaggagga   1740
cggcaacatc ctggggcaca agctggagta caactacaac agccacaacg tctatatcat   1800
ggccgacaag cagaagaacg gcatcaaggt gaacttcaag atccgccaca acatcgagga   1860
cggcagcgtg cagctcgccg accactacca gcagaacacc cccatcggcg acggccccgt   1920
gctgctgccc gacaaccact acctgagcac ccagtccgcc ctgagcaaag accccaacga   1980
gaagcgcgat cacatggtcc tgctggagtt cgtgaccgcc gccgggatca ctctcggcat   2040
```

```
ggacgagctg tacaagtaaa gcggccgcgg ccaattgggc caccggtgct agcccctaa    2100
cgttactggc cgaagccgct tggaataagg ccggtgtgcg tttgtctata tgttattttc    2160
caccatattg ccgtcttttg gcaatgtgag ggcccggaaa cctggccctg tcttcttgac    2220
gagcattcct aggggtcttt cccctctcgc caaaggaatg caaggtctgt tgaatgtcgt    2280
gaaggaagca gttcctctgg aagcttcttg aagacaaaca acgtctgtag cgaccctttg    2340
caggcagcgg aacccccac ctggcgacag gtgcctctgc ggccaaaagc cacgtgtata    2400
agatacacct gcaaaggcgg cacaaccca gtgccacgtt gtgagttgga tagttgtgga    2460
aagagtcaaa tggctctcct caagcgtatt caacaagggg ctgaaggatg cccagaaggt    2520
accccattgt atgggatctg atctggggcc tcggtgcaca tgctttacat gtgtttagtc    2580
gaggttaaaa aacgtctagg ccccccgaac cacggggacg tggttttcct ttgaaaaaca    2640
cgataatacc atgaccgagt acaagcccac ggtgcgcctc ccacccgcg acgacgtccc    2700
ccgggccgta cgcaccctcg ccgccgcgtt cgccgactac cccgccacgc gccacaccgt    2760
cgatccggac cgccacatcg agcgggtcac cgagctgcaa gaactcttcc tcacgcgcgt    2820
cgggctcgac atcggcaagg tgtgggtcgc ggacgacggc gccgcggtgg cggtctggac    2880
cacgccggag agcgtcgaag cggggcggt gttcgccgag atcggcccgc gcatggccga    2940
gttgagcggt tcccgctgg ccgcgcagca acagatggaa ggcctcctgg cgccgcaccg    3000
gcccaaggag cccgcgtggt tcctggccac cgtcggcgtc tcgcccgacc accagggcaa    3060
gggtctgggc agcgccgtcg tgctccccgg agtggaggcg gccgagcgcg ccggggtgcc    3120
cgccttcctg gagacctccg cgccccgcaa cctccccttc tacgagcggc tcggcttcac    3180
cgtcaccgcc gacgtcgagg tgcccgaagg accgcgcacc tggtgcatga cccgcaagcc    3240
cggtgcctga cgcccgccca aagacccgc agcgcccgac cgaaaggagc gcacgacccc    3300
atgcatcgaa tcgatatcgc ggccgcgact ctagatcata atcagcccgg gggtgatcag    3360
cctcgactgt gccttctagt tgccagccat ctgttgtttg ccctcccc gtgccttcct    3420
tgaccctgga aggtgccact cccactgtcc tttcctaata aaatgaggaa attgcatcgc    3480
attgtctgag taggtgtcat tctattctgg gggtggggt ggggcaggac agcaagggg    3540
aggattggga agacaatagc aggcatgctg gggatgcggt gggctctatg gaaccagctg    3600
gggctcgaca ttctagttgt ggtttgtcca aactcatcaa tgtatcttat catgtctgga    3660
tcccatcaca aagctctgac ctcaatccta tagaaaggag gaatgagcca aaattcaccc    3720
aacttattgt gggaagcttg tggaaggcta ctcgaaatgt ttgacccaag ttaaacaatt    3780
taaaggcaat gctaccaaat actaattgag tgtatgttaa cttctgaccc actgggaatg    3840
tgatgaaaga aataaaagct gaaatgaatc attctctcta ctattattct gatatttcac    3900
attcttaaaa taaagtggtg atcctaactg accttaagac agggaatctt tactcggatt    3960
aaatgtcagg aattgtgaaa aagtgagttt aaatgtattt ggctaaggtg tatgtaaact    4020
tccgacttca actgtaggga tcctctagag tcgacctgca ggcatgcaag cttggcgtaa    4080
tcatggtcat agctgtttcc tgtgtgaaat tgttatccgc tcacaattcc acacaacata    4140
cgagccggaa gcataaagtg taaagcctgg ggtgcctaat gagtgagcta actcacatta    4200
attgcgttgc gctcactgcc cgcttccag tcgggaaacc tgtcgtgcca gctgcattaa    4260
tgaatcggcc aacgcgcggg gagaggcggt ttgcgtattg ggcgctcttc cgcttcctcg    4320
ctcactgact cgctgcgctc ggtcgttcgg ctgcggcgag cggtatcagc tcactcaaag    4380
gcggtaatac ggttatccac agaatcaggg gataacgcag gaaagaacat gtgagcaaaa    4440
```

```
ggccagcaaa aggccaggaa ccgtaaaaag gccgcgttgc tggcgttttt ccataggctc    4500 cgccccctg acgagcatca aaaaatcga cgctcaagtc agaggtggcg aaacccgaca       4560
ggactataaa gataccaggc gtttccccct ggaagctccc tcgtgcgctc tcctgttccg    4620
accctgccgc ttaccggata cctgtccgcc tttctccctt cgggaagcgt ggcgctttct    4680
caatgctcac gctgtaggta tctcagttcg gtgtaggtcg ttcgctccaa gctgggctgt    4740
gtgcacgaac cccccgttca gcccgaccgc tgcgccttat ccggtaacta tcgtcttgag    4800
tccaacccgg taagacacga cttatcgcca ctggcagcag ccactggtaa caggattagc    4860
agagcgaggt atgtaggcgg tgctacagag ttcttgaagt ggtggcctaa ctacggctac    4920
actagaagga cagtatttgg tatctgcgct ctgctgaagc cagttacctt cggaaaaaga    4980
gttggtagct cttgatccgg caaacaaacc accgctggta gcggtggttt ttttgtttgc    5040
aagcagcaga ttacgcgcag aaaaaaagga tctcaagaag atcctttgat cttttctacg    5100
gggtctgacg ctcagtggaa cgaaaactca cgttaaggga ttttggtcat gagattatca    5160
aaaaggatct tcacctagat ccttttaaat taaaaatgaa gttttaaatc aatctaaagt    5220
atatatgagt aaacttggtc tgacagttac caatgcttaa tcagtgaggc acctatctca    5280
gcgatctgtc tatttcgttc atccatagtt gcctgactcc ccgtcgtgta gataactacg    5340
atacgggagg gcttaccatc tggccccagt gctgcaatga taccgcgaga cccacgctca    5400
ccggctccag atttatcagc aataaaccag ccagccggaa gggccgagcg cagaagtggt    5460
cctgcaactt tatccgcctc catccagtct attaattgtt gccgggaagc tagagtaagt    5520
agttcgccag ttaatagttt gcgcaacgtt gttgccattg ctacaggcat cgtggtgtca    5580
cgctcgtcgt ttggtatggc ttcattcagc tccggttccc aacgatcaag gcgagttaca    5640
tgatccccca tgttgtgcaa aaaagcggtt agctccttcg gtcctccgat cgttgtcaga    5700
agtaagttgg ccgcagtgtt atcactcatg gttatggcag cactgcataa ttctcttact    5760
gtcatgccat ccgtaagatg cttttctgtg actggtgagt actcaaccaa gtcattctga    5820
gaatagtgta tgcggcgacc gagttgctct tgcccggcgt caatacggga taataccgcg    5880
ccacatagca gaactttaaa agtgctcatc attggaaaac gttcttcggg gcgaaaactc    5940
tcaaggatct taccgctgtt gagatccagt tcgatgtaac ccactcgtgc acccaactga    6000
tcttcagcat cttttacttt caccagcgtt tctgggtgag caaaaacagg aaggcaaaat    6060
gccgcaaaaa agggaataag ggcgacacgg aaatgttgaa tactcatact cttccttttt    6120
caatattatt gaagcattta tcagggttat tgtctcatga gcggatacat atttgaatgt    6180
atttagaaaa ataaacaaat aggggttccg cgcacatttc cccgaaaagt gccacctgac    6240
gtctaagaaa ccattattat catgacatta acctataaaa ataggcgtat cacgaggccc    6300
tttcgtc                                                              6307

<210> SEQ ID NO 17
<211> LENGTH: 6221
<212> TYPE: DNA
<213> ORGANISM: Artificial Sequence
<220> FEATURE:
<223> OTHER INFORMATION: Plasmid vector

<400> SEQUENCE: 17
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
```

| | |
|---|---|
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt accctacagt | 420 |
| tgaagtcgga agtttacata cacttaagtt ggagtcatta aaactcgttt ttcaactact | 480 |
| ccacaaattt cttgttaaca aacaatagtt ttggcaagtc agttaggaca tctactttgt | 540 |
| gcatgacaca agtcattttt ccaacaattg tttacagaca gattatttca cttataattc | 600 |
| actgtatcac aattccagtg ggtcagaagt ttacatacac taagttgact gtgcctttaa | 660 |
| acagcttgga aaattccaga aaatgatgtc atggctttag aagcttctga tagactaatt | 720 |
| gacatcattt gagtcaattg gaggtgtacc tgtggatgta tttcaaggga attctgtgga | 780 |
| atgtgtgtca gttagggtgt ggaaagtccc caggctcccc aggcaggcag aagtatgcaa | 840 |
| agcatcgagg atgtacgggc cagatatacg cgtatctgag gggactaggg tgtgtttagg | 900 |
| cgaaaagcgg ggcttcggtt gtacgcggtt aggagtcccc tcaggatata gtagtttcgc | 960 |
| ttttgcatag ggagggggaa atgtagtctt atgcaataca cttgtagtct tgcaacatgg | 1020 |
| taacgatgag ttagcaacat gccttacaag gagagaaaaa gcaccgtgca tgccgattgg | 1080 |
| tggaagtaag gtggtacgat cgtgccttat taggaaggca acagacaggt ctgacatgga | 1140 |
| ttggacgaac cactgaattc cgcattgcag agataattgt atttaagtgc ctagctcgat | 1200 |
| acaataaacg ccatttgacc attcaccaca ttggtgtgca cctccaaagc ttgatatcta | 1260 |
| ccatggagaa gttactattc cgaagttcct attctctaga aagtatagga acttcaagct | 1320 |
| tggcactggt gagcaagggc gaggagctgt tcaccgggt ggtgcccatc ctggtcgagc | 1380 |
| tggacggcga cgtaaacggc cacaagttca gcgtgtccgg cgagggcgag ggcgatgcca | 1440 |
| cctacggcaa gctgaccctg aagttcatct gcaccaccgg caagctgccc gtgccctggc | 1500 |
| ccaccctcgt gaccaccctg acctacggcg tgcagtgctt cagccgctac cccgaccaca | 1560 |
| tgaagcagca cgacttcttc aagtccgcca tgcccgaagg ctacgtccag gagcgcacca | 1620 |
| tcttcttcaa ggacgacggc aactacaaga cccgcgccga ggtgaagttc gagggcgaca | 1680 |
| ccctggtgaa ccgcatcgag ctgaagggca tcgacttcaa ggaggacggc aacatcctgg | 1740 |
| ggcacaagct ggagtacaac tacaacagcc acaacgtcta tatcatggcc gacaagcaga | 1800 |
| agaacggcat caaggtgaac ttcaagatcc gccacaacat cgaggacggc agcgtgcagc | 1860 |
| tcgccgacca ctaccagcag aacacccca tcggcgacgg ccccgtgctg ctgcccgaca | 1920 |
| accactacct gagcacccag tccgccctga gcaaagaccc caacgagaag cgcgatcaca | 1980 |
| tggtcctgct ggagttcgtg accgccgccg ggatcactct cggcatggac gagctgtaca | 2040 |
| agtaaagcat agcggccgta aattccgccc ctctctccct cccccccccc taacgttact | 2100 |
| ggccgaagcc gcttggaata aggccggtgt gcgtttgtct atatgttatt tccaccata | 2160 |
| ttgccgtctt ttggcaatgt gagggcccgg aaacctggcc ctgtcttctt gacgagcatt | 2220 |
| cctagggtc tttcccctct cgccaaagga atgcaaggtc tgttgaatgt cgtgaaggaa | 2280 |
| gcagttcctc tggaagcttc ttgaagacaa acaacgtctg tagcgaccct tgcaggcag | 2340 |
| cggaacccc cacctggcga caggtgcctc tgcggccaaa agccacgtgt ataagataca | 2400 |
| cctgcaaagg cggcacaacc ccagtgccac gttgtgagtt ggatagttgt ggaaagagtc | 2460 |
| aaatggctct cctcaagcgt attcaacaag ggctgaagg atgcccagaa ggtacccat | 2520 |
| tgtatgggat ctgatctggg gcctcggtgc acatgcttta catgtgttta gtcgaggtta | 2580 |

```
aaaaacgtct aggccccccg aaccacgggg acgtggtttt cctttgaaaa acacgatgat   2640
aagcttgcca caaccatgac cgagtacaag cccacggtgc gcctcgccac ccgcgacgac   2700
gtcccccggg ccgtacgcac cctcgccgcc gcgttcgccg actacccgc cacgcgccac   2760 accgtcgatc cggaccgcca catcgagcgg gtcaccgagc tgcaagaact cttcctcacg   2820
cgcgtcgggc tcgacatcgg caaggtgtgg gtcgcggacg acggcgccgc ggtggcggtc   2880
tggaccacgc cggagagcgt cgaagcgggg gcggtgttcg ccgagatcgg cccgcgcatg   2940
gccgagttga gcggttcccg gctggccgcg cagcaacaga tggaaggcct cctggcgccg   3000
caccggccca aggagcccgc gtggttcctg gccaccgtcg gcgtctcgcc cgaccaccag   3060
ggcaagggtc tgggcagcgc cgtcgtgctc cccggagtgg aggcggccga gcgcgccggg   3120
gtgcccgcct tcctggagac ctccgcgccc cgcaacctcc ccttctacga gcggctcggc   3180
ttcaccgtca ccgccgacgt cgaggtgccc gaaggaccgc gcacctggtg catgacccgc   3240
aagcccggtg cctgaagatc cccgggggga tcagcctcga ctgtgccttc tagttgccag   3300
ccatctgttg tttgcccctc ccccgtgcct tccttgaccc tggaaggtgc cactcccact   3360
gtcctttcct aataaaatga ggaaattgca tcgcattgtc tgagtaggtg tcattctatt   3420 ctgggggggtg gggtggggca ggacagcaag ggggaggatt gggaagacaa tagcaggcat   3480
gctggggatg cggtgggctc tatggaacca gctgggctc gacattctag ttgtggtttg   3540
tccaaactca tcaatgtatc ttatcatgtc tggatcccat cacaaagctc tgacctcaat   3600
cctatagaaa ggaggaatga gccaaaattc acccaactta ttgtgggaag cttgtggaag   3660
gctactcgaa atgtttgacc caagttaaac aatttaaagg caatgctacc aaatactaat   3720
tgagtgtatg ttaacttctg acccactggg aatgtgatga agaaataaa agctgaaatg   3780 aatcattctc tctactatta ttctgatatt tcacattctt aaaataaagt ggtgatccta   3840
actgacctta agacagggaa tctttactcg gattaaatgt caggaattgt gaaaaagtga   3900
gtttaaatgt atttggctaa ggtgtatgta aacttccgac ttcaactgta gggatcctct   3960
agagtcgacc tgcaggcatg caagcttggc gtaatcatgg tcatagctgt ttcctgtgtg   4020
aaattgttat ccgctcacaa ttccacacaa catacgagcc ggaagcataa agtgtaaagc   4080
ctggggtgcc taatgagtga gctaactcac attaattgcg ttgcgctcac tgcccgcttt   4140
ccagtcggga aacctgtcgt gccagctgca ttaatgaatc ggccaacgcg cggggagagg   4200
cggtttgcgt attgggcgct cttccgcttc ctcgctcact gactcgctgc gctcggtcgt   4260
tcggctgcgg cgagcggtat cagctcactc aaaggcggta atacggttat ccacagaatc   4320
aggggataac gcaggaaaga acatgtgagc aaaaggccag caaaaggcca ggaaccgtaa   4380
aaaggccgcg ttgctggcgt ttttccatag gctccgcccc cctgacgagc atcacaaaaa   4440
tcgacgctca agtcagaggt ggcgaaaccc gacaggacta taaagatacc aggcgtttcc   4500
ccctggaagc tccctcgtgc gctctcctgt tccgaccctg ccgcttaccg gatacctgtc   4560
cgcctttctc ccttcgggaa gcgtggcgct ttctcaatgc tcacgctgta ggtatctcag   4620
ttcggtgtag gtcgttcgct ccaagctggg ctgtgtgcac gaaccccccg ttcagcccga   4680
ccgctgcgcc ttatccggta actatcgtct tgagtccaac ccggtaagac acgacttatc   4740
gccactggca gcagccactg gtaacaggat tagcagagcg aggtatgtag gcggtgctac   4800
agagttcttg aagtggtggc ctaactacgg ctacactaga aggacagtat ttggtatctg   4860
cgctctgctg aagccagtta ccttcggaaa aagagttggt agctcttgat ccggcaaaca   4920
aaccaccgct ggtagcggtg gtttttttgt ttgcaagcag cagattacgc gcagaaaaaa   4980
```

```
aggatctcaa gaagatcctt tgatcttttc tacggggtct gacgctcagt ggaacgaaaa   5040
ctcacgttaa gggattttgg tcatgagatt atcaaaaagg atcttcacct agatccttt    5100 aaattaaaaa tgaagtttta aatcaatcta agtatatat gagtaaactt ggtctgacag    5160
ttaccaatgc ttaatcagtg aggcacctat ctcagcgatc tgtctatttc gttcatccat   5220
agttgcctga ctccccgtcg tgtagataac tacgatacgg gagggcttac catctggccc   5280
cagtgctgca atgataccgc gagacccacg ctcaccggct ccagatttat cagcaataaa   5340
ccagccagcc ggaagggccg agcgcagaag tggtcctgca actttatccg cctccatcca   5400
gtctattaat tgttgccggg aagctagagt aagtagttcg ccagttaata gtttgcgcaa   5460
cgttgttgcc attgctacag gcatcgtggt gtcacgctcg tcgtttggta tggcttcatt   5520
cagctccggt tcccaacgat caaggcgagt tacatgatcc cccatgttgt gcaaaaaagc   5580
ggttagctcc ttcggtcctc cgatcgttgt cagaagtaag ttggccgcag tgttatcact   5640
catggttatg gcagcactgc ataattctct tactgtcatg ccatccgtaa gatgcttttc   5700
tgtgactggt gagtactcaa ccaagtcatt ctgagaatag tgtatgcggc gaccgagttg   5760
ctcttgcccg gcgtcaatac gggataatac cgcgccacat agcagaactt taaaagtgct   5820
catcattgga aaacgttctt cggggcgaaa actctcaagg atcttaccgc tgttgagatc   5880
cagttcgatg taacccactc gtgcacccaa ctgatcttca gcatctttta ctttcaccag   5940
cgtttctggg tgagcaaaaa caggaaggca aaatgccgca aaaagggaa taagggcgac    6000 acggaaatgt tgaatactca tactcttcct ttttcaatat tattgaagca tttatcaggg   6060
ttattgtctc atgagcggat acatatttga atgtatttag aaaaataaac aatagggt     6120 tccgcgcaca tttccccgaa aagtgccacc tgacgtctaa gaaaccatta ttatcatgac   6180
attaacctat aaaaataggc gtatcacgag gccctttcgt c                        6221
```

<210> SEQ ID NO 18
<211> LENGTH: 6269
<212> TYPE: DNA
<213> ORGANISM: Artificial Sequence
<220> FEATURE:
<223> OTHER INFORMATION: Plasmid vector

<400> SEQUENCE: 18

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt accctacagt    420
tgaagtcgga gtttacata cacttaagtt ggagtcatta aaactcgttt ttcaactact     480
ccacaaattt cttgttaaca acaatagtt ttggcaagtc agttaggaca tctactttgt     540
gcatgacaca agtcattttt ccaacaattg tttacagaca gattatttca cttataattc    600
actgtatcac aattccagtg ggtcagaagt ttacatacac taagttgact gtgcctttaa    660
acagcttgga aaattccaga aaatgatgtc atggctttag aagcttctga tagactaatt   720
gacatcattt gagtcaattg gaggtgtacc tgtggatgta tttcaaggga attctgtgga    780
atgtgtgtca gttagggtgt ggaaagtccc caggctcccc aggcaggcag aagtatgcaa    840
```

```
agcatcgagg atgtacgggc cagatatacg cgtgaggttt tcaccgtcat caccgaaacg    900
cgcgaggcag ctgtggaatg tgtgtcagtt agggtgtgga aagtccccag gctcccagc    960 aggcagaagt atgcaaagca tgcatctcaa ttagtcagca accaggtgtg gaaagtcccc   1020
aggctcccca gcaggcagaa gtatgcaaag catgcatctc aattagtcag caaccatagt   1080
cccgccccta actccgccca tcccgcccct aactccgccc agttccgccc attctccgcc   1140
ccatggctga ctaattttt ttatttatgc agaggccgag gccgcctcgg cctctgagct    1200
attccagaag tagtgaggag gcttttttgg aggctaccat ggagaagtta ctattccgaa    1260
gttcctattc tctagaaagt ataggaactt caagcttggc actggtgagc aagggcgagg    1320
agctgttcac cggggtggtg cccatcctg tcgagctgga cggcgacgta aacggccaca    1380
agttcagcgt gtccggcgag ggcgagggcg atgccaccta cggcaagctg accctgaagt    1440
tcatctgcac caccggcaag ctgcccgtgc cctggcccac cctcgtgacc accctgacct    1500
acggcgtgca gtgcttcagc cgctaccccg accacatgaa gcagcacgac ttcttcaagt    1560
ccgccatgcc cgaaggctac gtccaggagc gcaccatctt cttcaaggac gacggcaact    1620
acaagacccg cgccgaggtg aagttcgagg gcgacaccct ggtgaaccgc atcgagctga    1680
agggcatcga cttcaaggag gacggcaaca tcctggggca caagctggag tacaactaca    1740
acagccacaa cgtctatatc atggccgaca agcagaagaa cggcatcaag gtgaacttca    1800
agatccgcca caacatcgag gacggcagcg tgcagctcgc cgaccactac cagcagaaca    1860
cccccatcgg cgacggcccc gtgctgctgc ccgacaacca ctacctgagc acccagtccg    1920
ccctgagcaa agaccccaac gagaagcgcg atcacatggt cctgctggag ttcgtgaccg    1980
ccgccgggat cactctcggc atggacgagc tgtacaagta aagcggccgc ggccaattgg    2040
gccaccggtg ctagcccct aacgttactg gccgaagccg cttggaataa ggccggtgtg    2100
cgtttgtcta tatgttattt tccaccatat tgccgtcttt tggcaatgtg agggcccgga    2160
aacctggccc tgtcttcttg acgagcattc ctaggggtct ttcccctctc gccaaaggaa    2220
tgcaaggtct gttgaatgtc gtgaaggaag cagttcctct ggaagcttct tgaagacaaa    2280
caacgtctgt agcgaccctt tgcaggcagc ggaaccccc acctggcgac aggtgcctct    2340
gcggccaaaa gccacgtgta taagatacac ctgcaaaggc ggcacaaccc cagtgccacg    2400
ttgtgagttg gatagttgtg gaaagagtca aatggctctc ctcaagcgta ttcaacaagg    2460
ggctgaagga tgcccagaag gtaccccatt gtatgggatc tgatctgggg cctcggtgca    2520
catgctttac atgtgtttag tcgaggttaa aaaacgtcta ggccccccga accacgggga    2580
cgtggttttc ctttgaaaaa cacgataata ccatgaccga gtacaagccc acggtgcgcc    2640
tcgccacccg cgacgacgtc cccgggccgg tacgcaccct cgccgccgcg ttcgccgact    2700
accccgccac gcgccacacc gtcgatccgg accgccacat cgagcgggtc accgagctgc    2760
aagaactctt cctcacgcgc gtcgggctcg acatcggcaa ggtgtgggtc gcggacgacg    2820
gcgccgcggt ggcggtctgg accacgccgg agagcgtcga agcggggcg tgttcgccg    2880 agatcggccc cgcatggcc gagttgagcg gttcccggct ggccgcgcag caacagatgg    2940
aaggcctcct ggcgccgcac cggcccaagg agcccgcgtg gttcctggcc accgtcggcg    3000
tctcgcccga ccaccagggc aagggtctgg gcagcgccgt cgtgctcccc ggagtggagg    3060
cggccgagcg cgccgggtg cccgccttcc tggagacctc cgcgcccgc aacctcccct    3120 tctacgagcg gctcggcttc accgtcaccg ccgacgtcga ggtgcccgaa ggaccgcgca    3180
cctggtgcat gacccgcaag cccggtgcct gacgcccgcc cacaagaccc gcagcgcccg    3240
```

```
accgaaagga gcgcacgacc ccatgcatcg aatcgatatc gcggccgcga ctctagatca    3300
taatcagccc gggggtgatc agcctcgact gtgccttcta gttgccagcc atctgttgtt    3360
tgcccctccc ccgtgccttc cttgaccctg gaaggtgcca ctcccactgt cctttcctaa    3420
taaaatgagg aaattgcatc gcattgtctg agtaggtgtc attctattct gggggtggg    3480 gtggggcagg acagcaaggg ggaggattgg gaagacaata gcaggcatgc tgggatgcg    3540 gtgggctcta tggaaccagc tggggctcga cattctagtt gtggtttgtc caaactcatc    3600
aatgtatctt atcatgtctg gatcccatca caaagctctg acctcaatcc tatagaaagg    3660
aggaatgagc caaaattcac ccaacttatt gtgggaagct tgtggaaggc tactcgaaat    3720
gtttgaccca agttaaacaa tttaaaggca atgctaccaa atactaattg agtgtatgtt    3780
aacttctgac ccactgggaa tgtgatgaaa gaaataaaag ctgaaatgaa tcattctctc    3840
tactattatt ctgatatttc acattcttaa aataaagtgg tgatcctaac tgaccttaag    3900
acagggaatc tttactcgga ttaaatgtca ggaattgtga aaaagtgagt ttaaatgtat    3960
ttggctaagg tgtatgtaaa cttccgactt caactgtagg gatcctctag agtcgacctg    4020
caggcatgca agcttggcgt aatcatggtc atagctgttt cctgtgtgaa attgttatcc    4080
gctcacaatt ccacacaaca tacgagccgg aagcataaag tgtaaagcct ggggtgccta    4140
atgagtgagc taactcacat taattgcgtt gcgctcactg cccgctttcc agtcgggaaa    4200
cctgtcgtgc cagctgcatt aatgaatcgg ccaacgcgcg gggagaggcg gtttgcgtat    4260
tgggcgctct tccgcttcct cgctcactga ctcgctgcgc tcggtcgttc ggctgcggcg    4320
agcggtatca gctcactcaa aggcggtaat acggttatcc acagaatcag gggataacgc    4380
aggaaagaac atgtgagcaa aaggccagca aaaggccagg aaccgtaaaa aggccgcgtt    4440
gctggcgttt ttccataggc tccgcccccc tgacgagcat cacaaaaatc gacgctcaag    4500
tcagaggtgg cgaaacccga caggactata aagataccag gcgtttcccc ctggaagctc    4560
cctcgtgcgc tctcctgttc cgaccctgcc gcttaccgga tacctgtccg cctttctccc    4620
ttcgggaagc gtggcgcttt ctcaatgctc acgctgtagg tatctcagtt cggtgtaggt    4680
cgttcgctcc aagctgggct gtgtgcacga accccccgtt cagcccgacc gctgcgcctt    4740
atccggtaac tatcgtcttg agtccaaccc ggtaagacac gacttatcgc cactggcagc    4800
agccactggt aacaggatta gcagagcgag gtatgtaggc ggtgctacag agttcttgaa    4860
gtggtggcct aactacggct acactagaag gacagtattt ggtatctgcg ctctgctgaa    4920
gccagttacc ttcggaaaaa gagttggtag ctcttgatcc ggcaaacaaa ccaccgctgg    4980
tagcggtggt ttttttgttt gcaagcagca gattacgcgc agaaaaaaag gatctcaaga    5040
agatcctttg atcttttcta cggggtctga cgctcagtgg aacgaaaact cacgttaagg    5100
gattttggtc atgagattat caaaaaggat cttcacctag atccttttaa attaaaaatg    5160
aagttttaaa tcaatctaaa gtatatatga gtaaacttgg tctgacagtt accaatgctt    5220
aatcagtgag gcacctatct cagcgatctg tctatttcgt tcatccatag ttgcctgact    5280
ccccgtcgtg tagataacta cgatacggga gggcttacca tctggcccca gtgctgcaat    5340
gataccgcga acccacgct caccggctcc agatttatca gcaataaacc agccagccgg    5400
aagggccgag cgcagaagtg gtcctgcaac tttatccgcc tccatccagt ctattaattg    5460
ttgccgggaa gctagagtaa gtagttcgcc agttaatagt ttgcgcaacg ttgttgccat    5520
tgctacaggc atcgtggtgt cacgctcgtc gtttggtatg gcttcattca gctccggttc    5580
ccaacgatca aggcgagtta catgatcccc catgttgtgc aaaaaagcgg ttagctcctt    5640
```

```
cggtcctccg atcgttgtca gaagtaagtt ggccgcagtg ttatcactca tggttatggc    5700
agcactgcat aattctctta ctgtcatgcc atccgtaaga tgcttttctg tgactggtga    5760
gtactcaacc aagtcattct gagaatagtg tatgcggcga ccgagttgct cttgcccggc    5820
gtcaatacgg gataataccg cgccacatag cagaacttta aaagtgctca tcattggaaa    5880
acgttcttcg gggcgaaaac tctcaaggat cttaccgctg ttgagatcca gttcgatgta    5940
acccactcgt gcacccaact gatcttcagc atcttttact ttcaccagcg tttctgggtg    6000
agcaaaaaca ggaaggcaaa atgccgcaaa aagggaata agggcgacac ggaaatgttg    6060
aatactcata ctcttccttt tcaatatta ttgaagcatt tatcagggtt attgtctcat    6120
gagcggatac atatttgaat gtatttagaa aaataaacaa ataggggttc cgcgcacatt    6180
tccccgaaaa gtgccacctg acgtctaaga accattatt atcatgacat aacctataa    6240 aaataggcgt atcacgaggc cctttcgtc                                      6269

<210> SEQ ID NO 19
<211> LENGTH: 6346
<212> TYPE: DNA
<213> ORGANISM: Artificial Sequence
<220> FEATURE:
<223> OTHER INFORMATION: Plasmid vector

<400> SEQUENCE: 19
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt accctacagt     420
tgaagtcgga gtttacata cacttaagtt ggagtcatta aaactcgttt ttcaactact     480
ccacaaattt cttgttaaca acaatagtt ttggcaagtc agttaggaca tctactttgt     540
gcatgacaca agtcattttt ccaacaattg tttacagaca gattatttca cttataattc     600
actgtatcac aattccagtg ggtcagaagt ttacatacac taagttgact gtgcctttaa     660
acagcttgga aaattccaga aatgatgtc atggctttag aagcttctga tagactaatt     720
gacatcattt gagtcaattg gaggtgtacc tgtggatgta tttcaaggga attctgtgga     780
atgtgtgtca gttagggtgt ggaaagtccc caggctcccc aggcaggcag aagtatgcaa     840
agcatcgagg atgtacgggc cagatatacg cgataacttc gtataatgta tgctatacga     900
agttatcgcg tgaggttttc accgtcatca ccgaaacgcg cgaggcagct gtggaatgtg     960
tgtcagttag ggtgtggaaa gtccccaggc tccccagcag gcagaagtat gcaaagcatg    1020
catctcaatt agtcagcaac caggtgtgga agtccccag gctccccagc aggcagaagt    1080
atgcaaagca tgcatctcaa ttagtcagca accatagtcc cgcccctaac tccgcccatc    1140
ccgcccctaa ctccgcccag ttccgcccat tctccgcccc atggctgact aatttttttt    1200
atttatgcag aggccgaggc cgcctcggcc tctgagctat tccagaagta gtgaggaggc    1260
ttttttggag gctaccatgg agaagttact attccgaagt tcctattctc tagaaagtat    1320
aggaacttca agcttggcac tggtgagcaa gggcgaggag ctgttcaccg ggtggtgccc    1380
catcctggtc gagctggacg gcgacgtaaa cggccacaag ttcagcgtgt ccggcgaggg    1440
```

```
cgagggcgat gccacctacg gcaagctgac cctgaagttc atctgcacca ccggcaagct    1500
gcccgtgccc tggcccaccc tcgtgaccac cctgacctac ggcgtgcagt gcttcagccg    1560 ctacccgac cacatgaagc agcacgactt cttcaagtcc gccatgcccg aaggctacgt    1620
ccaggagcgc accatcttct tcaaggacga cggcaactac aagacccgcg ccgaggtgaa    1680
gttcgagggc gacaccctgg tgaaccgcat cgagctgaag ggcatcgact tcaaggagga    1740
cggcaacatc ctggggcaca agctggagta caactacaac agccacaacg tctatatcat    1800
ggccgacaag cagaagaacg gcatcaaggt gaacttcaag atccgccaca acatcgagga    1860
cggcagcgtg cagctcgccg accactacca gcagaacacc cccatcggcg acggccccgt    1920
gctgctgccc gacaaccact acctgagcac ccagtccgcc ctgagcaaag accccaacga    1980
gaagcgcgat cacatggtcc tgctggagtt cgtgaccgcc gccgggatca ctctcggcat    2040
ggacgagctg tacaagtaaa gcggccgcgg ccaattgggc caccggtgct agcccctaa    2100 cgttactggc cgaagccgct tggaataagg ccggtgtgcg tttgtctata tgttattttc    2160
caccatattg ccgtcttttg gcaatgtgag ggcccggaaa cctggccctg tcttcttgac    2220
gagcattcct aggggtcttt cccctctcgc caaaggaatg caaggtctgt tgaatgtcgt    2280
gaaggaagca gttcctctgg aagcttcttg aagacaaaca acgtctgtag cgacccttg    2340 caggcagcgg aacccccac ctggcgacag gtgcctctgc ggccaaaagc cacgtgtata    2400
agatacacct gcaaggcgg cacaaccca gtgccacgtt gtgagttgga tagttgtgga    2460
aagagtcaaa tggctctcct caagcgtatt caacaagggg ctgaaggatg cccagaaggt    2520 acccattgt atgggatctg atctggggcc tcggtgcaca tgctttacat gtgtttagtc    2580
gaggttaaaa aacgtctagg ccccccgaac cacggggacg tggttttcct ttgaaaaaca    2640
cgataatacc atgaccgagt acaagcccac ggtgcgcctc gccacccgcg acgacgtccc    2700
ccgggccgta cgcaccctcg ccgccgcgtt cgccgactac cccgccacgc gccacaccgt    2760
cgatccggac cgccacatcg agcgggtcac cgagctgcaa gaactcttcc tcacgcgcgt    2820
cgggctcgac atcggcaagg tgtgggtcgc ggacgacggc gccgcggtgg cggtctggac    2880
cacgccggag agcgtcgaag cggggggcggt gttcgccgag atcggccgc gcatggccga    2940 gttgagcggt tccccgctgg ccgcgcagca acagatggaa ggcctcctgg cgccgcaccg    3000
gcccaaggag cccgcgtggt tcctggccac cgtcggcgtc tcgcccgacc accagggcaa    3060
gggtctgggc agcgccgtcg tgctccccgg agtggaggcg gccgagcgcg ccggggtgcc    3120
cgccttcctg gagacctccg cgccccgcaa cctccccttc tacgagcggc tcggcttcac    3180
cgtcaccgcc gacgtcgagg tgcccgaagg accgcgcacc tggtgcatga cccgcaagcc    3240
cggtgcctga cgcccgccca agacccgc agcgcccgac cgaaaggagc gcacgacccc    3300
atgcatcgaa tcgatatcgc ggccgcgact ctagatcata atcagccgg gggtgatcag    3360 cctcgactgt gccttctagt tgccagccat ctgttgtttg cccctccccc gtgccttcct    3420
tgaccctgga aggtgccact cccactgtcc tttcctaata aaatgaggaa attgcatcgc    3480
attgtctgag taggtgtcat tctattctgg ggggtggggt ggggcaggac agcaagggg    3540 aggattggga agacaatagc aggcatgctg gggatgcggt gggctctatg gaaccagctg    3600
gggcgcgatt aacttcgtat aaagtctcct atacgaagtt atcgcgccat tctagttgtg    3660
gtttgtccaa actcatcaat gtatcttatc atgtctggat cccatcacaa agctctgacc    3720
tcaatcctat agaaaggagg aatgagccaa aattcaccca acttattgtg ggaagcttgt    3780
ggaaggctac tcgaaatgtt tgacccaagt taaacaattt aaaggcaatg ctaccaaata    3840
```

```
ctaattgagt gtatgttaac ttctgaccca ctgggaatgt gatgaaagaa ataaaagctg   3900
aaatgaatca ttctctctac tattattctg atatttcaca ttcttaaaat aaagtggtga   3960
tcctaactga ccttaagaca gggaatcttt actcggatta aatgtcagga attgtgaaaa   4020
agtgagttta aatgtatttg gctaaggtgt atgtaaactt ccgacttcaa ctgtagggat   4080
cctctagagt cgacctgcag gcatgcaagc ttggcgtaat catggtcata gctgtttcct   4140
gtgtgaaatt gttatccgct cacaattcca cacaacatac gagccggaag cataaagtgt   4200
aaagcctggg gtgcctaatg agtgagctaa ctcacattaa ttgcgttgcg ctcactgccc   4260
gctttccagt cgggaaacct gtcgtgccag ctgcattaat gaatcggcca acgcgcgggg   4320
agaggcggtt tgcgtattgg gcgctcttcc gcttcctcgc tcactgactc gctgcgctcg   4380
gtcgttcggc tgcggcgagc ggtatcagct cactcaaagg cggtaatacg ttatccaca   4440 gaatcagggg ataacgcagg aaagaacatg tgagcaaaag gccagcaaaa ggccaggaac   4500
cgtaaaaagg ccgcgttgct ggcgtttttc cataggctcc gcccccctga cgagcatcac   4560
aaaaatcgac gctcaagtca gaggtggcga aacccgacag gactataaag ataccaggcg   4620
tttccccctg gaagctccct cgtgcgctct cctgttccga ccctgccgct taccggatac   4680
ctgtccgcct ttctcccttc gggaagcgtg gcgctttctc aatgctcacg ctgtaggtat   4740
ctcagttcgg tgtaggtcgt tcgctccaag ctgggctgtg tgcacgaacc ccccgttcag   4800
cccgaccgct gcgccttatc cggtaactat cgtcttgagt ccaacccggt aagacacgac   4860
ttatcgccac tggcagcagc cactggtaac aggattagca gagcgaggta tgtaggcggt   4920
gctacagagt tcttgaagtg gtggcctaac tacggctaca ctagaaggac agtatttggt   4980
atctgcgctc tgctgaagcc agttaccttc ggaaaaagag ttggtagctc ttgatccggc   5040
aaacaaacca ccgctggtag cggtggtttt tttgtttgca agcagcagat tacgcgcaga   5100
aaaaaaggat ctcaagaaga tcctttgatc ttttctacgg ggtctgacgc tcagtggaac   5160
gaaaactcac gttaagggat tttggtcatg agattatcaa aaaggatctt cacctagatc   5220
cttttaaatt aaaaatgaag ttttaaatca atctaaagta tatatgagta aacttggtct   5280
gacagttacc aatgcttaat cagtgaggca cctatctcag cgatctgtct atttcgttca   5340
tccatagttg cctgactccc cgtcgtgtag ataactacga tacgggaggg cttaccatct   5400
ggccccagtg ctgcaatgat accgcgagac ccacgctcac cggctccaga tttatcagca   5460
ataaaccagc cagccggaag ggccgagcgc agaagtggtc ctgcaacttt atccgcctcc   5520
atccagtcta ttaattgttg ccgggaagct agagtaagta gttcgccagt taatagtttg   5580
cgcaacgttg ttgccattgc tacaggcatc gtggtgtcac gctcgtcgtt tggtatggct   5640
tcattcagct ccggttccca acgatcaagg cgagttacat gatccccat gttgtgcaaa   5700 aaagcggtta gctccttcgg tcctccgatc gttgtcagaa gtaagttggc cgcagtgtta   5760
tcactcatgg ttatggcagc actgcataat tctcttactg tcatgccatc cgtaagatgc   5820
ttttctgtga ctggtgagta ctcaaccaag tcattctgag aatagtgtat gcggcgaccg   5880
agttgctctt gcccggcgtc aatacgggat aataccgcgc cacatagcag aactttaaaa   5940
gtgctcatca ttggaaaacg ttcttcgggg cgaaaactct caaggatctt accgctgttg   6000
agatccagtt cgatgtaacc cactcgtgca cccaactgat cttcagcatc ttttactttc   6060
accagcgttt ctgggtgagc aaaaacagga aggcaaaatg ccgcaaaaaa gggaataagg   6120
gcgacacgga aatgttgaat actcatactc ttccttttc aatattattg aagcatttat   6180
cagggttatt gtctcatgag cggatacata tttgaatgta tttagaaaaa taaacaaata   6240
```

```
ggggttccgc gcacatttcc ccgaaaagtg ccacctgacg tctaagaaac cattattatc    6300
atgacattaa cctataaaaa taggcgtatc acgaggccct ttcgtc                   6346

<210> SEQ ID NO 20
<211> LENGTH: 1023
<212> TYPE: DNA
<213> ORGANISM: Artificial
<220> FEATURE:
<223> OTHER INFORMATION: FRT hygro casette

<400> SEQUENCE: 20
ctattccttt gccctcggac gagtgctggg gcgtcggttt ccactatcgg cgagtacttc      60
tacacagcca tcggtccaga cggccgcgct tctgcgggcg atttgtgtac gcccgacagt     120
cccggctccg gatcggacga ttgcgtcgca tcgaccctgc gcccaagctg catcatcgaa     180
attgccgtca accaagctct gatagagttg gtcaagacca atgcggagca tatacgcccg     240
gagccgcggc gatcctgcaa gctccggatg cctccgctcg aagtagcgcg tctgctgctc     300
catacaagcc aaccacggcc tccagaagaa gatgttggcg acctcgtatt gggaatcccc     360
gaacatcgcc tcgctccagt caatgaccgc tgttatgcgg ccattgtccg tcaggacatt     420
gttggagccg aaatccgcgt gcacgaggtg ccggacttcg gggcagtcct cggcccaaag     480
catcagctca tcgagagcct gcgcgacgga cgcactgacg tgtcgtcca tcacagtttg     540 ccagtgatac acatggggat cagcaatcgc gcatatgaaa tcacgccatg tagtgtattg     600
accgattcct tgcggtccga atgggccgaa cccgctcgtc tggctaagat cggccgcagc     660
gatcgcatcc atggcctccg cgaccggctg cagaacagcg ggcagttcgg tttcaggcag     720
gtcttgcaac gtgacaccct gtgcacggcg ggagatgcaa taggtcaggc tctcgctgaa     780
ttccccaatg tcaagcactt ccggaatcgg gagcgcggcc gatgcaaagt gccgataaac     840
ataacgatct ttgtagaaac catcggcgca gctatttacc cgcaggacat atccacgccc     900
tcctacatcg aagctgaaag cacgagattc ttcgccctcc gagagctgca tcaggtcgga     960
gacgctgtcg aacttttcga tcagaaactt ctcgacagac gtcgcggtga gttcaggctt    1020
ttt                                                                 1023

<210> SEQ ID NO 21
<211> LENGTH: 9424
<212> TYPE: DNA
<213> ORGANISM: Artificial Sequence
<220> FEATURE:
<223> OTHER INFORMATION: Plasmid vector

<400> SEQUENCE: 21
aagcttggcc attgcatacg ttgtatccat atcataatat gtacatttat attggctcat      60
gtccaacatt accgccatgt tgacattgat tattgactag ttattaatag taatcaatta     120
cggggtcatt agttcatagc ccatatatgg agttccgcgt tacataactt acggtaaatg     180
gcccgcctgg ctgaccgccc aacgaccccc gcccattgac gtcaataatg acgtatgttc     240
ccatagtaac gccaataggg actttccatt gacgtcaatg ggtggagtat ttacggtaaa     300
ctgcccactt ggcagtacat caagtgtatc atatgccaag tacgccccct attgacgtca     360
atgacggtaa atggcccgcc tggcattatg cccagtacat gaccttatgg gactttccta     420
cttggcagta catctacgta ttagtcatcg ctattaccat ggtgatgcgg ttttggcagt     480
acatcaatgg gcgtggatag cggtttgact cacggggatt tccaagtctc caccccattg     540
acgtcaatgg gagtttgttt tggcaccaaa atcaacggga ctttccaaaa tgtcgtaaca     600
```

```
actccgcccc attgacgcaa atgggcggta ggcgtgtacg gtgggaggtc tatataagca      660
gagctcgttt agtgaaccgg ggtctctctg gttagaccag atctgagcct gggagctctc      720
tggctaacta gggaacccac tgcttaagcc tcaataaagc ttgccttgag tgcttcaagt      780
agtgtgtgcc cgtctgttgt gtgactctgg taactagaga tccctcagac ccttttagtc      840
agtgtggaaa atctctagca gtggcgcccg aacaggacc tgaaagcgaa agggaaacca       900
gagctctctc gacgcaggac tcggcttgct gaagcgcgca cggcaagagg cgaggggcgg      960
cgactggtga gtacgccaaa aattttgact agcggaggct agaaggagag agatgggtgc     1020
gagagcgtca gtattaagcg ggggagaatt agatcgcgat gggaaaaaat tcggttaagg     1080 ccaggggaa agaaaaaata taaattaaaa catatagtat gggcaagcag ggagctagaa       1140
cgattcgcag ttaatcctgg cctgttagaa acatcagaag gctgtagaca aatactggga     1200
cagctacaac catcccttca gacaggatca gaagaactta gatcattata taatacagta     1260
gcaaccctct attgtgtgca tcaaggata gagataaaag acaccaagga agctttagac       1320
aagatagagg aagagcaaaa caaaagtaag accaccgcac agcaagcggc cgctgatctt     1380
cagacctgga ggaggagata tgagggacaa ttggagaagt gaattatata aatataaagt     1440
agtaaaaatt gaaccattag gagtagcacc caccaaggca agagaagag tggtgcagag       1500 agaaaaaaga gcagtgggaa taggagcttt gttccttggg ttcttgggag cagcaggaag     1560
cactatgggc gcagcctcaa tgacgctgac ggtacaggcc agacaattat tgtctggtat     1620
agtgcagcag cagaacaatt tgctgagggc tattgaggcg caacagcatc tgttgcaact     1680
cacagtctgg ggcatcaagc agctccaggc aagaatcctg gctgtggaaa gatacctaaa     1740
ggatcaacag ctcctgggga tttggggttg ctctggaaaa ctcatttgca ccactgctgt     1800
gccttggaat gctagttgga gtaataaatc tctggaacag attggaatca cacgacctgg     1860
atggagtggg acagagaaat taacaattac acaagcttaa tacactcctt aattgaagaa     1920
tcgcaaaacc agcaagaaaa gaatgaacaa gaattattgg aattagataa atgggcaagt     1980
ttgtggaatt ggtttaacat aacaaattgg ctgtggtata taaaattatt cataatgata     2040
gtaggaggct tggtaggttt aagaatagtt tttgctgtac tttctatagt gaatagagtt     2100
aggcagggat attcaccatt atcgtttcag acccacctcc caaccccgag ggacccgac     2160 aggcccgaag gaatagaaga agaaggtgga gagagagaca gagacagatc cattcgatta     2220
gtgaacggat ctcgacggta tcggttctgg cacgacaggt ttcccgactg gaaagcgggc     2280
agtgagcgca acgcaattaa tgtgagttag ctcactcatt aggcacccca ggctttacac     2340
tttatgcttc cggctcgtat gttgtgtgga attgtgagcg gataacaatt tcacacagga     2400
aacagctatg accatgatta cgccaagctc tagctagagg tcgacggtat acagacatga     2460
taagatacat tgatgagttt ggacaaacca actagaat gcagtgaaaa aaatgcttta       2520
tttgtgaaat ttgtgatgct attgctttat ttgtaaccat tataagctgc aataaacaag     2580
ttggggtggg cgaagaactc cagcatgaga tccccgcgct ggaggatcat ccagccggcg     2640
tcccggaaaa cgattccgaa gcccaacctt tcatagaagg cggcggtgga atcgaaatct     2700
cgtagtacgt gctattcctt tgccctcgga cgagtgctgg ggcgtcggtt tccactatcg     2760
gcgagtactt ctacacagcc atcggtccag acggccgcgc ttctgcgggc gatttgtgta     2820
cgcccgacag tcccggctcc ggatcggacg attgcgtcgc atcgaccctg cgcccaagct     2880
gcatcatcga aattgccgtc aaccaagctc tgatagagtt ggtcaagacc aatgcggagc     2940
atatacgccc ggagccgcgg cgatcctgca agctccggat gcctccgctc gaagtagcgc     3000
```

```
gtctgctgct ccatacaagc caaccacggc ctccagaaga agatgttggc gacctcgtat    3060
tgggaatccc cgaacatcgc ctcgctccag tcaatgaccg ctgttatgcg gccattgtcc    3120
gtcaggacat tgttggagcc gaaatccgcg tgcacgaggt gccggacttc ggggcagtcc    3180
tcggcccaaa gcatcagctc atcgagagcc tgcgcgacgg acgcactgac ggtgtcgtcc    3240
atcacagttt gccagtgata cacatgggga tcagcaatcg cgcatatgaa atcacgccat    3300
gtagtgtatt gaccgattcc ttgcggtccg aatgggccga acccgctcgt ctggctaaga    3360
tcggccgcag cgatcgcatc catggcctcc gcgaccggct gcagaacagc gggcagttcg    3420
gtttcaggca ggtcttgcaa cgtgacaccc tgtgcacggc gggagatgca ataggtcagg    3480
ctctcgctga attccccaat gtcaagcact tccggaatcg ggagcgcggc cgatgcaaag    3540
tgccgataaa cataacgatc tttgtagaaa ccatcggcgc agctatttac ccgcaggaca    3600
tatccacgcc ctcctacatc gaagctgaaa gcacgagatt cttcgccctc cgagagctgc    3660
atcaggtcgg agacgctgtc gaacttttcg atcagaaact tctcgacaga cgtcgcggtg    3720
agttcaggct ttttggccaa ggaagttcct atactttcta gagaatagga acttcggaat    3780
aggaacttct aggtacgtga accatcaccc taatcaagtt ttttgggtc gaggtgccgt    3840 aaagcactaa atcggaaccc taaagggacc cccgatttag agcttgacgg ggaaagccgg    3900
cgaacgtggc gagaaaggaa gggaagaaag cgaaaggagc gggcgctagg gcgctggcaa    3960
gtgtagcggt cacgctgcgc gtaaccacca cacccgccgc gcttaatgcg ccgctacagg    4020
gcgcgtgggg ataccccta gagccccaga acttttaaaa gaaaaggggg gattgggggg    4080
tacagtgcag gggaaagaat agtagacata atagcaacag acatacaaac taaagaatta    4140
caaaaacaaa ttacaaaaat tcaaaatttt atcgatcacg agactagcct cgacgatggt    4200
cgagtaccgg gtaggggagg cgcttttccc aaggcagtct ggagcatgcg ctttagcagc    4260
cccgctgggc acttggcgct acacaagtgg cctctggcct cgcacacatt ccacatccac    4320
cggtaggcgc caaccggctc cgttcttttgg tggcccctt cgccaccttt ctactcctcc    4380
cctagtcagg aagttccccc ccgccccgca gctcgcgtcg tgcaggacgt gacaaatgga    4440
agtagcacgt ctcactagtc tcgtgcagat ggacagcacc gctgagcaat ggaagcgggt    4500
aggcctttgg ggcagcggcc aatagcagct ttgctccttc gctttctggg ctcagaggct    4560
gggaaggggt gggtccgggg gcgggctcag gggcgggctc aggggcgggg cgggcgcccg    4620
aaggtcctcc ggaggcccgg cattctgcac gcttcaaaag cgcacgtctg ccgcgctgtt    4680
ctcctcttcc tcatctccgg gccttttcgac ctctagcggg atccaagctt accatgaccg    4740
agtacaagcc cacggtgcgc ctcgccaccc gcgacgacgt cccccgggcc gtacgcaccc    4800
tcgccgccgc gttcgccgac taccccgcca cgcgccacac cgtcgacccg gaccgccaca    4860
tcgagcgggt caccgagctg caagaactct tcctcacgcg cgtcgggctc gacatcggca    4920
aggtgtgggt cgcggacgac ggcgccgcgg tggcggtctg gaccacgccg gagagcgtcg    4980
aagcgggggc ggtgttcgcc gagatcggcc cgcgcatggc cgagttgagc ggttcccggc    5040
tggccgcgca gcaacagatg gaaggcctcc tggcgccgca ccggcccaag gagcccgcgt    5100
ggttcctggc caccgtcggc gtctcgcccg accaccaggg caagggtctg ggcagcgccg    5160
tcgtgctccc cggagtggag gcggccgagc gcgccggggt gccgccttc ctggagacct    5220 ccgcgccccg caacctcccc ttctacgagc ggctcggctt caccgtcacc gccgacgtcg    5280
aggtgcccga aggaccgcgc acctggtgca tgacccgcaa gcccggtgcc tgactcgagg    5340
gaattccgat aatcaacctc tggattacaa aatttgtgaa agattgactg gtattcttaa    5400
```

```
ctatgttgct cctttacgc tatgtggata cgctgcttta atgcctttgt atcatgctat    5460
tgcttcccgt atggctttca ttttctcctc cttgtataaa tcctggttgc tgtctcttta    5520
tgaggagttg tggcccgttg tcaggcaacg tggcgtggtg tgcactgtgt ttgctgacgc    5580
aaccccact ggttggggca ttgccaccac ctgtcagctc ctttccggga ctttcgcttt     5640
ccccctccct attgccacgg cggaactcat cgccgcctgc cttgcccgct gctggacagg    5700
ggctcggctg ttgggcactg acaattccgt ggtgttgtcg gggaagctga cgtcctttcc    5760
atggctgctc gcctgtgttg ccacctggat tctgcgcggg acgtccttct gctacgtccc    5820
ttcggccctc aatccagcgg accttccttc ccgcggcctg ctgccggctc tgcggcctct    5880
tccgcgtctt cgccttcgcc ctcagacgag tcggatctcc ctttgggccg cctccccgca    5940
tcgggaattc gagctcggta cctttaagac caatgactta caaggcagct gtagatctta    6000
gccactttt aaaagaaaag gggggactgg aagggctaat tcactcccaa cgaagacaag    6060
atctgctttt tgcttgtact gggtctctct ggttagacca gatctgagcc tgggagctct    6120
ctggctaact agggaaccca ctgcttaagc ctcaataaag cttgccttga gtgcttcaag    6180
tagtgtgtgc ccgtctgttg tgtgactctg gtaactagag atccctcaga ccctttagt    6240
cagtgtggaa aatctctagc agcatctagc tagaattaat tccgtgtatt ctatagtgtc    6300
acctaaatcg tatgtgtatg atacataagg ttatgtatta attgtagccg cgttctaacg    6360
acaatatgta caagcctaat tgtgtagcat ctggcttact gaagcagacc ctatcatctc    6420
tctcgtaaac tgccgtcaga gtcggtttgg ttggacgaac cttctgagtt tctggtaacg    6480
ccgtcccgca cccggaaatg gtcagcgaac caatcagcag ggtcatcgct agcctaggct    6540
tttgcgtcga gacgtaccca attgccccta tagtgagtcg tattacgcgc gctcactggc    6600
cgtcgtttta caacgtcgtg actgggaaaa ccctggcgtt acccaactta atcgccttgc    6660
agcacatccc cctttcgcca gctggcgtaa tagcgaagag gcccgcaccg atcgcccttc    6720
ccaacagttg cgcagcctga atggcgaatg gcgcgacgcg ccctgtagcg cgcattaag    6780
cgcggcgggt gtggtggtta cgcgcagcgt gaccgctaca cttgccagcg ccctagcgcc    6840
cgctcctttc gctttcttcc cttcctttct cgccacgttc gccggctttc cccgtcaagc    6900
tctaaatcgg gggctccctt tagggttccg atttagtgct ttacggcacc tcgaccccaa    6960
aaaacttgat tagggtgatg gttcacgtag tgggccatcg ccctgataga cggttttcg    7020
ccctttgacg ttggagtcca cgttctttaa tagtggactc ttgttccaaa ctggaacaac    7080
actcaaccct atctcggtct attcttttga tttataaggg attttgccga tttcggccta    7140
ttggttaaaa aatgagctga tttaacaaaa atttaacgcg aatttaaca aaatattaac     7200
gtttacaatt tcccaggtgg cacttttcgg ggaaatgtgc gcggaacccc tatttgttta    7260
tttttctaaa tacattcaaa tatgtatccg ctcatgagac aataaccctg ataaatgctt    7320
caataatatt gaaaaaggaa gagtatgagt attcaacatt tccgtgtcgc ccttattccc    7380
ttttttgcgg cattttgcct tcctgttttt gctcacccag aaacgctggt gaaagtaaaa    7440
gatgctgaag atcagttggg tgcacgagtg ggttacatcg aactggatct caacagcggt    7500
aagatccttg agagttttcg ccccgaagaa cgttttccaa tgatgagcac ttttaaagtt    7560
ctgctatgtg gcgcggtatt atcccgtatt gacgccggc aagagcaact cggtcgccgc     7620
atacactatt ctcagaatga cttggttgag tactcaccag tcacagaaaa gcatcttacg    7680
gatggcatga cagtaagaga attatgcagt gctgccataa ccatgagtga taacactgcg    7740
gccaacttac ttctgacaac gatcggagga ccgaaggagc taaccgcttt tttgcacaac    7800
```

-continued

```
atgggggatc atgtaactcg ccttgatcgt tgggaaccgg agctgaatga agccatacca    7860
aacgacgagc gtgacaccac gatgcctgta gcaatggcaa caacgttgcg caaactatta    7920
actggcgaac tacttactct agcttcccgg caacaattaa tagactggat ggaggcggat    7980
aaagttgcag gaccacttct gcgctcggcc cttccggctg gctggtttat tgctgataaa    8040
tctggagccg gtgagcgtgg gtctcgcggt atcattgcag cactgggcc agatggtaag    8100 ccctcccgta tcgtagttat ctacacgacg gggagtcagg caactatgga tgaacgaaat    8160
agacagatcg ctgagatagg tgcctcactg attaagcatt ggtaactgtc agaccaagtt    8220
tactcatata tactttagat tgatttaaaa cttcattttt aatttaaaag gatctaggtg    8280
aagatccttt ttgataatct catgaccaaa atcccttaac gtgagttttc gttccactga    8340
gcgtcagacc ccgtagaaaa gatcaaagga tcttcttgag atcctttttt tctgcgcgta    8400
atctgctgct tgcaaacaaa aaaaccaccg ctaccagcgg tggtttgttt gccggatcaa    8460
gagctaccaa ctctttttcc gaaggtaact ggcttcagca gagcgcagat accaaatact    8520
gtccttctag tgtagccgta gttaggccac cacttcaaga actctgtagc accgcctaca    8580
tacctcgctc tgctaatcct gttaccagtg gctgctgcca gtggcgataa gtcgtgtctt    8640
accgggttgg actcaagacg atagttaccg gataaggcgc agcggtcggg ctgaacgggg    8700
ggttcgtgca cacagcccag cttggagcga acgacctaca ccgaactgag atacctacag    8760
cgtgagctat gagaaagcgc cacgcttccc gaagggagaa aggcggacag gtatccggta    8820
agcggcaggg tcggaacagg agagcgcacg agggagcttc caggggggaaa cgcctggtat    8880 ctttatagtc ctgtcgggtt tcgccacctc tgacttgagc gtcgattttt gtgatgctcg    8940 tcagggggc ggagcctatg gaaaaacgcc agcaacgcgg cctttttacg gttcctggcc    9000
ttttgctggc cttttgctca catgttcttt cctgcgttat cccctgattc tgtggataac    9060
cgtattaccg cctttgagtg agctgatacc gctcgccgca gccgaacgac cgagcgcagc    9120
gagtcagtga gcgaggaagc ggaagagcgc ccaatacgca aaccgcctct ccccgcgcgt    9180
tggccgattc attaatgcag ctggcacgac aggtttcccg actggaaagc gggcagtgag    9240
cgcaacgcaa ttaatgtgag ttagctcact cattaggcac cccaggcttt acactttatg    9300
cttccggctc gtatgttgtg tggaattgtg agcggataac aatttcacac aggaaacagc    9360
tatgaccatg attacgccaa gcgcgcaatt aaccctcact aaagggaaca aaagctggag    9420
ctgc                                                                 9424
```

PIG WHOSE GENOME COMPRISES A HETEROLOGOUS SITE-SPECIFIC RECOMBINATION SITE AND A TRANSPOHON TAG

FIELD OF INVENTION

The present invention relates to a genetically modified pig comprising at least one site for integration of at least one transgene. The invention also pertains to a recombinant target vector and uses thereof. Methods are disclosed for the production of genetically modified pigs.

BACKGROUND OF INVENTION

Transgenic, non-human animals can be used to understand the action of a single gene or genes in the context of the whole animal and the interrelated phenomena of gene activation, expression, and interaction. The technology has also led to the production of models for various diseases in humans and other animals which contributes significantly to an increased understanding of genetic mechanisms and of genes associated with specific diseases.

Traditionally, smaller animals such as mice have been used as disease models for human diseases and have been found to be suitable as models for certain diseases. However, their value as animal models for many human diseases is quite limited due to differences in mice compared to humans. Larger transgenic animals are much more suitable than mice for the study of many of the effects and treatments of most human diseases because of their greater similarity to humans in many aspects. Particularly, pigs are believed to be valuable as disease models for human diseases.

Integration of foreign DNA plays a pivotal role in both genetic manipulation of cell lines and technologies related to therapeutic gene transfer. Current integrations strategies, based upon for example retroviral, lentiviral or DNA transposon-based vector systems allow efficient gene insertion, but all suffer from the fact that gene insertion is not controllable and cannot be directed to predetermined positions in the genomic DNA. The yeast Flp recombinase, in contrast, facilitates sequence-specific integration (1), but the Flp recombination target sequence (FRT) does not exist in mammalian genomes. The site of integration is of great importance for the gene expression profile of the inserted gene. Hence, in some positions the gene will be stably expressed, whereas other positions are unable to support long-term expression due to strong influences from the flanking DNA leading to transcriptional silencing. Such actions upon the transgene may lead to reduced expression or complete shut-down of expression depending on cell type or tissue. For several purposes it is therefore of great importance to direct insertion towards 'stably' expressing loci. This may have particular importance in genetically manipulated animal models in which continued gene expression in the tissue of interest is essential for genetic studies. As another important example, cell therapies in which genetically altered effector cells are administered to patients (as in some cancer immunotherapy protocols) rely on stable transgene expression from loci that are not silenced over time.

The tyrosine recombinases Flp (2) and Cre, derived from yeast and E. coli phages, respectively, and the serine recombinase φC31 from S. lividans phages are cherished for their site-specific integrating properties. φC31 has been found to facilitate plasmid DNA recombination into pseudo recognition sites in the human genome and therefore has been extensively explored as a tool in gene therapy (3). In case of Flp and Cre, however, the human genome does not contain recombination target sites and these sites need to be introduced in the genome prior to successful gene insertion (1). Although Cre-based recombination has been heavily studied and appears to be a bit more effectful than Flp in human cells, a now widely used Flp-based integration system has been commercialized by Invitrogen (cat. no. K6010-01). This system is based on a FRT sequence contained within a lacZ-Zeocin fusion gene. This FRT-tagged gene is inserted into cells by nonhomologous recombination, an uncontrolled recombination process which is believed often to involve concatamer formation, leading to insertion of more than one copies of the foreign DNA. Characterized cell lines containing this FRT-lacZzeo insert are currently offered by Invitrogen, allowing researchers to insert plasmid DNA containing their gene of interest into the FRT-tagged locus on offer in the particular cell line. This plasmid contains not only the transgene but also a FRT-hygro cassette that does not contain a start codon. By recombination between the two FRT sites (one in the genome and one on the plasmid) the start codon of the lacZzeo fusion is fused to the FRT-hygro cassette, allowing for expression of the hygro gene and subsequent selection for hygromycin B resistance. This technology facilitates insertion of the entire plasmid including the bacterial backbone which is believed to have a negative impact on gene expression in mammalian cells potentially be inducing posttranscriptional silencing.

Transcriptional silencing of foreign genetic material is a fundamental problem in gene transfer and genetic engineering of cells and animals. Due to epigenetic modifications transgenic animal models therefore often suffer from reduced gene expression, or the lack of gene activity in tissues in which transcription is required to develop a desired phenotype. The choice of promoter influences the overall transgene expression profile in a transgenic animal and to a certain degree the level of gene silencing. However, positional effects and spreading of heterochromatin from flanking genomic regions are major contributors to gene silencing, and the site of integration of a transgene is crucial, therefore, for the fate of a foreign gene. In rodents, well-characterized loci supporting long-term gene expression have been identified. Based on these findings transgenic animal models have been generated by inserting genes by homologous recombination into such preferred sites.

The establishment of cloned pig models of genetic disease, is challenged by problems in identifying genomic loci that support ubiquitous or, for some models, tissue-specific expression of an inserted transgene. At present, the information that allows the insertion of genes into well-suited and predefined loci of porcine cells is not available. Moreover, by inserting disease genes at random positions we risk to target genomic sites that are eventually silenced during pig development and growth. Therefore, a need exists for a genetically modified pig harbouring an insertion site that allows for the integration of a transgene at a position in the genome wherein the transgene is stably expressed.

SUMMARY OF INVENTION

The present invention concerns a genetically modified pig which allows for integration of transgenes for example disease-causing genes that will allow the study of said diseases. The genetically modified pig harbours a site for integration of a transgene in a stably expressing locus.

The present invention discloses a novel DNA transposon based approach for tagging the chromosomal DNA of cells of interest by introducing one or more recombination sites for site specific recombinases. Genes of interest for example genetic determinants of disease can subsequently be inserted into the genome of the cell by the use of substrates for recombination carrying the gene of interest.

Thus, one aspect of the present invention relates to a genetically modified pig, wherein the genetically modified genome comprises at least one site for integration of at least one transgene.

A second aspect of the present invention pertains to a genetically modified porcine blastocyst derived from the genetically modified pig model, wherein the genetically modified genome comprises at least one site for integration of at least one transgene, and/or a genetically modified porcine blastocyst, wherein the genetically modified genome comprises at least one site for integration of at least one transgene.

Similarly, a third aspect relates to a genetically modified porcine embryo derived from the genetically modified pig model, wherein the genetically modified genome comprises at least one site for integration of at least one transgene, and/or a genetically modified porcine embryo, wherein the genetically modified genome comprises at least one site for integration of at least one transgene.

Furthermore, a fourth aspect relates to a genetically modified porcine fetus derived from the genetically modified pig model, wherein the genetically modified genome comprises at least one site for integration of at least one transgene, and/or a genetically modified porcine fetus, wherein the genetically modified genome comprises at least one site for integration of at least one transgene.

A fifth aspect of the present invention pertains to a genetically modified porcine donor cell and/or cell nucleus derived from the genetically modified pig model, wherein the genetically modified genome comprises at least one site for integration of at least one transgene, and/or a genetically modified porcine donor cell and/or cell nucleus, wherein the genetically modified genome comprises at least one site for integration of at least one transgene.

It is appreciated that in a preferred embodiment of the present invention the at least one site for integration of at least one transgene is a heterologous recombination site.

Embodiments for the present invention comprises minipigs for example selected from the group consisting of Goettingen, Yucatan, Bama Xiang Zhu, Wuzhishan and Xi Shuang Banna, including any combination thereof. In a preferred embodiment the pig, embryo, blastocyst, fetus and/or cells thereof is a Goettingen minipig. However, another embodiment relates to pigs that are not a mini-pig, such as the species of Sus domesticus, for example where the pig is selected from the group consisting of Landrace, Yorkshire, Hampshire, Duroc, Chinese Meishan, Berkshire and Piêtrain, including any combination thereof.

Embodiments of the present invention comprises the genetically modified pig, porcine embryo, blastocyst, fetus and/or cells thereof, wherein the genetically modified genome comprises at least one recombination site for site-specific gene insertion, for example at least one recombination site for Flp and/or Cre recombinase, or at least one recombination site is a recombination site for Flp. Thus the genetically modified pig comprises a transposon tagged genome by a recombinant vector as disclosed herein. The genetically modified pig may further comprise at least one transgene, displaying a phenotype associated with disease.

A sixth aspect of the invention pertains to a genetically modified pig, porcine embryo, blastocyst, fetus and/or donor cell, wherein the genetically modified genome comprises at least one gene of interest obtained by recombination into the at least one site for integration. Such a genetically modified pig, porcine embryo, blastocyst, fetus and/or donor cell is for example obtainable by use of the recombinant vector as disclosed elsewhere herein and/or by the system described elsewhere herein.

A seventh aspect of the invention pertains to a recombinant target vector comprising a DNA transposon construct comprising a bicistronic gene cassette comprising (i) at least one recombination site and ii) an IRES-driven selection gene. Within the scope of the present invention is for example the recombinant vector, wherein said DNA transposon is the Sleeping Beauty (SB) DNA transposon. The DNA transposon is for example selected from the group consisting of the Sleeping Beauty (SB) transposon, Frog Prince (FP) transposon, Piggybac transposon, Tol2 transposon, Himar 1 transposon and passport transposon. In a particular embodiment the DNA transposon is the Sleeping Beauty transposon. The recombinant target vector in one embodiment comprises at least one FRT, attB/P and/or LoxP recombination site. In a preferred embodiment the recombinant target vector comprises at least one recombination site in the form of a FRT and/or LoxP recombination site, more preferably a FRT recombination site. The recombination site is in one embodiment embedded in the coding sequence of a reporter gene and/or selection gene, for example the eGFP gene, for example the FRT recombination site is embedded in a SV40 promoter driven fusion variant of eGFP. Another embodiment of the present invention relates to the genes driven by the IRES, wherein said gene is a gene conferring resistance to a drug, for example a puromycin resistance gene. The recombinant vector further comprises in another embodiment at least one recognition site for a Cre recombinase, for example wherein said at least one recognition site for Cre recombinase is located between the upper inverted repeat of the vector and the SV40 promoter, for example wherein said at least one recognition site for Cre recombinase is located between the poly A sequence and the lower inverted repeat of the vector.

A further aspect of the present invention relates to a bi-phase system comprising a recombinant target vector as disclosed herein and a recombination substrate. A recombination substrate comprises a fusion of at least one recognition site for a recombinase and a gene of interest. In one embodiment of this aspect the recombination substrate is present in a plasmid, an in vitro generated plasmid-derived minicircle and/or a lentiviral circle.

Yet a further aspect of the present invention relates to a mammalian cell comprising a DNA transposon tagged genome containing a recombination target site for site-specific gene integration. In one embodiment of the invention the recombination target site is a heterologous target site not ordinarily found in the genome of the mammalian cell. In one embodiment the cell comprises a DNA transposon tagged genome by a recombinant vector as defined herein. In another embodiment the genome of the cell further contains at least one recognition site for Cre-recombinase. The mammalian cell is a somatic cell, for example of porcine origin, for example a fibroblast, such as a primary somatic cell, for example a porcine primary fibroblast, or a porcine neonatal fibroblast.

An additional aspect of the present invention pertains to a method for producing a mammalian cell comprising a DNA transposon tagged genome comprising at least one recombination target site for site-specific gene insertion comprising the steps of a) providing a mammalian cell, b) transfecting the cell of a) with a plasmid expressing a transposase and a recombinant vector comprising a DNA transposon construct and a bicistronic gene cassette comprising (i) a recombination site and ii) an IRES-driven selection gene, c) selecting DNA transposon tagged cells. In one embodiment the method further comprises a step of recombination using the recombination substrate as disclosed herein. The cell of the method is a somatic cell, for example of porcine origin, for example a fibroblast, such as a primary somatic cell, for example a porcine primary fibroblast.

A further aspect of the present invention relates to a method for obtaining the genetically modified pig, porcine embryo, blastocyst, fetus and/or donor cell, wherein the genetically modified genome comprises at least one site for integration of at least one transgene comprising the steps of i) providing a donor cell, ii) genetically modifying the donor cell of i) by inserting the recombinant vector as defined herein into the genome of said donor cell, iii) transferring the modified genome of the donor cell obtained in ii) into a host cell, iv) obtaining a reconstructed embryo forming an embryo, v) culturing said embryo; and vii) transferring said cultured embryo to a host mammal such that the embryo develops into a genetically modified fetus, wherein said genetically modified embryo obtainable by nuclear transfer comprises steps i) to v) and/or vi), wherein said genetically modified blastocyst obtainable by nuclear transfer comprises steps i) to vi) and/or vii), wherein said genetically modified fetus obtainable by nuclear transfer comprises steps i) to vii)

Yet a further aspect of the present invention concerns a genetically modified pig model, porcine embryo, blastocyst, fetus and/or donor cell, wherein the genetically modified genome comprises at least one site for integration of at least one transgene obtainable by nuclear transfer comprising the steps of i) establishing at least one oocyte having at least a part of a modified zona pellucida, ii) separating the oocyte into at least two parts obtaining an oocyte having a nucleus and at least one cytoplast, iii) establishing a donor cell or cell nucleus with desired genetic properties, iv) fusing at least one cytoplast with the donor cell or membrane surrounded cell nucleus, v) obtaining a reconstructed embryo, vi) activating the reconstructed embryo to form an embryo; culturing said embryo; and vii) transferring said cultured embryo to a host mammal such that the embryo develops into a genetically modified fetus, wherein said genetically modified embryo obtainable by nuclear transfer comprises steps i) to v) and/or vi), wherein said genetically modified blastocyst obtainable by nuclear transfer comprises steps i) to vi) and/or vii), wherein said genetically modified fetus obtainable by nuclear transfer comprises steps i) to vii)

An additional aspect of the present invention pertains to a method for producing a genetically modified pig, porcine embryo, blastocyst, fetus and/or donor cell, comprising at least one recombination site comprising: i) establishing at least one oocyte, ii) separating the oocyte into at least three parts obtaining at least one cytoplast, iii) establishing a donor cell or cell nucleus having desired genetic properties, such as at least one heterologous recombination site iv) fusing at least one cytoplast with the donor cell or membrane surrounded cell nucleus, v) obtaining a reconstructed embryo, vi) activating the reconstructed embryo to form an embryo; culturing said embryo; and vii) transferring said cultured embryo to a host mammal such that the embryo develops into a genetically modified fetus, wherein said genetically modified embryo obtainable by nuclear transfer comprises steps i) to v) and/or vi), wherein said genetically modified blastocyst obtainable by nuclear transfer comprises steps i) to vi) and/or vii), wherein said genetically modified fetus obtainable by nuclear transfer comprises steps i) to vii)

Yet a further aspect relates to a method for producing a genetically modified pig, porcine embryo, blastocyst, fetus and/or donor cell comprising:

i) establishing at least one oocyte
ii) separating the oocyte into at least three parts obtaining at least one cytoplast,
iii) establishing a donor cell or cell nucleus having desired genetic properties, wherein the donor cell is established from a genetically modified pig carrying in its genome at least one site for integration of at least one transgene
iv) providing a transgene and integrating said transgene into the donor cell of iii)
v) fusing at least one cytoplast with the donor cell or membrane surrounded cell nucleus,
vi) obtaining a reconstructed embryo,
vii) activating the reconstructed embryo to form an embryo;
viii) culturing said embryo; and
ix) transferring said cultured embryo to a host mammal such that the embryo develops into a genetically modified fetus, wherein said genetically modified embryo obtainable by nuclear transfer comprises steps i) to v) and/or vi),
wherein said genetically modified blastocyst obtainable by nuclear transfer comprises steps i) to vi) and/or vii), wherein said genetically modified fetus obtainable by nuclear transfer comprises steps i) to vii)

A further aspect relates to the genetically modified pig model, porcine embryo, blastocyst, fetus and/or donor cell of the present invention obtainable by nuclear transfer comprising the steps of
i) establishing at least one oocyte having at least a part of a modified zona pellucida,
ii) separating the oocyte into at least two parts obtaining an oocyte having a nucleus and at least one cytoplast,
iii) establishing a donor cell or cell nucleus with desired genetic properties, wherein the donor cell is established from a genetically modified pig carrying in its genome at least one site for integration of at least one transgene
iv) providing a transgene and integrating said transgene into the donor cell of iii)
v) fusing at least one cytoplast with the donor cell or membrane surrounded cell nucleus,
vi) obtaining a reconstructed embryo,
vii) activating the reconstructed embryo to form an embryo; culturing said embryo; and
viii) transferring said cultured embryo to a host mammal such that the embryo develops into a genetically modified fetus, wherein said genetically modified embryo obtainable by nuclear transfer comprises steps i) to v) and/or vi), wherein said genetically modified blastocyst obtainable by nuclear transfer comprises steps i) to vi) and/or vii), wherein said genetically modified fetus obtainable by nuclear transfer comprises steps i) to vii).

Embodiments of the aspects comprise one or more of the features as defined herein, wherein the method for activation of the reconstructed embryo is selected from the group of methods consisting of electric pulse, chemically induced shock, increasing intracellular levels of divalent cations and reducing phosphorylation. Further embodiments of the second and third aspects comprise one or more of the features as defined above, wherein steps d) and f) are performed sequentially or simultaneously, and embodiments comprising one or more of the features, wherein the embryo is cultured in vitro. Such embryo may be cultured in sequential culture. The embryo, for example at the blastocyst stage, is cryopreserved prior to transfer to a host mammal. For the methods of the present invention embodiments cover pigs, mini-pigs for example selected from the group consisting of Goettingen, Yucatan, Bama Xiang Zhu, Wuzhishan and Xi Shuang Banna, including any combination thereof. However, another embodiment relates to pigs that are not a mini-pig, such as the species of Sus domesticus, for example where the pig is selected from the group consisting of Landrace, Yorkshire, Hampshire, Duroc, Chinese Meishan, Berkshire and Piètrain, including any combination thereof.

In a final aspect of the present invention the recombinant vector described herein is used for the production of genetically modified mammalian cells, comprising at least one site for integration of a transgene.

DESCRIPTION OF DRAWINGS

FIG. 3, insert, shows an example of a puromycin-resistant colony generated with two-plasmid transfections, stable eGFP expression was verified by fluorescence microscopy.

DETAILED DESCRIPTION OF THE INVENTION

Figure 1:
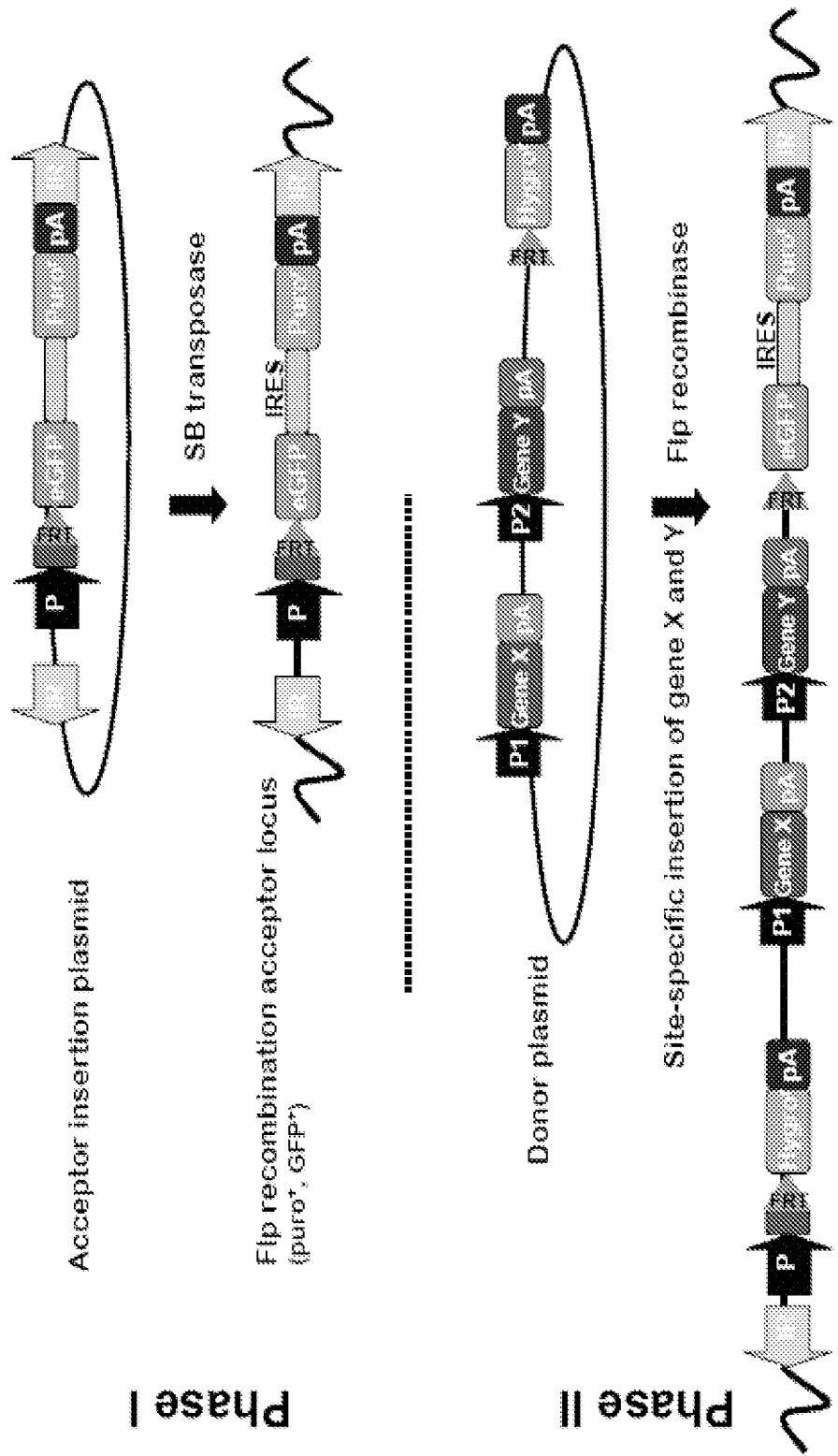
FIG. 1 shows the bi-phased technology of the present invention in which an integrating SB vector, carrying a reporter gene and a selective marker gene, serves as a reporter for continuous gene expression and hence as a target for gene insertion. In a second modification step this vector may serve as a target for insertion of one or more gene expression cassettes in a well-characterized locus.

In the description that follows, a number of terms used in molecular biology are utilized. In order to provide a clear and consistent understanding of the specification and claims, including the scope to be given such terms, the following definitions are provided.

The terms 'transgenic' pig and 'genetically modified' pig are used in identical meaning herein.

The terms 'transgene' and 'gene of interest' are used herein in identical meaning herein.

The term 'recombination substrate' is herein also referred to as 'donor plasmid'.

The term 'DNA transposon tagged genome' refers to a genome in which a DNA transposon based DNA vector construct has been introduced. The introduced DNA transposon-based vector construct is also referred to as the integrated docking vector, for example the integrated SB docking vector (puro+, eGFP+).

IRES is short for internal ribosome entry site, which is a nucleotide sequence that allows for translation initiation in the middle of a messenger RNA (mRNA) sequence as part of the greater process of protein synthesis. Usually, in eukaryotes, translation can only be initiated at the 5' end of the mRNA molecule, since 5' cap recognition is required for the assembly of the initiation complex. IRES mimics the 5' cap structure, and is recognized by the 40S pre-initiation complex. When an IRES segment is located between two reporter open reading frames in a eukaryotic mRNA molecule (a bicistronic mRNA), it can drive translation of the downstream protein coding region independently of the 5'-cap structure bound to the 5' end of the mRNA molecule. In such a setup both proteins are produced in the cell. The first reporter protein located in the first cistron is synthesized by the cap-dependent initiation approach while translation initiation of the second protein is directed by the IRES segment located in the intercistronic spacer region between the two reporter protein coding regions.

Transposons are mobile genetic elements. Transposons are structurally variable, being described as simple or compound, but typically encode a transposition catalyzing enzyme, termed a transposase, flanked by DNA sequences organized in inverted orientations. For a more thorough discussion of the characteristics of transposons, one may consult Mobile Genetic Elements, D. J. Sherratt, Ed., Oxford University Press (1995) and Mobile DNA, D. E. Berg and M. M. Howe, Eds., American Society for Microbiology (1989), Washington, D.C. both of which are specifically incorporated herein by reference.

Recombination Sites

A key feature of the recombination reactions mediated by the above-noted recombination proteins are recognition sequences, often termed "recombination sites," on the DNA molecules participating in the recombination reactions. These recombination sites are discrete sections or segments of DNA on the participating nucleic acid molecules that are recognized and bound by the recombination proteins during recombination. For example, the recombination site for Cre recombinase is loxP which is a 34 base pair sequence comprised of two 13 base pair inverted repeats (serving as the recombinase binding sites) flanking an 8 base pair core sequence. See FIG. 1 of Sauer, B. Curr. Opin. Biotech. 5:521-527 (1994). Other examples of recognition sequences include the attB and attP sequences which are recognized by the recombination protein 1 Int. attB is an approximately 25 base pair sequence containing two 9 base pair core-type Int binding sites and a 7 base pair overlap region, while attP is an approximately 240 base pair sequence containing core-type Int binding sites and arm-type Int binding sites as well as sites for auxiliary proteins integration host factor (IHF), FIS and excisionase (Xis). See Landy, Curr. Opin. Biotech. 3:699-707 (1993).

The term "genetic determinant" is used herein to refer to a single-stranded or double-stranded "polynucleotide molecule" or "nucleic acid" comprising a structural gene of interest. The "genetic determinant" encodes a protein not ordinarily made in appreciable amounts in the target cells. Thus, "genetic determinants" include nucleic acids which are not ordinarily found in the genome of the target cell. "Genetic determinants" also include nucleic acids which are ordinarily found within the genome of the target cell, but is in a form which allows for the expression of proteins which are not ordinarily expressed in the target cells in appreciable amounts. Alternatively, "genetic determinants" may encode a variant or mutant form of a naturally-occurring protein.

The terms "polynucleotide" and "nucleic acid" are used interchangeably, and, when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

As used herein, a nucleotide is a base-sugar-phosphate combination. Nucleotides are monomeric units of a nucleic acid molecule (DNA and RNA). The term nucleotide includes ribonucleoside triphosphates ATP, UTP, CTG, GTP and deoxyribonucleoside triphosphates such as DATP, dCTP, dITP, dUTP, dGTP, dTTP, or derivatives thereof. Such derivatives include, for example, [.alpha.S]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

As used herein, a promoter is an example of a transcriptional regulatory sequence, and is specifically a DNA sequence generally described as the 5'-region of a gene located proximal to the start codon. The transcription of an adjacent DNA segment is initiated at the promoter region.

The term 'recombination site' is a recognition sequence on a nucleic acid molecule participating in an integration/recombination reaction by recombination proteins. Recombination sites are discrete sections or segments of nucleic acid on the participating nucleic acid molecules that are recognized and bound by a site-specific recombination protein during the initial stages of integration or recombination. For example, the recombination site for Cre recombinase is loxP which is a 34 base pair sequence comprised of two 13 base pair inverted repeats (serving as the recombinase binding sites) flanking an 8 base paircore sequence. See FIG. 1 of Sauer, B. Curr. Opin. Biotech. 5:521-527 (1994). Other examples of recognition sequences include the attB, attP, attL, and attR sequences described herein, and mutants, fragments, variants and derivatives thereof, which are recognized by the recombination protein 1 Int and by the auxiliary proteins integration host factor (IHF), FIS and excisionase (Xis). See Landy, Curr. Opin. Biotech. 3:699-707 (1993).

As used herein, a vector is a nucleic acid molecule (preferably DNA) that provides a useful biological or biochemical property to an Insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, selectable markers (ie. selection genes).

Genetic Modification

The present invention pertains to a genetically modified pig, porcine embryo, blastocyst, fetus and/or donor cell wherein the genetically modified genome comprises at least one site for integration of at least one transgene.

It will be appreciated that the invention does not comprise processes for modifying the genetic identity of pigs which are likely to cause them suffering without any substantial medical benefit to man or animal, or animals resulting from such processes.

The present invention also relates to modified pig embryos, blastocysts, donor cells and/or fetuses obtainable by the methods described herein.

The methods for producing the pig model described herein do not encompass a surgical step performed on the pig.

The present invention relates to a genetically modified pig, wherein the genetically modified genome comprises at least one site for integration of at least one transgene. However, the present invention also relates to porcine blastocysts, embryos, fetuses and/or cells (for example cells to be used as donor cells in nuclear transfer) derived from the genetically modified pig the genome of which comprises at least one site for integration of at least one transgene.

Within the scope of the present invention are also genetically modified porcine blastocysts, embryos, fetuses and/or cells, wherein the genetically modified genome comprises at least one site for integration of at least one transgene. Such genetically modified porcine blastocysts, embryos, fetuses and/or cells may be obtained by use of the recombinant target vector, and/or system of the present invention, followed by nuclear transfer as described elsewhere herein.

It is appreciated that the genetically modified pig, porcine blastocysts, embryos, fetuses and/or cells (donor cells and/or cell nucleus) in the genome comprise more than one site for integration of at least one transgene. Thus, the genome comprises two, 3, 4, 5, 6, 7, 8, 9, 10, 15, 20 sites for integration of at least one transgene.

The at least one site for integration of at least one transgene is in a preferred embodiment a recombination site. The at least one site for integration is a heterologous recombination site (nucleic acids), which is not ordinarily found in the genome of the pig, porcine blastocysts, embryos, fetuses and/or cells (donor cells and/or cell nucleus). The present invention takes advantage of the Cre-Lox recombination technology involving the recombination of sequences between lox P sites by the Cre recombinase protein. In another embodiment the vector comprises sequences of site directed recombination technology, namely the involving the recombination of sequences between FRT sites by the Flp (and enhanced Flp, Flpe) recombination enzyme derived from *Saccharomyces cerevisiae*. In yet another embodiment the vector of the present invention takes advantage of the attB/P-ϕC31 recombination technology, wherein the vector comprises attB/P recognition sequences for the ϕC31 recombinase. Thus, the recombination technology used in the present invention may be selected from the group consisting of the Cre-LoxP, Flp-FRT, Flpe-FRT and attB/P-ϕC31 systems.

Accordingly, the at least one site for integration of at least one transgene present in the genome of the pig, porcine blastocysts, embryos, fetuses and/or cells (donor cells and/or cell nucleus) is a recombination site for a recombinase. Non-limiting examples of recombination sites are recombination sites for Flp, Flpe, Flpx9, ϕC32 and/or Cre recombinase. Thus, in one embodiment the at least one site for integration of at least one transgene present in the genome of the pig, porcine blastocysts, embryos, fetuses and/or cells (donor cells and/or cell nucleus) is a recombination site for recombinases selected from the group consisting of Flp, Flpe, Flpx9 and Cre recombinase. In another embodiment the recombination site for recombinases is selected from the group consisting of Flp, Flpe and attB/P. In preferred embodiment the recombination site is for the Flp recombinase. However, in another preferred embodiment the at least one recombination site is for Flpe or Flpx9 recombinase.

Non-limiting examples of the at least one site for integration of at least one transgene present in the genome of the pig, porcine blastocysts, embryos, fetuses and/or cells (donor cells and/or cell nucleus) are FRT, attB, attP, attB/P and Lox P recombination sites. Thus, the at least one site for integration present in the genome of the pig, porcine blastocysts, embryos, fetuses and/or cells (donor cells and/or cell nucleus) is selected from the group consisting of FRT, attB/P and Lox P. It is within the scope of the present invention that the at least one site for integration is any of FRT, attB, attP, attB/P or Lox P, in separate embodiments or in any combination. In a preferred embodiment the at least one site for integration is a FRT site (SEQ ID NO.: 1). In another preferred embodiment the at least one site for integration is a Lox P site for example the wtLoxP (SEQ ID NO.: 2), or the core thereof (SEQ ID NO.: 3), or for example the LoxP257 (SEQ ID NO.: 4), or the core thereof (SEQ ID NO.: 5). In yet another preferred embodiment the at least one site for integration is a full length attB site (SEQ ID NO.: 6, or an attB core site (SEQ ID NO.: 7), or for example an attP site (SEQ ID NO.: 8).

In one embodiment the genome of the genetically modified pig, porcine blastocysts, embryos, fetuses and/or cells (donor cells and/or cell nucleus) comprise at least one selection gene and/or reporter gene. The selection gene is any gene conferring resistance to a drug as described elsewhere herein. In a preferred embodiment the gene is a puromycin resistance gene (SEQ ID NO.: 9). Alternatively, the selection gene is the eGFP gene (SEQ ID NO.: 10).

In another embodiment the genome of the genetically modified pig, porcine blastocysts, embryos, fetuses and/or cells (donor cells and/or cell nucleus) comprise at least one IRES element, for example the IRES element of SEQ ID NO:11.

Furthermore, the genome of the genetically modified pig, porcine blastocysts, embryos, fetuses and/or cells (donor cells and/or cell nucleus) comprises in another embodiment promoter sequences. A number of suitable promoters are listed elsewhere herein. In one preferred embodiment the promoter is a Rous sarcoma virus (RSV) promoter (SEQ ID NO:12), simian virus 40 (SV40) promoter (SEQ ID NO:13), and/or the promoter of ubiquitin (Ubi) (SEQ ID NO:14).

However, in another embodiment the genome of the genetically modified pig, porcine blastocysts, embryos, fetuses and/or cells (donor cells and/or cell nucleus) comprise left inverted repeat and/or right inverted repeat originating from the SB transposon (SEQ ID NO:15).

The pig, porcine blastocysts, embryos, fetuses and/or cells (donor cells and/or cell nucleus) of the present invention further comprise elements of the recombinant target vector as described elsewhere herein. When the recombinant target vector of the present invention is integrated into the genome of the pig, porcine blastocysts, embryos, fetuses and/or cells (donor cells and/or cell nucleus) the recombinant target vector is referred to as the integrated SB docking vector and the genome is referred to as the transposon-tagged genome obtained by integration of the recombinant target vector pSBT/SV40-GFIP.IoxP (SEQ ID NO:16) or part thereof, transcriptional product or part thereof and/or translational product or part thereof, or the pSBT/RSV-GFIP (SEQ ID NO:17) or part thereof, transcriptional product or part thereof and/or translational product or part thereof, or pSBT/SV40-GFIP (SEQ ID NO:18) or part thereof, transcriptional product or part thereof and/or translational product or part thereof, or pSBT/SV40-GFIP.IoxP (SEQ ID NO:19) or part thereof, transcriptional product or part thereof and/or translational product or part thereof.

In one preferred embodiment the at least one site for integration is a recombination site for site-specific transgene insertion. Transposons are sequences of DNA that can move around to different positions within the genome of a single cell and transposons are therefore often referred to as mobile genetic elements. A DNA transposon acts by cut and paste, using a transposase enzyme which binds to single-stranded DNA and incorporates it into genomic DNA. Different types of transposase work in different ways. Some can bind to any part of the DNA molecule, and the target site can therefore be anywhere, while others bind to specific sequences. Transposase makes a staggered cut at the target site producing sticky ends, cuts out the transposon and ligates it into the target site. A DNA polymerase fills in the resulting gaps from the sticky ends and DNA ligase closes the sugar-phosphate backbone. This results in target site duplication and the insertion sites of DNA transposons may be identified by short direct repeats (a staggered cut in the target DNA filled by DNA polymerase) followed by inverted repeats (which are important for the transposon excision by transposase). Thus, in the present context site-specific transgene insertion is characterised by the site in which the transposase has inserted the transposon. The site in which the transposon is inserted may be at a position in the genome which is partially or fully silenced due to for example epigenetic modifications of the heterochromatin of the host. In a preferred embodiment of the present invention the at least one site for integration is a recombination site for site-specific transgene insertion, wherein the at least one site for integration is positioned in the genome such that the transgene is expressed.

The present invention also relates to genetically modified pigs porcine blastocysts, embryos, fetuses and/or cells (donor cells and/or cell nucleus) comprising at least one site for integration and further comprising at least one transgene. Preferably, the at least one transgene is inserted into the at least one site for integration that is into the at least one recombination site.

The transgene of the present invention may be any transgene. In one embodiment the transgenes are disease-causing genes and/or genes which modify genes present in the pig, embryo, blastocyst, fetus and/or cell thereof, causing the expression of the endogenous genes to be altered. Such modifications give rise to animal models for studying a number of phenotypes of disease.

To identify loci that support stable ubiquitous expression and facilitate site-specific transgene insertion into such sites, a novel two-step gene insertion protocol for modification of primary porcine fibroblasts and generation of cloned transgenic pigs is presented here.

The insertion protocol is based on a recombinant target vector comprising a DNA transposon-based construct comprising a bicistronic gene cassette comprising (i) a recombination site and (ii) an IRES-driven selection gene.

Recombinant Target Vector

One aspect the present invention relates to a recombinant target vector comprising a DNA transposon based construct comprising a bicistronic gene cassette comprising (i) at least one recombination site and ii) an IRES-driven selection gene or part thereof. The recombinant target vector can be integrated into the genome of a pig, embryo, blastocyst, fetus and/or cells thereof and serve as a target for the insertion of a transgene positioned on a donor plasmid.

The DNA transposon-based construct may be any construct in which any DNA transposon or part thereof is present. This allows the precise manipulation of an organism's DNA under controlled conditions in vivo. The DNA transposon of the present invention is selected from the group consisting of the Sleeping Beauty (SB) transposon, Frog Prince (FP) transposon, Piggybac transposon, Tol2 transposon, Himar 1 transposon. In another embodiment the DNA transposon is selected from the group constisting of the SB transposon, the FP transposon and Piggybac transposon, or from the group consisting of the FP transposon, the Piggybac transposon, the Tol2 transposon and the Himar 1 transposon. However, the DNA transposon may be selected from any of the SB transposson, the FP transposon and Piggybac transposon, or from the group consisting of the FP transposon, the Piggybac transposon, the Tol2 transposon and the Himar 1 transposon. In the present invention in one embodiment the DNA transposon of the DNA transposon-based construct is the DNA transposon construct known as the Sleeping Beauty (SB) DNA transposon vector.

The vector of the present invention employs a site-specific recombination technology, which involves recombination sequences between binding sites for recombinases. When cells comprise site-specific integration sites (or recombination sites) for recombinases, a reciprocal recombination event occurs in the presence of a recombinase between the integration sites. The double stranded DNA is cut at both recombination sites and then subsequently ligated. The consequences of recombination depend on the orientation of the site-specific recombination sites. When two recombination sites are present on one segment of DNA (eg. on one chromosome arm), inverted recombination sites will cause an inversion, while a direct repeat of recombination sites will result in a deletion event. In the case where the two recombination sites are present on two different segments of DNA, a translocation event takes place.

In one embodiment the vector takes advantage of the Cre-Lox recombination technology involving the recombination of sequences between lox P sites by the Cre recombinase protein. In another embodiment the vector comprises sequences of site directed recombination technology, namely the involving the recombination of sequences between FRT sites by the Flp recombination enzyme derived from *Saccharomyces cerevisiae*. In yet another embodiment the vector of the present invention takes advantage of the attB/P-φC31 recombination technology, wherein the vector comprises attB/P recognition sequences for the φC31 recombinase. Thus, the recombination technology used in the present invention may be selected from the group consisting of the Cre-LoxP, Flp-FRT, Flpe-FRT and attB/P/φC31 systems.

Accordingly, the vector of the present invention harbors the recognition sequence selected from the group consisting of LoxP, FRT and attB/P.

However, the examples of recombination systems and recognition sequences listed above are non-limiting examples, as any recombination system functioning as disclosed herein may be used. In one preferred embodiment the vector harbors Lox P recombination sites for Cre, or even more preferred the vector harbors FRT recognition sites for Flp.

Selection and Reporter Genes

The selection gene present in the recombinant target vector and/or the genome of the pig, porcine blastocysts, embryos, fetuses and/or cells (donor cells and/or cell nucleus) of the present invention is not limited to any particular selection gene. In the present context the term 'selection gene' thus comprises reporter genes such as any reporter genes that can be used to evaluate whether transposition has occurred. For example the reporter gene is selected from the group consisting of the enhanced green fluorescent protein (eGFP), lac Z, dsRed, enhanced yellow fluorescent protein (eYFP), enhanced cyan fluorescent protein (eCFP), enhanced blue fluorescent protein (eBFP) and the human alpha-1-antitrypsin (hAAT).

The selection gene may be any gene suitable for selecting cells harbouring the constructs of the present invention. Typically the selection gene is a gene that confers resistance to antibiotics or drugs. Examples of such selection genes is the puromycin resistance gene (Puro), the tetracycline resistance gene, the streptomycin resistance gene, the hygromycin B resistance gene (Hygro), the zeocin resistance gene (zeo), the neomycin resistance gene (neo), and the blasticidin resistance gene (Bst). Therefore, the selection gene of the present invention is selected from the group consisting of puromycin resistance gene (Puro), the tetracycline resistance gene, the streptomycin resistance gene, the hygromycin B resistance gene (Hygro), the zeocin resistance gene (zeo), the neomycin resistance gene (neo) and the blasticidin resistance gene (Bst). In a preferred embodiment the selection gene is selected from the group consisting of puromycin resistance gene (Puro), the hygromycin B resistance gene (Hygro), the zeocin resistance gene (zeo), the neomycin resistance gene (neo) and the blasticidin resistance gene (Bst). It is appreciated that the resistance gene is selected from any of puromycin resistance gene (Puro), the tetracycline resistance gene, the streptomycin resistance gene, the hygromycin B resistance gene (Hygro), the zeocin resistance gene (zeo), the neomycin resistance gene (neo) or the blasticidin resistance gene (Bst).

The selection gene is in one embodiment driven by an IRES element.

In a preferred embodiment the IRES-driven selection gene of the recombinant target vector and/or the genome of the pig, porcine blastocysts, embryos, fetuses and/or cells (donor cells and/or cell nucleus) of the present invention confers resistance to a drug, preferably puromycin.

Position of Selection Genes

The recombination site of the recombinant target vector and/or the genome of the pig, porcine blastocysts, embryos, fetuses and/or cells (donor cells and/or cell nucleus) of the present invention may be embedded in the coding sequence of a selection gene which allows for detecting whether a transposition has occurred. According to the present invention the recombination site present in the vector is embedded in the coding sequence of any suitable reporter gene. The FRT, LoxP and/or attB/P recognition sites may thus be embedded in any of non-limiting examples of reporter genes listed herein.

For example, the FRT is embedded in the coding sequence of eGFP, lac Z, dsRed, eYFP, eCFP, eBFP or hAAT. Similarly, the LoxP is embedded in the coding sequence of eGFP, lac Z, dsRed, eYFP, eCFP, eBFP or hAAT. Moreover, the attB/P is embedded in the coding sequence of eGFP, lac Z, dsRed, eYFP, eCFP, eBFP or hAAT. In a preferred embodiment the recombination site is embedded in the coding sequence of eGFP.

The recombination site may thus be embedded in a promoter driven fusion variant of the selection gene. Thus, in one embodiment the recombination site is embedded in a SV40 promoter driven fusion variant of the selection gene. In one preferred embodiment the FRT site is embedded in a SV40 promoter driven fusion variant of eGFP. In another preferred embodiment wherein said FRT recombination site is embedded in a ubiquitin promoter driven fusion variant of eGFP. In yet a preferred embodiment the FRT site is embedded in a RSV promoter driven fusion variant of eGFP. However, any promoter suitable for conferring expression of a selection gene may be used according to the present invention. Non-limiting examples of such promoters are the promoter of Rous sarcoma virus (RSV), promoter of cytomegalo virus (CMV), the promoter of simian virus 40 (SV40), the ubquitin promoter (Ubi), the promoter of the human elongation factor 1α (EF1 α), the promoter of the human phosphoglycerate kinase (PGK) or the promoter of the inducible CMV Tet On/Off. Thus, the promoter is selected from the group consisting of the promoter of Rous sarcoma virus (RSV), promoter of cytomegalo virus (CMV), the promoter of simian virus 40 (SV40), the promoter of the human elongation factor 1α (EF1 α), the promoter of the human phosphoglycerate kinase (PGK) and the promoter of the inducible CMV TetOn/Off. In one preferred embodiment the promoter is selected from the group consisting of the SV40, CMV and PGK promoter.

However, according to the present invention, the promoter may be selected from any of the promoter of Rous sarcoma virus (RSV), promoter of the cytomegalo virus (CMV), the promoter of simian virus 40 (SV40), the promoter of the human elongation factor 1α (EF1 α), the promoter of the human phosphoglycerate kinase (PGK) or the promoter of the inducible CMV Tet On/Off. In a preferred embodiment the promoter is the RSV promoter. In another preferred embodiment the promoter is the Ubi promoter. In yet another preferred embodiment the promoter is the SV40 promoter.

IRES

An internal ribosome entry site, abbreviated IRES, is a nucleotide sequence that allows for translation initiation in the middle of a messenger RNA (mRNA) sequence as part of the greater process of protein synthesis. Usually, in eukaryotes, translation can only be initiated at the 5' end of the mRNA molecule, since 5' cap recognition is required for the assembly of the initiation complex. IRES mimics the 5' cap structure, and is recognized by the 40S pre-initiation complex. When an IRES segment is located between two reporter open reading frames in a eukaryotic mRNA molecule (a bicistronic mRNA), it can drive translation of the downstream protein coding region independently of the 5'-cap structure bound to the 5' end of the mRNA molecule. In such a setup both proteins are produced in the cell. The first reporter protein located in the first cistron is synthesized by the cap-dependent initiation approach while translation initiation of the second protein is directed by the IRES segment located in the intercistronic spacer region between the two reporter protein coding regions.

The IRES of the present invention is any IRES capable of driving the expression of a selection gene independently of the 5' cap structure bound to the 5' end of the mRNA molecule. Non-limiting examples of IRES elements are IRES from poliovirus, rhinovirus, encephalomyocarditis virus (EMCV), Hepatitis A virus, hepatitis C virus, Friend murine leukaemia virus, Moloney murine leukaemia virus, Rous sarcoma virus and human immunodeficiency virus. In a preferred embodiment the IRES of the present invention originates from EMCV.

The internal ribosome entry site, IRES, -driven selection gene is similarly not limited to any particular selection gene. In preferred embodiments the selection gene are genes conferring resistance to antibiotics or drugs, such as puromycin, tetracycline, streptomycin or hygromycin resistance genes, or the enhanced green fluorescent protein (eGFP) gene, red fluorescent protein genes or the like.

The recombinant vector construct may also comprise at least one recombination site for Cre recombinase and/or φC31 recombinase. The at least one site for Cre recombinase may be located as disclosed in the examples herein. In a preferred embodiment the recognition site for Cre recombinase is located between the poly A sequence and the lower inverted repeat of the vector.

Embodiments of the present invention are vectors such as a Sleeping Beauty DNA transposon-based vector which in its integrated form as a integrated SB docking vector serves as a target for Flp recombinase-based gene insertion, a Cre recombinase-based gene insertion or a φC31 recombinase-based gene insertion.

In a first step, the vector of the present invention is transferred by cut-and-paste transposition into the genome of a mammalian cell, for example a somatic cell and therefore is not flanked by bacteria-derived plasmid sequences. By determining the vector-derived reporter gene expression in the target cell such as a mammalian cell, embryos or animals created by for example hand-made cloning, microinjection or other cloning techniques, it is possible to characterize individual animals with a desired expression profile. In a second step, target cells having desired expression profiles are propagated, and/or for example primary fibroblasts are isolated from animals as described above. The target site for the recombinase, such as for Flp, Cre and/or φC31 recombinase located within the integrated vector of the present invention, is subsequently utilized for site-specific gene insertion, producing a cell in which a gene of interest is inserted into a location in the target cell for which the expression profile is known. Subsequently, such cells harbouring the at least one gene of interest may form the basis for propagation of a cell line. In addition, the described cell may be used for a second round of cloning, such as for the production of an animal with a desired phenotype employing said cell in a second round of hand-made cloning, microinjection or other cloning techniques.

The vector of the present invention may further comprise at least one insulator element. The insulator element serves to stabilise the gene expression of the gene of interest when integrated into the genome of a target cell, and thus avoid potential epigenetic silencing. In one embodiment of the present invention the at least one insulator element is 1.2 kb of the cHS4 (chicken DNase hypersensitive site 4-derived insulator element). The at least one insulator element is flanking the promoter-selection gene fusion. In one preferred embodiment two insulator elements are present in the vector.

The present invention pertains to a mammalian cell comprising a transposon tagged genome containing at least one recombination target site for site-specific gene integration of at least one gene of interest. In one preferred embodiment the at least one recombination site is the Flp recombination target site for site-specific gene insertion or integration.

In yet a further aspect the present invention relates to a mammalian cell comprising at least one gene of interest obtained by use of the bi-phased system of the present invention.

The mammalian cell comprises a DNA transposon tagged genome using the recombinant target vector of the present invention and/or using the bi-phased system of the present invention.

The mammalian cell as referred to herein is not confined to any particular cell type. The mammalian cell may thus be immune cells such as T-cells, epithelial cells, endothelial cells, fibroblast cells, cells from lung, heart, liver or neuronal cells. The mammalian cell may be of human, porcine, murine, canine or feline origin. In particular embodiments of the present invention the mammalian cell is immortal antitumorigenic cytotoxic T cells of human origin. In a preferred embodiment, the mammalian cell is a somatic cell, preferably of porcine origin. In a preferred embodiment the somatic cell is a porcine fibroblast cell, for example a primary somatic cell, or a porcine neonatal fibroblast cell.

Figure 2:
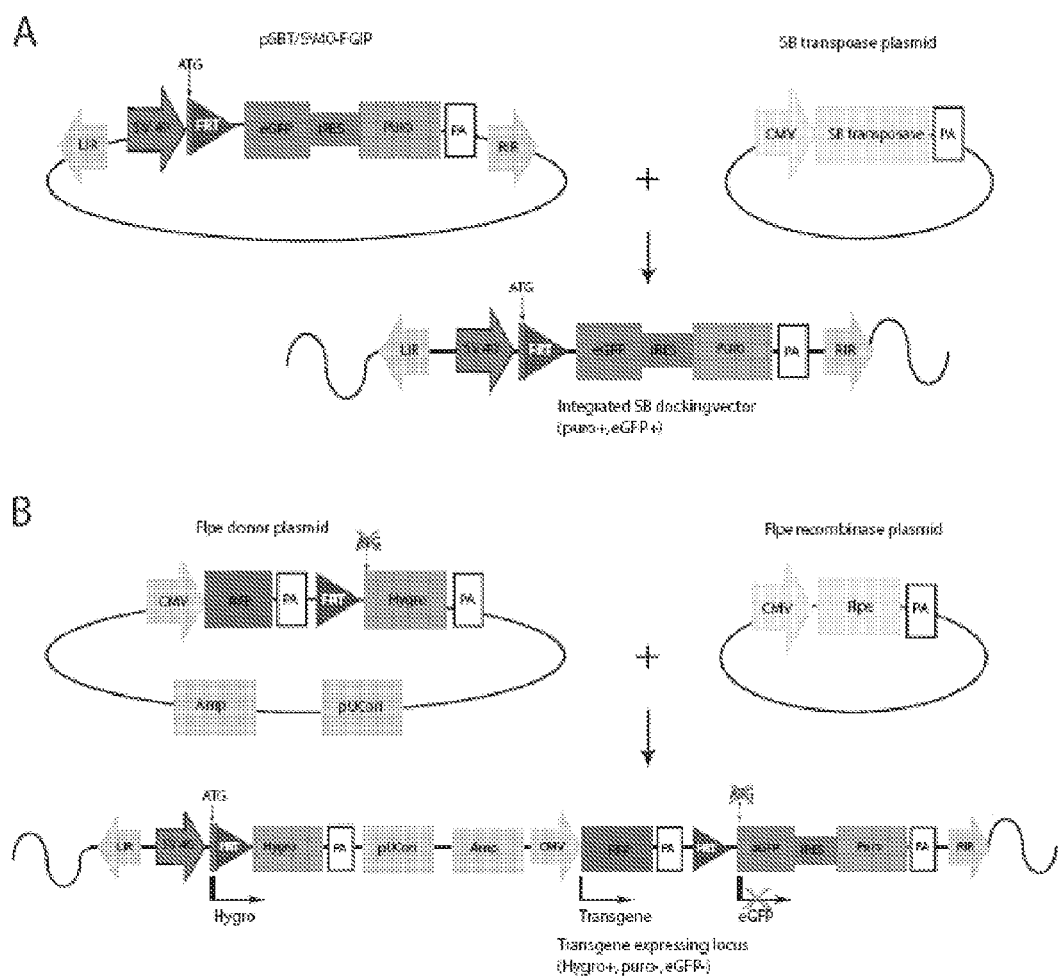
FIG. 2 shows a Sleeping Beauty docking vector system for controlled porcine transgenesis by Flp-directed gene insertion. A) Schematic description of the SB transposon plasmid used in the first step of transgenesis. The pSBT/SV40-FGIP plasmid includes a gene cassette flanked by LIR and RIR elements which enable transposition of the gene insert in the presence of SB transposase. The gene cassette includes the SV40 promoter driving the expression of a transcript encoding eGFP and the puromycin resistance gene. Co-expression of the proteins is achieved by the presence of an internal ribosomal entry site (IRES) after the eGFP coding region. In the 5'-region of the eGFP gene (immediately flanking the start codon) is inserted an FRT site that allows Flp-mediated recombination. After transposase-mediated integration into the host genome, the gene cassette represents an acceptor locus for further transgenesis. The FRT site is located just 3' of the start codon of eGFP and thus enable a controlled recombination event that separates this start codon from the rest of the eGFP gene and, accordingly, abolishes eGFP translation. B) Schematic representation of the Flp donor plasmid, used in the second step of transgenesis, and the result of Flp-directed transgenesis. The Flp donor plasmid contains the CMV promoter which controls the expression of a transcript encoding the DsRed protein which is used as a marker. In addition, the donor plasmid includes a promoter-free gene cassette including the hygromycin B resistance gene and a polyadenylation signal. The 5"-region of the hygromycin resistance gene is modified to include a FRT recombination site and to lack a translational start codon. The lower part of the figure illustrates Flp-mediated recombination for insertion of the donor sequence into the acceptor locus.

The gene of interest is prior to recombination into the integrated vector (integrated docking vector) of the present invention located on a substrate for the recombinases. The substrates are characterised by the presence of a fusion between at least one recognition site and a gene of interest for example a selection gene and/or a gene conferring the establishment of a desired phenotype or genotype of the cell. In one preferred embodiment the substrate comprises a promoter driving the expression of a gene of interest followed by a polydenylation signal, at least one recombination site and a selection gene without a functional ATG start codon followed by a polyadenylation sequence. One example is the Flpe donor plasmid shown in FIG. 2. The selection gene may be selected from the group of selection genes listed above and similarly the recognition site may be selected from the recognition sites as described elsewhere herein. The fusion of the at least one recognition site and selection gene may be present in a DNA construct, such as a plasmid, an in vitro-generated plasmid-derived minicircle and/or lentiviral DNA circles. Non-limiting examples of such DNA constructs are for example plasmids containing FRT-hygro fusion cassette (SEQ ID NO:20), or in-vitro generated plasmid-derived minicircles containing a FRT-hygro cassette, or lentiviral DNA circles containing a FRT-hygro cassette.

Lentiviral DNA circles are unintegrated lentiviral DNA in the form of so-called 2 LTR circles or 1 LTR circles. In the present invention the lentiviral DNA circles result from integration defective lentiviral vectors. In one embodiment of the present invention the lentiviral DNA originates from lentiviruses such as human immunodeficiency virus 1 or simian immunodeficiency virus 1.

The introduced gene or transgene, transcriptional and/or translational product or part thereof may originate from any species, including bacteria, pig, human, mouse, rat, yeast, invertebrates, or plants. Regulatory sequences of the transgene may drive ubiquitous or inducible or tissue- and/or time-specific expression and may also originate from any species including pig, human, mouse, rat, yeast, invertebrates, or plants.

Thus, a further aspect of the present invention relates to a bi-phase system for site-directed integration of genes of interest. The system comprises the recombinant target vector of the present invention and a recombination substrate. The recombination substrate comprises a fusion of at least one recognition site (recombination site) for a recombinase and a gene of interest. The recombination substrate is present in a plasmid, an in vitro generated plasmid-derived minicircle and/or a lentiviral circle as described elsewhere herein.

In a preferred embodiment for producing genetically modified pigs the mammalian cell is a porcine primary fibroblast.

Primary fibroblasts are fibroblasts derived directly from excised skin as explants.

It will be appreciated that the invention does not comprise processes for modifying the genetic identity of pigs which are likely to cause them suffering without any substantial medical benefit to man or animal, or animals resulting from such processes.

The present invention also relates to genetically modified pig embryos obtainable by the methods described herein.

The methods for producing the pig model described herein do not encompass a surgical step performed on the pig.

Sequence Identity

Functional equivalents and variants are used interchangeably herein. In one preferred embodiment of the invention there is also provided variants of the genes listed herein, the recombination sites, selection genes, transposons, recombinases, promoters as listed herein. When being polypeptides, variants are determined on the basis of their degree of identity or their homology with a predetermined amino acid sequence of the present invention, or, when the variant is a fragment, a fragment of any of the aforementioned amino acid sequences, respectively.

Accordingly, variants preferably have at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparision; a predetermined sequence may be a subset of a larger sequence, for example, as a segment of a full-length DNA or gene sequence given in a sequence listing, or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length modified porcine or human Ps1 sequence, or porcine or human APP sequence polynucleotide sequence illustrated herein.

Sequence identity is determined in one embodiment by utilising fragments of peptides comprising at least 25 contiguous amino acids and having an amino acid sequence which is at least 80%, such as 85%, for example 90%, such as 95%, for example 96%, such as 97%, for example 98%, such as 99% identical to the amino acid sequence of for example the products of selection genes, wherein the percent identity is determined with the algorithm GAP, BESTFIT, or FASTA in the Wisconsin Genetics Software Package Release 7.0, using default gap weights.

Conservative Amino Acid Substitutions:

Substitutions within the groups of amino acids, shown below, are considered conservative amino acid substitutions. Substitutions between the different groups of amino acids are considered non-conservative amino acid substitutions.

P, A, G, S, T (neutral, weakly hydrophobic)
Q, N, E, D, B, Z (hydrophilic, acid amine)
H, K, R (hydrophilic, basic)
F, Y, W (hydrophobic, aromatic)
L, I, V, M (hydrophobic)
C (cross-link forming)

By the term "transcriptional or translational products" is meant herein products of gene transcription, such as a RNA transcript, for example an unspliced RNA transcript, a mRNA transcript and said mRNA transcript splicing products, and products of gene translation, such as polypeptide(s) translated from any of the gene mRNA transcripts and various products of post-translational processing of said polypeptides, such as the products of post-translational proteolytic processing of the polypeptide(s) or products of various post-translational modifications of said polypeptide(s).

As used herein, the term "transcriptional product of the gene" refers to a pre-messenger RNA molecule, pre-mRNA, that contains the same sequence information (albeit that U nucleotides replace T nucleotides) as the gene, or mature messenger RNA molecule, mRNA, which was produced due to splicing of the pre-mRNA, and is a template for translation of genetic information of the gene into a protein.

Pigs

The present invention relates to a genetically modified pig, wherein the genetically modified genome comprises at least one site for integration of at least one transgene. The pig of the present invention may be any pig.

In one embodiment of the present invention the pig or porcine cells originate from a wild pig. In another embodiment the pig is the domestic pig, Sus scrofa, such as S. domesticus. In yet another embodiment the invention relates to mini pigs, as well as to inbred pigs. The pig can be selected e.g. from the group consisting of Landrace, Yorkshire, Hampshire, Duroc, Chinese Meishan, Berkshire and Piêtrain, such as the group consisting of Landrace, Yorkshire, Hampshire and Duroc, for example the group consisting of Landrace, Duroc and Chinese Meishan, such as the group consisting of Berkshire, Piêtrain, Landrace and Chinese Meishan, for example the group consisting of Landrace and Chinese Meishan. In one embodiment, the pig is not a mini-pig.

In another embodiment of the present invention the pig is a mini-pig and the mini-pig is preferably selected from the group consisting of Goettingen, Yucatan, Bama Xiang Zhu, Wuzhishan and Xi Shuang Banna. Thus, the present invention relates to any of Goettingen, Yucatan, Bama Xiang Zhu, Wuzhishan and Xi Shuang Banna separately or in any combination.

Due to its size and weight of about 200 kg the domestic pig is not easily handled in a laboratory setting. A preferred alternative to the domestic pig is the Goettingen (Göttingen) mini-pig that weighs about 30 kg. Therefore, a preferred embodiment the pig of the present invention is the Goettingen mini pig.

Methods for Producing the Mammalian Cell of the Present Invention

The present invention also relates to a method for producing a mammalian cell comprising a SB tagged genome containing a Flp or Flpe recombination target site for site-specific gene insertion. The method for producing a mammalian cell comprises a DNA transposon tagged genome comprising a recombination target site for site-specific gene insertion comprises the steps of a) providing a mammalian cell, b) transfecting the cell of a) with a plasmid expressing a transposase and a recombinant vector comprising a DNA transposon-based construct carrying a bicistronic gene cassette comprising (i) a recombination site and ii) an IRES-driven selection gene, c) selecting DNA transposon tagged cells. The recombinant vector may comprise any DNA-transposon as described elsewhere herein. In one embodiment the recombinant target vector comprises a DNA transposon in the form of a Sleeping Beauty transposon. In one embodiment the recombinant target vector comprising a DNA transposon construct and a bicistronic gene cassette comprising (i) a FRT recombination site and ii) an IRES-driven selection gene, such as for example a puromycin resistance gene. Thus, the method comprises a) providing a mammalian cell, b) transfecting the cell of a) with a plasmid expressing a transposase and a recombinant target vector comprising a DNA transposon construct and a bicistronic gene cassette comprising (i) a FRT recombination site and ii) an IRES-driven selection gene, c) selecting SB tagged cells.

The transposon tagged cells, for example Sleeping Beauty tagged cells are selected by antibiotics or any agent allowing for the selection of transposon tagged cells. A number of selection agents are described elsewhere herein. A person skilled in the art will appreciate which antibiotic to use given that a specific antibiotic resistance gene is present in the transposon tagged cells. One example is the use of puromycin as selection agent, given that the puromycin resistance gene is present in the transposon tagged cell.

As described elsewhere herein the mammalian cell may be any cell. In one embodiment in which the mammalian cell is subsequently to be used for producing a genetically modified pig by nuclear transfer according to the hand-made protocol as described herein, the mammalian cell is preferably a porcine cell, a fibroblast and most preferred a porcine primary fibroblast or a neonatal porcine fibroblast.

It is appreciated that a desired transgene may be integrated directly into the at least one site for integration present in the genome of the cell. However, the cell in which the genome carries the at least one site for integration is in another embodiment used as a donor cell for the production of a genetically modified pig by for example microinjection of the donor cell or nucleus thereof into a oocyte or by for example somatic nuclear transfer. In a preferred embodiment the donor cell or the nucleus thereof is used for the production of a genetically modified pig by somatic nuclear transfer using the procedure as described elsewhere herein.

The transgene or gene of interest to be integrated in the targeted cells of the present invention is not limited to any particular gene. In one embodiment the gene to be integrated is a disease-causing gene which results in the formation of a genetically modified pig, embryo, blastocyst, fetus and/or donor cell displaying a phenotype of interest.

The integration of the transgene into the at least one site for integration present in the genome of the cell is employed by transfection into the cell of plasmid DNA containing the gene of interest and also a FRT sites, and a plasmid expressing the Flp-recombinase used to support integration at the FRT sites. In another preferred embodiment the integration of the transgene into the at least one site for integration present in the genome of the cell is employed by transfection into the cell of plasmid DNA containing the gene of interest and also a FRT sites, and a plasmid expressing the Flpe-recombinase used to support integration at the FRT sites.

Methods for Producing the Genetically Modified Pig of the Present Invention

The genetically modified pig, porcine embryo, blastocyst, fetus and/or donor cell of the present invention may be produced using any technique in which modified genetic material is transferred from at donor cell to a host cell, such as an enucleated oocyte. A number of techniques exist such as introducing genetic material from a genetically modified somatic cell into an enucleated oocyte by for example microinjection or by nuclear transfer. The present invention provides improved procedures for cloning pigs by nuclear transfer which refers to the introduction of a full complement of nuclear DNA from one cell to an enucleated cell.

In cloning, the transfer of the nucleus of a somatic (body) cell or somatic cell into an egg cell (oocyte) which has had its own nucleus removed (denucleated or enucleated) is called somatic cell nuclear transfer. The new individual will develop from this reconstructed embryo and be genetically identical to the donor of the somatic cell. In the present invention a genetically modified pig, porcine embryo, blastocyst, fetus and/or donor cell is obtainable by somatic cell nuclear transfer comprising the steps of a) establishing at least one oocyte having at least a part of a modified zona pellucida, b) separating the oocyte into at least two parts obtaining an oocyte and at least one cytoplast, c) establishing a donor cell or cell nucleus having desired genetic properties, d) fusing at least one cytoplast with the donor cell or membrane surrounded cell nucleus, e) obtaining a reconstructed embryo f) activating the reconstructed embryo to form an embryo; culturing said embryo; and g) transferring said genetically modified embryo to a host mammal such that the embryo develops into a genetically modified fetus, wherein said genetically modified embryo obtainable by nuclear transfer comprises steps a) to g) or f); wherein said genetically modified blastocyst obtainable by nuclear transfer comprises steps a) to f) or g); wherein said genetically modified fetus obtainable by nuclear transfer comprises steps a) to g.

However, the present invention also relates to a method for producing a transgenic pig, porcine embryo, blastocyst, fetus and/or donor cell comprising the steps of a) establishing at least one oocyte, b) separating the oocyte into at least three parts obtaining at least two cytoplasts, c) establishing a donor cell or cell nucleus having desired genetic properties, d) fusing at least one cytoplast with the donor cell or membrane surrounded cell nucleus, e) obtaining a reconstructed embryo, f) activating the reconstructed embryo to form an embryo; culturing said embryo; and g) transferring said genetically modified embryo to a host mammal such that the embryo develops into a genetically modified fetus, wherein said genetically modified embryo obtainable by nuclear transfer comprises steps a) to g) or f); wherein said genetically modified blastocyst obtainable by nuclear transfer comprises steps a) to f) or g); wherein said genetically modified fetus obtainable by nuclear transfer comprises steps a) to g.

Furthermore, the present invention relates to a method for producing a transgenic pig, porcine embryo, blastocyst, fetus and/or donor cell comprising the steps of a) establishing at least one oocyte, b) separating the oocyte into at least three parts obtaining at least two cytoplasts, c) establishing a donor cell or cell nucleus having desired genetic properties, wherein the donor cell or cell nucleus is established from a genetically modified pig, porcine embryo, blastocyst, fetus and/or donor cell carrying in its genome at least one site for integration of at least one transgene, d) providing a transgene and integrating said transgene into the donor cell of c), d) fusing at least one cytoplast with the donor cell or membrane surrounded cell nucleus, e) obtaining a reconstructed embryo, f) activating the reconstructed embryo to form an embryo; culturing said embryo; and g) transferring said genetically modified embryo to a host mammal such that the embryo develops into a genetically modified fetus, wherein said genetically modified embryo obtainable by nuclear transfer comprises steps a) to g) or f); wherein said genetically modified blastocyst obtainable by nuclear transfer comprises steps a) to f) or g); wherein said genetically modified fetus obtainable by nuclear transfer comprises steps a) to g.

It is appreciated that the genetic determinant in one embodiment is the at least one heterologous site for integration of at least one transgene. Preferably the heterologous step for integration is a recombination site for a recombinase as described in detail elsewhere herein.

The various parameters are described in detail below.

Oocyte

The term 'oocyte' according to the present invention means an immature female reproductive cell, one that has not completed the maturing process to form an ovum (gamete). In the present invention an enucleated oocyte is the recipient cell in the nuclear transfer process.

The oocytes according to the present invention are isolated from oviducts and/or ovaries of a mammal. Normally, oocytes are retrieved from deceased pigs, although they may be isolated also from either oviducts and/or ovaries of live pigs. In one embodiment the oocytes are isolated by oviductal recovery procedures or transvaginal recovery methods. In a preferred embodiment the oocytes are isolated by aspiration. Oocytes are typically matured in a variety of media known to a person skilled in the art prior to enucleation. The oocytes can also be isolated from the ovaries of a recently sacrificed animal or when the ovary has been frozen and/or thawed. Preferably, the oocytes are freshly isolated from the oviducts.

Oocytes or cytoplasts may also be cryopreserved before use. While it will be appreciated by those skilled in the art that freshly isolated and matured oocytes are preferred, it will also be appreciated that it is possible to cryopreserve the oocytes after harvesting or after maturation. If cryopreserved oocytes are utilised then these must be initially thawed before placing the oocytes in maturation medium. Methods of thawing cryopreserved materials such that they are active after the thawing process are well-known to those of ordinary skill in the art. However, in general, cryopreservation of oocytes and cytoplasts is a very demanding procedure, and it is especially difficult in pigs, because of the above mentioned general fragility of pig oocytes and cytoplasts, and because of the high lipid content that makes them very sensitive to chilling injury (i.e. injury that occurs between +15 and +5° C. during the cooling and warming procedure).

In another embodiment, mature (metaphase II) oocytes that have been matured in vivo, may be harvested and used in the nuclear transfer methods disclosed herein. Essentially, mature metaphase II oocytes are collected surgically from either nonsuperovulated or superovulated pigs 35 to 48 hours past the onset of estrus or past the injection of human chorionic gonadotropin (hCG) or similar hormone.

Where oocytes have been cultured in vitro, cumulus cells that are surrounding the oocytes in vivo may have accumulated may be removed to provide oocytes that are at a more suitable stage of maturation for enucleation. Cumulus cells may be removed by pipetting or vortexing, for example, in the presence of in the range of 0.1 to 5% hyaluronidase, such as in the range of 0.2 to 5% hyaluronidase, for example in the range of 0.5 to 5% hyaluronidase, such as in the range of 0.2 to 3% hyaluronidase, for example in the range of 0.5 to 3% hyaluronidase, such as in the range of 0.5 to 2% hyaluronidase, for example in the range of 0.5 to 1% hyaluronidase, such as 0.5% hyaluronidase.

The first step in the preferred methods involves the isolation of a recipient oocyte from a suitable pig. In this regard, the oocyte may be obtained from any pig source and at any stage of maturation.

The stage of maturation of the oocyte at enucleation and nuclear transfer has been reported to be of significance for the success of nuclear transfer methods. Immature (prophase I) oocytes from pig ovaries are often harvested by aspiration. In order to employ techniques such as genetic engineering, nuclear transfer and cloning, such harvested oocytes are preferably matured in vitro before the oocyte cells may be used as recipient cells for nuclear transfer.

Preferably, successful pig embryo cloning uses the metaphase II stage oocyte as the recipient oocyte because it is believed that at this stage of maturation the oocyte can be or is sufficiently activated to treat the introduced nucleus as if it were a fertilising sperm. However, the present invention relates to any maturation stage of the oocyte which is suitable for carrying out somatic cell nuclear transfer, embryos, blastocysts, and/or transgenic pigs obtainable by the method of somatic cell nuclear transfer of the present invention.

The in vitro maturation of oocytes usually takes place in a maturation medium until the oocyte has reached the metaphase II stage or has extruded the first polar body. The time it takes for an immature oocyte to reach maturation is called the maturation period.

In a preferred embodiment of the present invention the oocyte is from sow or gilt, preferably from a sow.

The donor (somatic cell or nucleus of somatic cell) and recipient (cytoplast) involved in the cell nuclear transfer method according to the present invention is a pig. Likewise, reconstructed embryos may be implanted in a pig according to the present invention. The different pigs suitable as donor, recipient or foster mother are described elsewhere herein.

The donor pig according to the present invention may be female, or male. The age of the pig can be any age such as an adult, or for example a fetus.

Embryo

According to the present invention a reconstructed embryo (i.e. single cell embryo) contains the genetic material of the donor cell. Subsequently, the reconstructed embryo divides progressively into a multi-cell embryo after the onset of mitosis. In vitro the onset of mitosis is typically induced by activation as described herein.

In the present invention the term 'embryo' also refers to reconstructed embryos which are embryos formed after the process of nuclear transfer after the onset of mitosis by activation. Reconstructed embryos are cultured in vitro.

When the embryo contains about 12-16 cells, it is called a "morula". Subsequently, the embryo divides further and many cells are formed, and a fluid-filled cystic cavity within its center, blastocoele cavity. At this stage, the embryo is called a "blastocyst". The developmental stage of the "fertilized" oocyte at the time it is ready to implant; formed from the morula and consists of an inner cell mass, an internal cavity, and an outer layer of cells called trophectodermal cells.

The blastocyst according to the present invention may be implanted into the uterus of a host mammal, in particular a pig, preferably a Goettingen minipig and continues to grow into a fetus and then an animal.

In the methods provided herein for producing genetically modified or transgenic non-human mammal, for cloning a non-human mammal, for culturing a reconstructed embryo, and/or for cryopreservation of a pig embryo, the embryo may be cultured in vitro. The embryo may for example be cultured in sequential culture. It will be appreciated that the embryo may be a normal embryo, or a reconstructed embryo as defined elsewhere herein.

The present invention thus relates to a modified porcine embryo, blastocyst and/or fetus derived from the genetically modified pig model as disclosed herein and/or the modified porcine embryo, wherein the genetically modified genome comprises at least one site for integration of at least one transgene.

Cytoplast

An oocyte or a part of an oocyte from which the nucleus has been removed.

Donor Cell

By the term 'donor cell' of the present invention is meant somatic cell and/or cells derived from the germ line.

By the term 'somatic cell' of the present invention is meant any (body) cell from an animal at any stage of development. For example somatic cells may originate from fetal, neonatal or adult tissue. Especially preferred somatic cells are those of foetal or neonatal origin. However, cells from a germ line may also be used. According to the present invention a donor cell is a somatic cell. In another embodiment of the present invention the donor cell is a cell derived from a germ cell line.

In a preferred embodiment of the present invention the donor cell harbours desired genetic properties. However, the donor cell may harbour desired genetic properties which have been gained by genetic manipulation as described elsewhere herein. The present invention thus relates to a modified porcine donor cell (or cell nucleus), derived from the genetically modified pig model as disclosed herein and/or the modified porcine donor cell or cell nucleus, wherein the genetically modified genome comprises at least one site for integration of at least one transgene.

Somatic cells are selected from the group consisting of epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells.

These may be obtained from different organs, e.g., skin, lung, pancreas, liver, stomach, intestine, heart, reproductive organs, bladder, kidney, urethra and other urinary organs.

The pigs from which the somatic cells may be derived are described elsewhere herein. A preferred embodiment of the invention is the use of somatic cells originating from the same species as the recipient oocyte (cytoplast).

Preferably, the somatic cells are fibroblast cells as the can be obtained from both developing fetuses and adult animals in large quantities. Fibroblasts may furthermore be easily propagated in vitro. Most preferably, the somatic cells are in vitro cultured fibroblasts of foetal origin.

In a preferred embodiment the somatic cells are genetically modified. In yet a further preferred embodiment of the present invention the somatic cells are preferably of foetal origin, or for example from adults.

The donor cell or nucleus of the present invention harbours desired genetic properties. The donor cell or nucleus carries a SB tagged genome containing a Flp recombination target site for site specific gene insertion or integration. The SB tagged genome result from the integration of a recombinant target vector comprising a DNA transposon construct and a bicistronic gene cassette comprising (i) a FRT recombination site and (ii) an IRES-driven selection gene. The DNA transposon construct may be any construct in which any DNA transposon is present. In the present invention the DNA transposon construct is the Sleeping Beauty (SB) DNA transposon vector. The FRT recombination site may be embedded in the coding sequence of a selection gene which allows for detecting whether a transposition has occurred. The selection gene of the present invention is not limited to any particular selection gene. In preferred embodiments the selection gene are genes conferring resistance to antibiotics or drugs, such as puromycin, tetracycline, streptomycin or hygromycin resistance genes, or the enhanced green fluorescent protein (eGFP) gene, red fluorescent protein genes or the like.

The FRT recombination site may thus be embedded in a SV40 promoter driven fusion variant of the selection gene. However, any promoter suitable for conferring expression of a selection gene may be used according to the present invention. Non-limiting examples of such promoters are CMV (cytomegalovirus) or PGK promoter.

The IRES-driven selection gene is similarly not limited to any particular selection gene. In preferred embodiments the selection gene are genes conferring resistance to antibiotics or drugs, such as puromycin, tetracycline, streptomycin or hygromycin resistance genes, or the enhanced green fluorescent protein (eGFP) gene, red fluorescent protein genes or the like.

The recombinant vector construct may also comprise at least one site for Cre recombinase. The at least one site for Cre recombinase may be located as disclosed in the examples herein.

The donor cell or nucleus may also originate from a genetically modified pig comprising at least one site for integration of at least one transgene. A preferred embodiment is a donor cell or nucleus in the form of a fibrobast, such as a primary fibroblast.

Enucleation

The method of enucleation of an oocyte may be selected from the group of methods consisting of aspiration, physical removal, use of DNA-specific fluorochromes, exposure to ultraviolet light and/or chemically assisted enucleation. In one embodiment the present invention relates to the use of DNA-specific fluorochromes. Enucleation may, however, be performed by exposure with ultraviolet light. In a particular embodiment enucleation is chemically assisted prior to physical removal of the nucleus. Chemically assisted enucleation using for example antineoplastic agents, such as demecolcine (N-deacetyl-N-methyl 1 colchicine), and/or for example etoposide or related agents may be performed prior to enzymatic modification of zona pellucida. Chemically assisted enucleation comprises culturing matured COCs in maturation medium as described elsewhere herein supplemented with demecolcine for a particular period of time. In the range of 0.1 µg/ml to 10 µg/ml demecolcine, such as 0.2 µg/ml to 10 µg/ml, for example 0.3 µg/ml to 10 µg/ml, such as 0.25 µg/ml to 5 µg/ml, for example 0.3 µg/ml to 1 µg/ml, such as 0.25 µg/ml to 0.5 µg/ml, for example 0.4 µg/ml demecolcin may be supplemented to the maturation medium. Similarly, maturation medium may be supplemented with etoposide for example in the range of 0.1 µg/ml to 10 µg/ml etoposide, such as 0.2 µg/ml to 10 µg/ml, for example 0.3 µg/ml to 10 µg/ml, such as 0.25 µg/ml to 5 µg/ml, for example 0.3 µg/ml to 1 µg/ml, such as 0.25 µg/ml to 0.5 µg/ml, for example 0.4 µg/ml etoposide may be supplemented to the maturation medium. The time for culturing the COCs in the presence of antineoplastic agents ranges from 10 min to 5 hrs, such as 30 minutes to 5 hrs, for example 10 minutes to 2 hrs, such as 30 min to 2 hrs, for example 10 min to 1.5 hrs, such as 20 min to 3 hrs, for example 10 min to 3 hrs, such as 30 min to 1.5 hrs, for example 45 min.

In a particular embodiment chemically assisted enucleation is performed using 0.45 µg/ml demecolcine and/or etoposide added to the maturation medium for 45 min.

In a particular embodiment it is preferred that the enucleation is by physical removal of the nucleus. The physical removal may be by separation for example by bisection of the oocyte into two halves (two parts), one which contains the nucleus and the enucleated oocyte half, known as the cytoplast, removing the nucleated half of the oocyte and selecting the resulting cytoplast for further procedures of the invention. Alternatively the separation is by trisection, resulting in three parts of which two parts are cytoplasts. In another embodiment the oocyte may be separated into four parts, resulting in the production of three cytoplasts. The oocyte may even be separated into five parts by physical removal, resulting in four cytoplasts. Similarly, the oocyte may be separated into six parts, for example seven parts, such as eight parts, for example nine parts, such as ten or more parts.

The physical separation of the oocyte and subsequent removal of the nucleus-bearing part of the oocyte may be achieved by the use of a microsurgical blade.

The oocytes may be screened to identify which oocytes have been successfully enucleated. Oocyte parts that harbour nuclear DNA may be identified by staining with Hoechst fluorochrome, the staining procedure of which is known to a person skilled in the art. Oocyte parts harbouring nuclear DNA are discarded and the enucleated oocytes (cytoplasts) are selected for further procedures.

Zona Pellucida

Zona pellucida is a thick, transparent, noncellular layer or envelope of uniform thickness surrounding an oocyte Generally, an intact zona pellucida is considered to be important in cell nuclear transfer due to a number of parameters. One parameter is to keep the polar body close to the metaphase plate of the oocyte in order to indicate the appropriate site for enucleation. Another parameter relates to the keeping of the donor cell close to the oocyte cytoplast before and during fusion. The zona is also believed to confer protection for the donor cell and cytoplast during fusion. Finally, embryo development after reconstitution and activation is believed to be supported by the zona pellucida.

Modification of at least a part of the zona pellucida can be performed by a number of methods. For example physical manipulation can be used to modify the zona. But also chemical treatment with agents such as acidic solutions (acidic Tyrode) can be employed. One example of chemical agents that can be employed in the present invention is acidic solutions, for example Tyrode. In a particular embodiment of the invention the zona pellucida is modified by enzymatic digestion. Such enzymatic digestion may be performed by enzymes comprising for example trypsin. Alternatively a specific protease may be used, such as pronase.

In a preferred embodiment the enzymatic digestion results in at least a partial digestion of a part of zona pellucida which in a preferred embodiment of the present invention means that at least a part of the zona pellucida is being removed, or that the zona pellucida is partly removed. In the present context the zona pellucida is not completely removed.

According to an especially preferred embodiment of the present invention the partially digested part of zona pellucida is characterized by the zona pellucida still being visible and by the fact that the oocyte has not become misshaped.

The partial digestion may be achieved by exposure to a protease. In another embodiment of the present invention the partial digestion may be accomplished by the use of a pronase. In yet another embodiment the partial digestion may be achieved by a combination of a protease and pronase.

In a preferred embodiment the concentration of pronase is in the range of 0.1 mg/ml to 10 mg/ml, such as 0.5 mg/ml to 10 mg/ml, for example 1 mg/ml to 10 mg/ml, such as 1.5 mg/ml to 10 mg/ml, for example 2 mg/ml to 10 mg/ml, such as 2.5 mg/ml to 10 mg/ml, for example 2.75 mg/ml to 10 mg/ml, such as 3 mg/ml to 10 mg/ml, for example 3.25 mg/ml to 10 mg/ml, such as 3.3 mg/ml to 10 mg/ml, for example 3.5 mg/ml to 10 mg/ml.

A preferred embodiment is a pronase concentration in the range of 2 mg/ml to 5 mg/ml, such as 2.25 mg/ml to 5 mg/ml, for example 2.5 mg/ml to 5 mg/ml, such as 2.75 mg/ml to 5 mg/ml, for example 2.8 mg/ml to 5 mg/ml, such as 2.9 mg/ml to 5 mg/ml, for example 3 mg/ml to 5 mg/ml, such as 3.1 mg/ml to 5 mg/ml, for example 3.2 mg/ml to 5 mg/ml, such as 3.3 mg/ml to 5 mg/ml.

A particular embodiment of the present invention is a pronase concentration in the range of 1 mg/ml to 4 mg/ml, for example 1 mg/ml to 3.9 mg/ml, such as 1 mg/ml to 3.8 mg/ml, for example 1 mg/ml to 3.7 mg/ml, such as 1 mg/ml to 3.6 mg/ml, for example 1 mg/ml to 3.5 mg/ml such as 1 mg/ml to 3.4 mg/ml, for example 1 mg/ml to 3.3 mg/ml.

In a preferred embodiment the pronase concentration is in the range of 2.5 mg/ml to 3.5 mg/ml, such as 2.75 mg/ml to 3.5 mg/ml, for example 3 mg/ml to 3.5 mg/ml. In a special embodiment the pronase concentration is 3.3 mg/ml.

It is clear to the skilled person that the pronase should be dissolved in an appropriate medium, one preferred medium according to the present invention is T33 (Hepes buffered TCM 199 medium containing 33% cattle serum (as described earlier—Vajta, et al., 2003).

The time of incubation of the oocyte in the pronase solution is in the range of 1 second to 30 seconds, such as 2 seconds to 30 seconds, for example 3 seconds to 30 seconds, such as 4 seconds to 30 seconds, such as 5 seconds to 30 seconds.

In another embodiment of the present invention the incubation time is in the range of 2 seconds to 15 seconds, such as 2 seconds to 14 seconds, for example 2 seconds to 13 seconds, such as 2 seconds to 12 seconds, for example 2 seconds to 11 seconds, such as 2 seconds to 10 seconds, for example 2 seconds to 9 seconds, such as 2 seconds to 8 seconds, for example 2 seconds to 7 seconds, such as 2 seconds to 6 seconds, for example 2 seconds to 5 seconds.

In a particular embodiment of the present invention the incubation time is in the range of 3 seconds to 10 seconds, such as 3 seconds to 9 seconds, for example 4 seconds to 10 seconds, such as 3 seconds to 8 seconds, for example 4 seconds to 9 seconds, such as 3 seconds to 7 seconds, for example 4 seconds to 8 seconds, such as 3 seconds to 6 seconds, for example 4 seconds to 7 seconds, such as 3 seconds to 5 seconds, for example 4 seconds to 6 seconds, such as 4 seconds to 5 seconds. An especially preferred incubation time is 5 seconds.

In a preferred embodiment of the present invention the oocyte is treated for 5 seconds in a 3.3 mg/ml pronase solution at 39° C.

Reconstructed Embryo

By the term 'reconstructed embryo' is meant the cell which is formed by insertion of the donor cell or nucleus of the donor cell into the enucleated oocyte which corresponds to a zygote (during normal fertilisation). However, the term 'reconstructed embryo' is also referred to as the 'reconstituted cell'. In the present invention the donor cell is a somatic cell. However, the donor cell may also be derived from a germ line cell.

Fusion

The transfer of a donor cell or a membrane surrounded nucleus from a donor cell to at least cytoplast is according to the present invention performed by fusion. In the scenarios described below the term 'donor cell' also refers to a membrane surrounded nucleus from a donor cell. Fusion may be achieved by a number of methods.

Fusion may be between a donor cell and at least one cytoplast, such as between a donor cell and at least two cytoplasts, for example between a donor cell and at least two cytoplasts, such as between a donor cell and at least three cytoplasts, such as between a donor cell and at least four cytoplasts, for example between a donor cell and at least five cytoplasts, such as between a donor cell and at least six cytoplasts, for example between a donor cell and at least seven cytoplasts, such as between a donor cell and at least eight cytoplasts.

Fusion may be performed according to the listed combinations above simultaneously or sequentially. In one embodiment of the present invention the fusion is performed simultaneously. In another embodiment fusion of the at least one cytoplast and a donor cell is performed sequentially.

For example fusion may be achieved by chemical fusion, wherein a donor cell and the at least one cytoplast are exposed to fusion promoting agents such as for example proteins, glycoproteins, or carbohydrates, or a combination thereof. A variety of fusion-promoting agents are known for example, polyethylene glycol (PEG), trypsin, dimethylsulfoxide (DMSO), lectins, agglutinin, viruses, and Sendai virus. Preferably phytohemaglutinin (PHA) is used. However mannitol and, or polyvinylalcohol may be used.

Alternatively, fusion may be accomplished by induction with a direct current (DC) across the fusion plane. Often an alternating current (AC) is employed to align the donor and recipient cell. Electrofusion produces a sufficiently high pulse of electricity which is transiently able to break down the membranes of the cytoplast and the donor cell and to reform the membranes subsequently. As a result small channels will open between the donor cell and the recipient cell. In cases where the membranes of the donor cell and the recipient cell connect the small channels will gradually increase and eventually the two cells will fuse to one cell.

Alignment of the at least one cytoplast and the donor cell may be performed using alternating current in the range of 0.06 to 0.5 KV/cm, such as 0.1 to 0.4 KV/cm, for example 0.15 to 0.3 KV/cm. In a preferred embodiment alignment of the at least one cytoplast and the donor cell may be performed using alternating current at 0.2 KV/cm. Fusion may be induced by the application of direct current across the fusion plane of the at least one cytoplast and the donor cell. Direct current in the range of 0.5 to 5 KV/cm, such as 0.75 to 5 KV/cm, for example 1 to 5 KV/cm, such as 1.5 to 5 KV/cm, for example 2 to 5 KV/cm. Another preferred embodiment of the present invention is the application of direct current in the range of 0.5 to 2 KV/cm. In a further preferred embodiment the direct current may be 2 KV/cm.

The direct current may preferably be applied for in the range of 1-15 micro seconds, such as 5 to 15 micro seconds, for example 5 to 10 micro seconds. A particular embodiment may be 9 micro seconds.

In an especially preferred embodiment fusion with direct current may be using a direct current of 2 KV/cm for 9 micro seconds.

Electrofusion and chemical fusion may however be also be combined.

Typically electrofusion is performed in fusion chambers as known to the skilled person.

Fusion may be performed in at least one step, such as in two steps, for example three steps, such as in four steps, for example in five steps, such as six steps, for example seven steps, such as in eight steps.

Fusion may be performed in for example a first step wherein the at least one cytoplast is fused to the donor cell. A second step of fusion may comprise fusion of the fused pair (cytoplast-donor cell, reconstructed embryo) with at least one cytoplast, such as at least two cytoplasts, for example three cytoplasts, such as four cytoplasts, for example five cytoplasts, such as six cytoplasts, for example seven cytoplasts, such as eight cytoplasts. The second step of fusion with fusion of at least one cytoplast and the fused pair may be performed sequentially or simultaneously. In one embodiment the at least two cytoplasts are fused to the fused pair simultaneously. In another embodiment the at least two cytoplasts are fused to the fused pair sequentially.

In one embodiment of the invention the second step of fusion may also be an activation step wherein the reconstructed embryo is activated to enter mitosis. As described elsewhere herein.

Activation

In a preferred embodiment the reconstructed embryo may be allowed to rest prior to activation for a period of time in order to allow for the nucleus of the donor cell to reset its genome and gain toti potency in the novel surroundings of the enucleated cytoplast. The reconstructed embryo may for example rest for one hour prior to activation.

Preferably, the reconstructed embryo may be activated in order to induce mitosis. Methods for activation may preferably be selected from the group of consisting of electric pulse, chemically induced shock, increasing intracellular levels of divalent cations or reducing phosphorylation. A combination of methods may be preferred for activation.

In one particular embodiment of the invention the activation and the second step of fusion may be performed simultaneously. However, the activation of the reconstituted embryo and the at least one additional step of fusion between the reconstructed embryo and the at least one cytoplast may be performed sequentially.

Reducing the phosphorylation of cellular proteins in the reconstructed embryo by known methods such as for example by the addition of kinase inhibitors may activate the reconstituted embryo. A preferred embodiment may involve the use of agents that inhibit protein synthesis, for example cycloheximide. A further preferred embodiment may be using agents that inhibit spindle body formation, for example cytochalasin B.

In one embodiment of the invention the intracellular levels of divalent cations may be increased. Divalent cations such as for example calcium may be in comprised in the activation medium. Preferably, the cations may enter the reconstructed embryo, particularly upon subjecting the reconstructed embryo to an electric pulse. In a preferred embodiment the electric pulse may cause entering of calcium into the reconstructed embryo.

The application of an electrical pulse using direct current may be an activation step. However, in a preferred embodiment the electrical pulse applied for activation may also serve as an additional fusion step.

Prior to applying an electrical pulse using direct current the at least one cytoplast and the at least one reconstructed embryo may be aligned by the application of alternating current. The alternating current may be in the range of the range of 0.06 to 0.5 KV/cm, such as 0.1 to 0.4 KV/cm, for example 0.15 to 0.3 KV/cm. In a preferred embodiment alignment of the at least one cytoplast and the donor cell may be performed using alternating current at 0.2 KV/cm.

Activation may be induced by the application of direct current across the fusion plane of the at least one cytoplast and the donor cell. Direct current in the range of 0.2 to 5 KV/cm, such as 0.4 to 5 KV/cm, for example 0.5 to 5 KV/cm. Another preferred embodiment of the present invention is the application of direct current in the range of 0.5 to 2 KV/cm. In a further preferred embodiment the direct current may be 0.7 KV/cm.

The direct current may preferably be applied for in the range of 10 to 200 micro seconds, such as 25 to 150 micro seconds, for example 50 to 100 micro seconds. A particular embodiment may be 80 micro seconds.

In an especially preferred embodiment fusion with direct current may be using a direct current of 0.7 KV/cm for 80 micro seconds.

An especially preferred embodiment of activation according to the present invention may be use of an electrical pulse in combination with subjecting the reconstructed embryo to agents that inhibit protein synthesis, spindle body formation, and divalent cations.

Activation may be performed by any combination of the methods described above.

In Vitro Culture of Embryos

One aspect of the invention relates to a method of in vitro culturing embryos, whereby the blastocyst rate increased to 25.3%. Thus, a method of culturing a reconstructed embryo is within the scope of the present invention, comprising the steps of a) establishing at least one oocyte having at least a part of zona pellucida, b) separating the oocyte into at least two parts obtaining an oocyte having a nucleus and at least one cytoplast, c) establishing a donor cell or cell nucleus having desired genetic properties, d) fusing at least one cytoplast with the donor cell or membrane surrounded cell nucleus, e) obtaining the reconstructed embryo, f) activating the reconstructed embryo to form an embryo, and e) culturing said embryo.

Another aspect of the invention relates to a method of cell nuclear transfer in which a step of culturing the embryo is included.

In a preferred embodiment in relation to the methods described herein embryos are cultured in a sequential set of media. Preferably the blastocysts are grown in traditional medium such as for example NCSU37 or equivalent medium as known to a person skilled in the art, wherein glucose is removed and substituted by other agents. One agent may be pyruvate. Another agent may be lactate. The agents may also be combined and replace glucose in the traditional medium.

The embryos may be cultured in the substituted media as described above from Day 0 to Day 3, such as from Day 0 to Day 2.

The pyruvate concentration may range from 0.05 to 1 mM, such as 0.1 to 1 mM, for example 0.125 to 1 mM, such as 0.15 to 1 mM. However the concentration of sodium pyruvate may also range from 0.05 mM to 0.9 mM, such as 0.05 to 0.8 mM, for example 0.05 to 0.7 mM, such as 0.05 to 0.6 mM, for example 0.05 to 0.5 mM, such as 0.05 to 0.4 mM, for example 0.05 to 0.3 mM, such as 0.05 to 0.2 mM. Preferably the concentration ranges between 0.05 to 0.17 mM. A preferred concentration of sodium pyruvate is 0.17 mM.

The lactate concentration may range from 0.5 to 10 mM, such as 0.75 to 10 mM, for example 1 to 10 mM, such as 1.5 to 10 mM, such as 1.75 to 10 mM, for example 2 to 10 mM, such as 2.5 to 10 mM. However the concentration of sodium lactate may also range from 0.5 mM to 9 mM, such as 0.5 to 8 mM, for example 0.5 to 7 mM, such as 0.5 to 6 mM, for example 0.5 to 5 mM, such as 0.5 to 4 mM, for example 0.5 to 03 mM. Preferably the concentration ranges between 1 to 5 mM, such as 2 to 4 mM, for example 2 to 3 mM. A preferred concentration of sodium lactate is 2.73 mM.

After the initial glucose-free incubation medium glucose is again replacing the pyruvate and lactate. The embryos may be cultured in the glucose containing medium from Day 4 to Day 3, preferably from Day 3 to Day 7. The glucose concentration may range from 1 to 10 mM, such as 2 to 10 mM, for example 3 to 10 mM, such as 4 to 10 mM, for example 5 to 10 mM. However, the glucose concentration may also range from 1 to 9 mM, such as 2 to 8 mM, for example 3 to 7 mM, such as 4-6 mM. A preferred concentration of glucose according to the present invention is 5.5 mM of glucose.

Organ or Tissue Donation

In one embodiment, the animals of the invention may be used as a source for organ or tissue donation for humans or other animals, either animals of the same species or animal of other species. Transfer between species is usually termed xenotransplantation. Entire organs that may be transplanted include the heart, kidney, liver, pancreas or lung. Alternatively, parts of organs, such as specific organ tissues may be transplanted or transferred to humans or other animals. In a yet further embodiment, an individual cell or a population of individual cells from an animal of the invention may be transferred to a human being or another animal for therapeutic purposes.

Cryopreservation

The term 'cryopreserving' as used herein can refer to vitrification of an oocyte, cytoplast, a cell, embryo, or pig of the invention. The temperatures employed for cryopreservation is preferably lower than −80 degree C., and more preferably at temperatures lower than −196 degree C. Oocytes, cells and embryos of the invention can be cryopreserved for an indefinite amount of time. It is known that biological materials can be cryopreserved for more than fifty years.

It is within the scope of the present invention that embryos may be cryopreserved prior to transfer to a host pig when employing methods for producing a genetically engineered or transgenic non-human mammal. Such cryopreservation prior to transfer may be at the blastocyst stage the of embryo development. Vitrification is a form of cryopreservation where living cells are rapidly cooled so that the fluid of the cell does not form into ice. Thus, vitrification relates to the process of cooling where cells or whole tissues are preserved by cooling to low sub-zero temperatures, such as (typically) −80 C or −196 C In particular the invention relates to the vitrification of an oocyte, however, the invention also relates to the vitrification of embryos, preferably embryos at the blastocyst stage. In one embodiment, the embryo is cultured to blastocyst stage prior to vitrification.

Especially pig embryos are covered by the present invention. Also vitrified cytoplasts are covered by the present invention, as are cells.

Yet another aspect of the invention relates to the cryopreservation of a pig embryo derived by a method for cell nuclear transfer as described herein comprising a step of vitrifying a pig embryo. A further aspect of the invention relates to pig embryos obtained, or obtainable by the methods provided herein.

Mitochondria

Cells of the tissue of the genetically modified non-human mammals and/or non-human embryos obtainable by the present invention may harbour mitochondria of different maternal sources. In a preferred embodiment the non-human mammals and/or non-human embryos may harbour mitochondria from only one maternal source, However, in another preferred embodiment the non-human mammals and/or non-human embryos may harbour mitochondria from at least two maternal sources, such as three maternal sources, for example four maternal sources, such as five maternal sources, for example six maternal sources, such as seven maternal sources, for example eight maternal sources, such as nine maternal sources, for example ten maternal sources. The probability of having a specific number of maternal sources can be calculated based on the observed types of mitochondria.

EXAMPLES

Based on the well-described mechanisms of SB transposition (4-8) and Flp recombination (9, 10), the present invention discloses a new target vector for site-specific integration into the genome. This vector carries within the context of a SB transposon vector a bicistronic gene cassette containing (i) the FRT recombination site embedded in the coding sequence of eGFP and (ii) an IRES-driven puromycin resistance gene. We demonstrate efficient selective plasmid insertion into SB-tagged genomic loci. In an attempt to further improve the performance of these vectors, we have analyzed the effect of insulator elements, believed to protect inserted foreign genes against transcriptional silencing, within the context of SB vectors. Our investigations indicate that insulators flanking the FRT gene expression cassette may serve to maintain and stabilize gene expression of Flp-inserted transgenes.

Two nonviral integration technologies are employed in the present invention, the SB transposon system and the Flp recombinase, in a combined effort to achieve active locus detection, mediated by SB, and site-directed insertion at an attractive site, mediated by Flp. A bi-phased technology is disclosed in which an integrating SB vector, carrying a reporter gene and a selective marker gene, may first serve as a reporter for continuous gene expression and hence as a target for gene insertion (FIG. 1). By using an actively integrated vector as opposed to plasmid DNA that is randomly recombined into the genome we certify (i) that only a single copy, and not concatemers, of the vector are inserted and, moreover, (ii) that the reporter cassette is not flanked by sequences derived from the bacterial plasmid backbone which may have a detrimental effect on the locus activity over time. In a second modification step this vector may serve as a target for insertion of one or more gene expression cassettes in a well-characterized locus.

DNA Transposon-Based Genomic Insertion of Recombinase Recognition Sites

Epigenetic modifications leading to transcriptional silencing of inserted foreign DNA are major challenges in strategies for genetic manipulation of cell lines and transgenic animals. Hence, both the identification of active genomic loci which support continuous, undisturbed gene expression and development of genetic tools to insert genes of interest site-specifically at these preferred loci are key aims in genetic engineering. We use in this study two nonviral integration technologies, the SB transposon system and the Flp recombinase, in a combined effort to achieve active locus detection, mediated by SB, and site-directed insertion at an attractive site, mediated by Flp. We describe a bi-phased technology in which an integrating SB vector, carrying a reporter gene and a selective marker gene, may first serve as a reporter for continuous gene expression and hence as a target for gene insertion (FIG. 1). By using an actively integrated vector as opposed to plasmid DNA that is randomly recombined into the genome we certify (i) that only a single copy, and not concatemers, of the vector are inserted and, moreover, (ii) that the reporter cassette is not flanked by sequences derived from the bacterial plasmid backbone which may have a detrimental effect on the locus activity over time.

In a second modification step this vector may serve as a target for insertion of one or more gene expression cassettes in a well-characterized locus (FIG. 1B).

The Transgenic Model System

To circumvent the problems existing for random transgenesis in terms of copy numbers and variable insertion position we examined the possibility to perform controlled transgenesis for the future generation of cloned transgenic pigs by SCNT. The strategy was to insert a model gene-cassette into the porcine genome by use of a SB transposon-derived vector and subsequently use the Flp recombinase recognition site within the cassette to introduce a transgene and selection marker through a specific recombination event.

A transposon, pSBT/SV40-FGIP, was constructed for the use in porcine transgenesis. For a schematic description of the construct see FIG. 2A. The enhanced green fluorescent protein (eGFP) gene was linked to a puromycin resistance gene through an internal ribosome entry site (IRES). This bicistronic gene cassette was placed under control of the SV40 promoter. The original start codon of the eGFP gene was replaced by a start codon located upstream of an inserted FRT site. We have previously shown that this fusion variant of the eGFP gene encodes fluorescent protein [28]. The FRT site is positioned immediately after the SV40 promoter and should enable Flp-mediated recombination. If such a recombination event is successful the eGFP and puromycin resistance genes will be removed from the promoter context and rendered inactive. The plasmid DNA inserted at the FRT site thus can be constructed such that the expression of a novel selection marker, the hygromycin B resistance gene (hygro$^R$), is dependent of the ATG start codon already present upstream from the FRT site located in the transposon (FIG. 2B). This selection marker exchange will allow selecting for only correct and site-directed recombination events. By including a gene of interest, here the DsRed marker gene under control of the cytomegalovirus (CMV) promoter, as a new transgenic unit on the plasmid carrying the FRT-hygro fusion gene, a colour shift from green to red can be monitored as a result of successful recombination.

The pSBT/RSV-GFIP Vector was Constructed as Follows:

The pSBT/RSV-GFIP vector contains the terminal inverted of the SB DNA transposon flanking a FRT-GFP.IRES.puro bicistronic gene cassette driven by a promotor derived from Rous sarcoma virus (RSV). The eGFP sequence was amplified from peGFP.N1 (Clontech) using a forward primer containing the 48-bp FRT sequence. To analyze FRT-GFP functionality, the FRT-eGFP fusion was inserted into an expression vector containing the SV40 promoter. The PCR-fragment containing FRT-tagged eGFP fusion gene was digested with MluI and XmaI and inserted into MluI/XmaI-digested pSBT/RSV-hAAT (pT/hAAT in ref. (8), obtained from Mark Kay, Stanford University, USA), generating a transposon vector with RSV-driven eGFP expression (pSBT/RSV-eGFP). An IRES-puro cassette was PCR-amplified from pecoenv-IRES-puro (provided by Finn Skou Pedersen, University of Aarhus, Denmark), digested with XmaI, and inserted into XmaI-digested pSBT/RSV-eGFP, generating pSBT/RSV-GFIP (see sequence listing). Alternative versions of this vector containing the SV40 promoter (pSBT/SV40-GFIP) and the promoter derived from the human ubiquitin gene (pSBT/Ubi-GFIP), were generated. In addition, by inserting a Cre recombination target site (IoxP) into the MluI site located between the left inverted repeat of the transposon and the SV40 promoter of pSBT/SV40-GFIP, the vector pSBT/SV40-GFIP.IoxP was created. The donor plasmid pcDNA5/FRT, containing a FRT-hygro fusion gene without a start codon, was obtained from Invitrogen. The Flp-encoding plasmid, pCMV-Flp was obtained from A. Francis Stewart, University of California San Francisco, USA). This plasmid encodes the enhanced Flp variant designated Flpx9 (11). A SB-vector containing two copies of the 1.2-kb chicken DNase hypersensitive site 4 (cHS4)-derived insulator element (12, 13) was generated by inserting PCR-amplified cHS4 sequences and an intervening linker into NotI/SpeI-digested pSBT/PGK-puro (obtained from Mark Kay, Stanford University, USA). The PGK-puro cassette was cloned back into construct by using restriction sites located in the linker, generating pSBT/cHS4.PGK-puro.cHS4. All self-inactivating (SIN) lentiviral vector constructs were derived from pCCL.WPS.PGK-eGFP.WHV obtained from Dr. Aebischer, Swiss Federal Institute of Technology, EPFL, Lausanne, Switzerland. The puromycin resistance gene was amplified by PCR and inserted in pCCL.WPS.PGK-eGFP.WHV downstream from the promoter, generating pCCL.WPS.PGK-puro.WHV The FRT-hygro fusion gene was PCR-amplified from pcDNA5/FRT and inserted into the HpaI site (located between 4) and cPPT cis elements) of pCCL.WPS.PGK-puro.WHV, generating pLV/FRT-hygro.PGK-puro. To generate pLV/PGK-Flp the Flp gene was PCR-amplified from pCMV-Flp, digested with BamHI/XhoI, and inserted into BamHI/XhoI-digested pCCL.WPS.PGK-puro.WHV.

Transposition of FRT-Tagged SB Vectors

Figure 3:
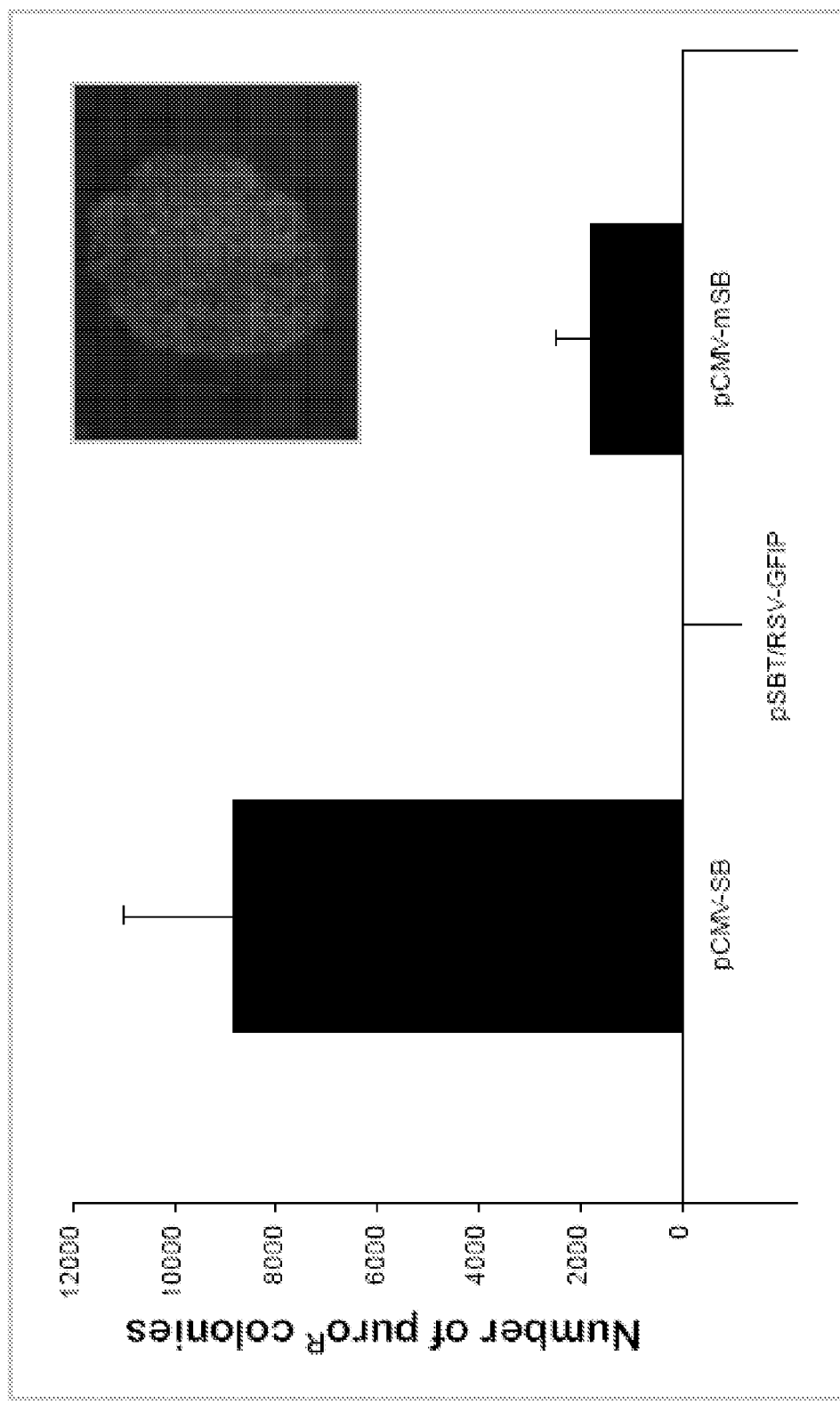
FIG. 3 shows the transposition efficiency of pSBT/RSV-GFIP by co-transfecting with pCMV-SB and pCMV-mSB, respectively, in HEK-293 cells. As expected the GFIP transposon was efficiently transposed into the genomic DNA thereby conferring resistance to puromycin.

To be able to easily follow the activity of SB-tagged loci in modified cells, we constructed SB transposon vectors (pSBT/SV40-GFIP, pSBT/SV40-GFIP.IoxP, pSBT/RSV-GFIP) containing a bicistronic gene expression cassette encoding eGFP and the puromycin resistance gene. We inserted the 48-bp Flp recombination target sequence (FRT) immediately downstream from the eGFP start codon, generating a fusion gene encoding FRT-tagged eGFP. Transient expression studies demonstrated comparable levels of activity of the eGFP and FRT-eGFP proteins (data not shown). We tested first the transposition efficiency of pSBT/RSV-GFIP by co-transfecting with pCMV-SB and pCMV-mSB, respectively, in HEK-293 cells. As expected the GFIP transposon was efficiently transposed into the genomic DNA thereby conferring resistance to puromycin (FIG. 3). As an alternative strategy, optimized for use in hard-to-transfect cell lines, we generated a helper-independent transposon-transposase (HITT) vector (the concept first demonstrated by Mikkelsen et al. in (6)) in which the GFIP-containing transposon and the SB expression cassette were located on a single plasmid. Transposition assays using this HITT configuration showed high levels of transposition in HeLa cells (data not shown). By analysis of puromycin-resistant colonies generated with two-plasmid transfections, stable eGFP expression was verified by fluorescence microscopy (FIG. 3, insert), demonstrating functionality of both vector genes. Three puromycin-resistant clones, HEK-GFIP1, HEK-GFIP2, and HEK-GFIP3, obtained by insertion of SBT/SV40-GFIP.IoxP, SBT/SV40-GFIP, and SBT/RSV-GFIP transposons, respectively, were isolated and expanded for further analysis.

The target transposon SBT/RSV-GFIP was inserted into the genome of HEK-293 cells by co-transfecting (using Fugene-6 from Roche) 1.5 µg pSBT/RSV-GFIP with 1.5 µg pCMV-SB (or 1.5 µg pCMV-mSB as a negative control). pCMV-SB, obtained from Perry Hackett, University of Minnesota, Minnesota, USA, encodes the Sleeping Beauty transposase reconstructed from fossil DNA transposable elements of salmoid fish. SB-tagged cell clones were generated by selecting transfected cells with puromycin (1 µg/ml). Clones were isolated and expanded and utilized as target clones for Flp-mediated gene insertion. To demonstrate site-specific insertion of transfected plasmid DNA 12 µg pCMV-Flp was co-transfected (by CaPO$_4$) with either (i) 3 µg pcDNA5/FRT or (ii) 3 µg pLV/FRT-hygro.PGK-puro into SBT/RSV-GFIP-tagged HEK-293 cells. To select for site-specific insertions cells were grown in medium containing hygromycin B (200 µg/ml).

Cloning of Constructs

Vectors expressing different variants of the SB transposase were generated by inserting PCR-amplified transposase sequences into the pcDNA3.1D/V5.His.Topo vector (Invitrogen, Carlsbad, Calif.). SB sequences utilized to generate pCMV-mSB.Topo, pCMV-SB.Topo or the pCMV-HSB3.Topo mSB, SB10, and HSB3 sequences were derived from pCMV-mSB (Yant S R, Meuse L, Chiu W, Ivics Z, Izsvak Z, Kay M A: Somatic integration and long-term transgene expression in normal and haemophilic mice using a DNA transposon system. Nat Genet. 2000, 25(1):35-41), pCMV-SB (Yant S R, Meuse L, Chiu W, Ivics Z, Izsvak Z, Kay M A: Somatic integration and long-term transgene expression in normal and haemophilic mice using a DNA transposon system. Nat Genet. 2000, 25(1):35-41), and pCMV-HSB3 (Yant S R, Park J, Huang Y, Mikkelsen J G, Kay M A: Mutational analysis of the N-terminal DNA-binding domain of sleeping beauty transposase: critical residues for DNA binding and hyperactivity in mammalian cells. Mol Cell Biol 2004, 24(20):9239-9247), respectively. The SB-based docking vector, pSBT/SV40-FGIP, was generated from pSBT/RSV-FGIP (Moldt B, Staunstrup N H, Jakobsen M, Yanez-Munoz R J, Mikkelsen J G: Site-directed genomic insertion of lentiviral DNA circles, Submitted for publication) by replacing the RSV promoter with a PCR-amplified SV40 promoter. pSBT/PGK puro has been described previously (Yant S R, Meuse L, Chiu W, Ivics Z, Izsvak Z, Kay M A: Somatic integration and long-term transgene expression in normal and haemophilic mice using a DNA transposon system. Nat Genet. 2000, 25(1):35-41). To generate the transgene donor plasmid, designated pFRT/hygro.CMV-DsRed, the red fluorescence protein gene (RFP) was derived from pDS-red-N1 by cleavage with HindIII and NotI restriction enzymes. The RFP gene was inserted into the pcDNA5/FRT vector (Invitrogen, Carlsbad, Calif.).

Transposition Assays and Flp Recombination $2.6 \times 10^4$ NPFs, HEK293 cells, or NIH3T3 cells, seeded in 6-well dishes, were co-transfected with 0.5 μg plasmid DNA carrying the transposon (SBT/PGK-puro or SBT/SV40-FGIP) and 0.5 μg of pCMV-mSB.Topo, pCMV-wt-SB.Topo, or pCMV-HSB3.Topo. Transfections were performed with Fugene-6 (Roche, Basel, Switzerland) according to the manufacturer's instructions. Transgenic NPF colonies harboring SBT/SV40-FGIP were harvested after 9 days of puromycin selection. Solitary colonies were scraped off with a glass pasteur pipette and transferred to 96-well dishes. The cells were expanded and used for studies of Flp recombination or handmade cloning. All transposition experiments were carried out in triplicates and cell colonies were counted after staining the colonies in methylene blue after 9 days of puromycin selection. Flp recombination was carried out as follows: for neonatal pig fibroblasts (NPFs), pools of clones containing the SBT/SV40-FGIP transposon were co-transfected with 5.5 ug of the FLP recombinase expression vector (pOG44; Invitrogen, Carlsbad, Calif.) and 0.5 μg donor plasmid using Fugene-6 as transfection reagent. On the following the day, cells were washed with PBS and starting from day two after transfection the cells were grown in medium containing 400 ug/μl hygromycin B for 11 days. Selection was carried out for 11 days prior to harvesting of the cells and DNA purification. PCR using genomic DNA from pooled NPFs as template was performed to verify Flp recombination. A forward primer located downstream from LIR and a reverse primer located at the beginning of the hygro$^R$ gene was used to amplify the fragment of interest. The presence of a precise junction between the SV40 promoter and the hygro$^R$ gene was confirmed by sequencing of the PCR fragment. For studies in HEK293 and NIH3T3 cells, $8 \times 10^5$ cells seeded in 10-cm dishes were co-transfected with 1 ug of donor plasmid and 9 ug of pOG44 by treating the cells with calcium phosphate. The transfection mixture was left on the cells overnight and $1 \times 10^5$ cells were subsequently seeded in 70 cm$^2$ bottles and subjected to hygromycin B (200 ug/μl) selection for 11 days. Cell colonies were stained with methylene blue prior to counting of the colonies.

Sleeping Beauty (SB) Transposition in Neonatal Porcine Fibroblasts (NPFs)

The applicability of SB transposition in pig fibroblasts was tested in NPFs derived from a skin biopsy from a male Göttingen minipig (Ellegaard Göttingen Minipigs ApS) using a 2-kb long SB transposon designated SBT/PGK-puro (FIG. 4A). In pSBT/PGK-puro, the SB inverted repeats (IRs) flank an expression cassette consisting of the puromycin resistance gene driven by the phosphoglycerate kinase (PGK) promoter. pSBT/PGK-puro was co-transfected into NPFs with plasmid encoding either of three different SB transposase variants including a mutated inactive form (mSB), the original SB10, and the hyperactive version HSB3 encoded by pCMV-mSB-.Topo, pCMV-SB10.Topo, and pCMV-HSB3.Topo, respectively. After 9 days of puromycin selection fibroblast colonies were stained with methylene blue. The formation of colonies was highly enhanced by co-transfection with a functional transposase (FIG. 4B), and the hyperactive transposase generated two-fold more colonies than SB10 (FIG. 4B). We therefore conclude that SB mobilization and transposase-dependent transgenesis is highly efficient in NPFs.

Figure 5:
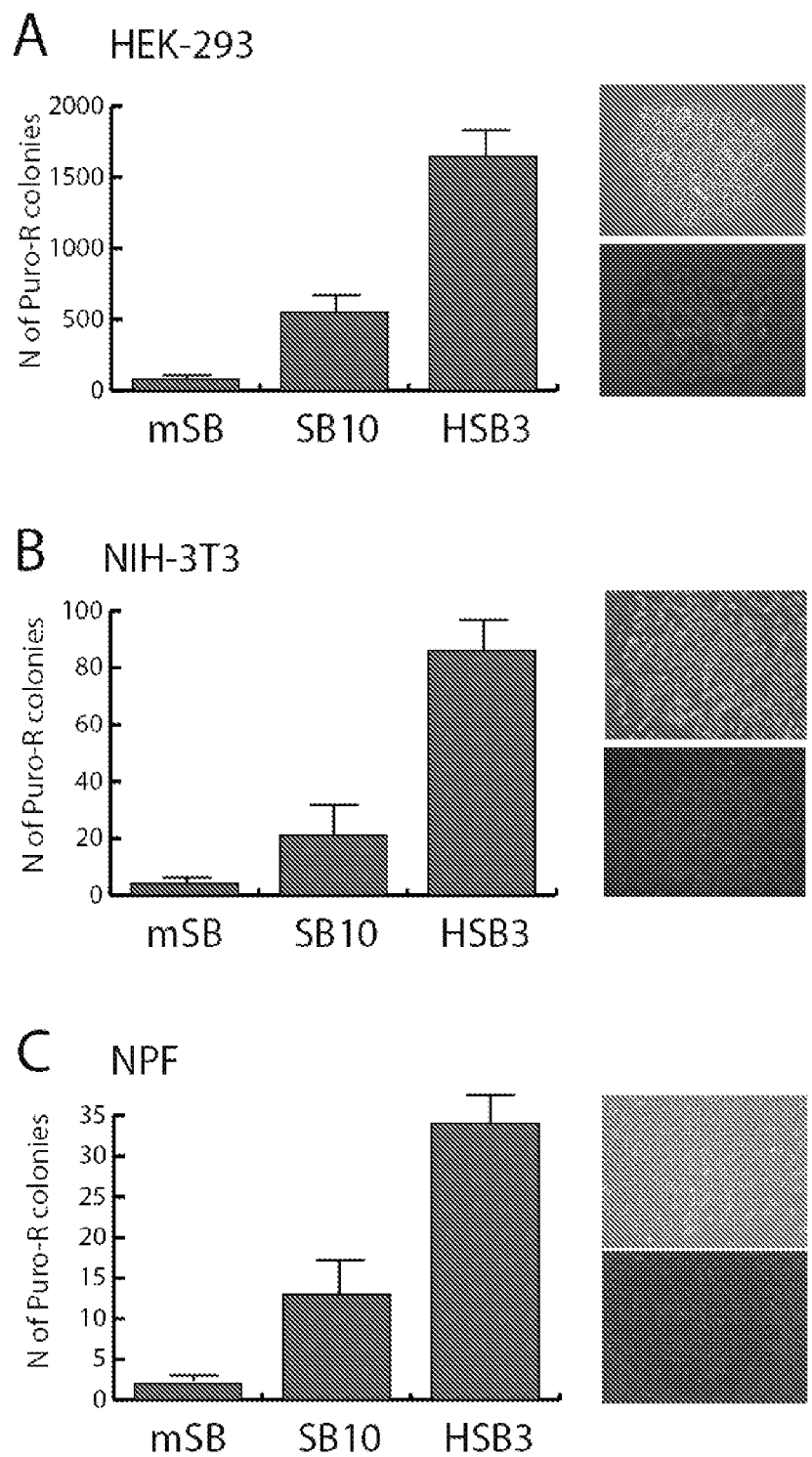
FIG. 5 shows that transgenesis by SBT/SV40-FGIP transposition is dependent of a functional transposase. The pSBT/SV40-FGIP plasmid was transfected together the plasmid DNA encoding mSB, SB10, or HSB3. The number of puromycin-resistant colonies was counted after 9 days of puromycin selection. Representative colonies were analyzed by phase contrast and epi-fluorescence microscopy to determine homogeneity in eGFP expression. The cell lines analyzed were in A) HEK-293, B) NIH-3T3, and C) NPFs.

SB transposition is strongly influenced by the transposon length (Izsvak Z, Ivics Z, Plasterk R H: Sleeping Beauty, a wide host-range transposon vector for genetic transformation in vertebrates. J Mol Biol 2000, 302(1):93-102). To test if the 3.3 kb long SBT/SV40-FGIP transposon (FIG. 2A) was efficiently inserted into the genome of NPFs primary cells were co-transfected with pSBT/SV40-FGIP and plasmid DNA encoding mSB, SB10, and HSB3, respectively. In this experiment we also included the murine fibroblast cell line NIH3T3 and the human kidney cell line HEK-293, as these two cell lines represent well-described cell types in which transposase-dependent gene insertion already has been described. Moreover, as NPFs are primary cells and have a short division potential, analyses that require long term growth in culture are not possible. The colony formation assay in HEK-293 cells showed a transposase-dependent increase in the number of puromycin-resistant colonies. The colony number was further increased by the hyperactive transposase (FIG. 5A). Similar results were obtained in NIH3T3 cells (FIG. 5B). Fluorescence microscopy analyses confirmed that colonies resulting from SBT/SV40-FGIP transposition expressed eGFP (FIG. 5, right panels and data not shown).

In NPFs, we again observed transposase-dependent formation of colonies. Compared to the shorter pSBT/PGK-Puro transposon, we consistently measured a decrease in colony forming efficiency for pSBT/SV40-FGIP (FIG. 4B versus FIG. 5C). This result is in accordance with previous findings showing that the efficiency of transposase-mediated transgenesis depends on the length of the insert between the IRs. Fluorescence microscopy of puromycin-resistant NPF colonies confirmed that all cells expressed eGFP (FIG. 5C, right). By comparing the extent of colony formation in the presence of active versus inactive transposase, our data suggest that the transposition efficiency in NPFs is comparable to the efficiencies measured in the NIH3T3 and HEK293 cell lines. We therefore conclude that the pSBT/SV40-FGIP vector is suitable for gene transfer in pig primary cells.

Transgene Substitution by Flp Recombination

Next, we wanted to examine the possibility of using the FRT site to substitute transgenes within porcine cells. For this purpose cells from clones containing the pSBT/SV40-FGIP transposon were re-transfected with an expression vector for Flp recombinase and the donor vector, pFRT/hygro.CMV-DsRed, which carries a new set of transgenes including the gene encoding DsRed driven by a CMV promoter and a promoter-less hygromycin gene lacking a start codon and flanked upstream by an FRT site (FIG. 1B). Flp-mediated recombination is expected to activate the expression of the hygromycin B resistance gene by inserting the ATG-less hygro gene downstream from the SV40 promoter and the ATG-FRT cassette located in the SBT/SV40-FGIP transposon (FIG. 2B).

Figure 6:
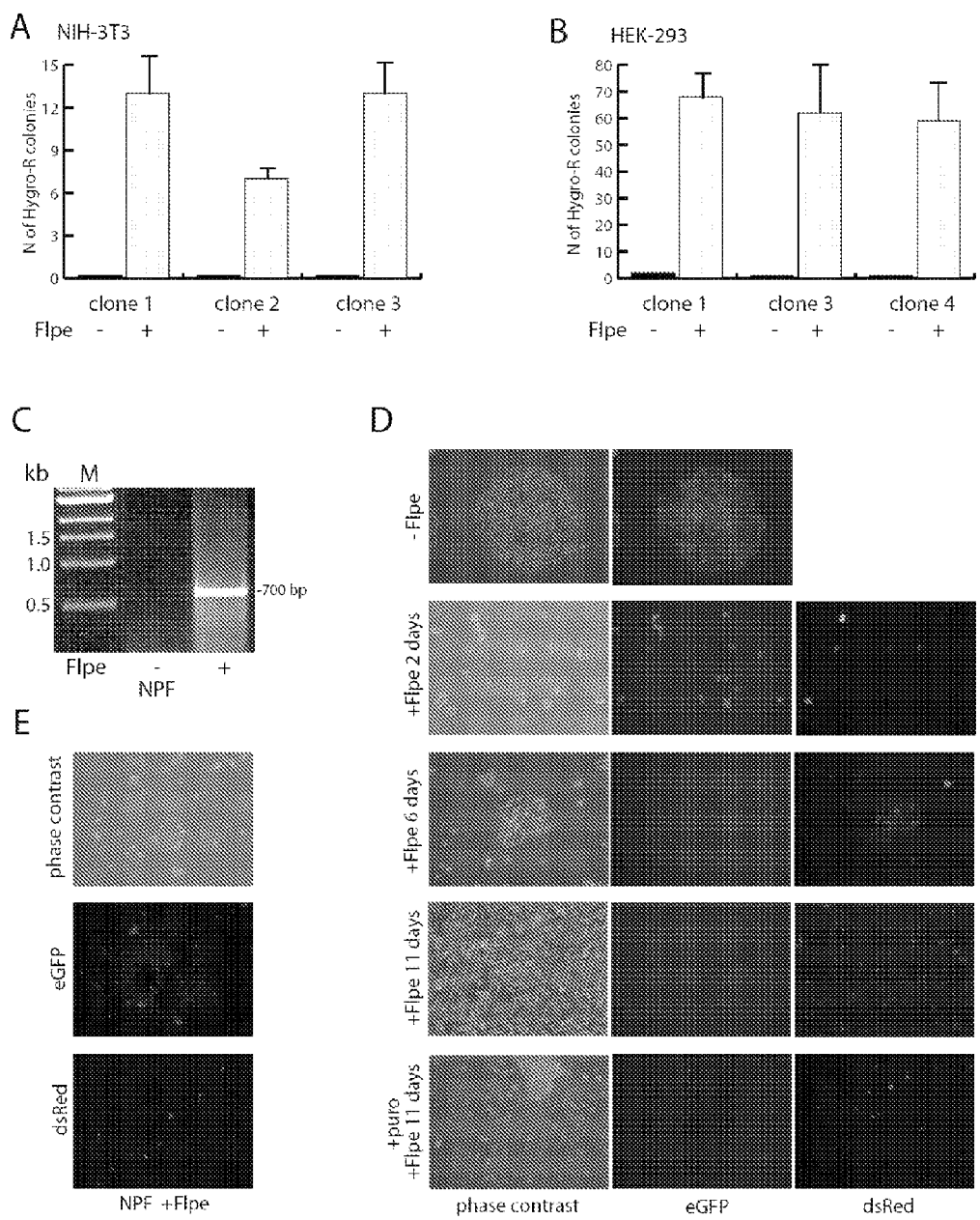
FIG. 6 shows substitution of transgenes by Flp-mediated recombination. A) and B). Flp-based gene insertion into integrated SB docking vector. NIH3T3 and HEK293 cell lines derived from pSBT/SV40-FGIP-mediated transgenesis (seeded at $8 \times 10^5$ cells/dish) were re-transfected with the FRT donor plasmid in the presence (+) or absence (−) of plasmid DNA encoding the Flp recombinase. The number of hygromycin B-resistant colonies was counted. The cell clones used were in A) derived from NIH-3T3 cells and in B) from HEK293 cells. C) Flp-mediated recombination is possible in NPFs. To identify Flp-mediated recombination event in NPFs, cellular DNA was purified from cells co-transfected with the FRT donor plasmid and the Flp expression vector and from control cells with the donor plasmid but lacking Flp expression. A PCR amplification was performed with a forward primer located downstream of LIR in pSBT/SV40-FGIP transposon and a reverse primer at the beginning of the hygromycin B gene located in the donor plasmid. Molecular weight markers are shown to the left. D) Fluorescence analysis of Flp-mediated gene shifting. Cells from HEK-293 clone 4 containing the SBT/SV40-FGIP transposon were re-transfected with the FRT donor plasmid and the Flp expression vector. After the indicated number of days the presence of green fluorescence and red fluorescence was determined by epifluorescence analysis of cell clones obtained under hygromycin B selection. The upper two panels (labelled '-Flp') show the HEK-293 cell clone used in the analysis. In the bottom part, puromycin selection was re-introduced resulting in cellular death. E) Fluorescence analysis of Flp-mediated gene shifting in NPFs. Experimental conditions were as described in D).

At first, we examined for the occurrence of hygromycin B-resistant clones after selection for recombination. To test the functionality of the recombination system we addressed the recombination in NIH3T3 and HEK293 cells which are well-characterized for Flp-mediated recombination. Cells derived from three different NIH3T3 clones containing the SBT/SV40-FGIP transposon were analyzed. For all three cell lines a Flp-dependent occurrence of hygromycin B-resistant colonies was observed, indicting that the correct recombination event was possible in the context of the inserted transposon (FIG. 6A). A similar experiment in HEK293 cells also showed a Flp-dependent appearance of hygromycin B-resistant colonies (FIG. 6B). Thus, recombinase-mediated insertion of the hygromycin B resistance gene is possible in the context of the vectors used. Coupled to insertion of the hygro$^R$ gene is the removal of the puromycin resistance gene from the promoter sequence and the flanking ATG-start codon. Thus, Flp-mediated recombination should result in sensitivity towards puromycin selection of the cells. Indeed, in HEK-293 cells we observed that the cells became sensitive to puromycin after Flp-mediated recombination (data not shown). To substantiate the data concerning Flp recombination we identified the transposon insertion site in one of clones by ligation-mediated PCR. Using primers flanking the borders of the inserted FRT/hygro plasmid, we could verify precise insertion into the FRT site of the inserted SB transposon (data not shown).

In NPFs, we were unable to detect the formation of hygromycin B-resistant colonies in a colony-forming assay. However, we note that this cannot be attributed to the lack of the correct recombination but is a consequence of the lack of sufficient cell passage potential of these primary cells, which already had been through one round of selection. As an alternative approach, we performed a PCR analysis on genomic DNA of transfected NPFs to screen for the presence of insertions at an early stage before colony formation. The PCR analysis was performed on isolated genomic NPF DNA with a forward primer within the left IR of the SBT/SV40-FGIP transposon and a reverse primer in the hygro$^R$ gene. This primer combination should amplify a 700-bp fragment only if the recombination event has happened. Indeed such a fragment could be amplified from transgenic NPF cells co-transfected with the donor plasmid and the vector expressing Flp (FIG. 6C). In cells which were transfected with FRT-donor plasmid only, we could not detect 700-bp band, indicating that this band is indeed a result of the specific Flp-directed recombination event. Sequencing of this fragment confirmed that precise insertions mediated by Flp in NPFs had occurred with the expected sequence specificity within the FRT site. Thus, we conclude that NPFs can support Flp-mediated recombination with resulting alterations in transgene expression profiles.

In addition to selection marker exchange a Flp recombination event within the docking vector should result in a shift of expression from eGFP to DsRed. To monitor the presence of such a colour exchange, we examined a HEK-293-derived cell clone (clone 4) by epifluorescence analysis. Prior to transfection with the DsRed-encoding donor plasmid and the Flp expression vector, HEK-293 cells containing the integrated SBT/SV40-FGIP transposon showed a clear green fluorescent signal (FIG. 6D). Two days after transfection the cells expressed both DsRed and eGFP as a result of transient presence of the DsRed expression vector after transfection. Cells were grown under hygromycin B selection and at 6 and 11 days after transfection the eGFP signal had disappeared and only DsRed expression could be monitored, supporting the notion that expression of the eGFP and DsRed transgenes had been shifted within the integrated transposon of clone 4 (FIG. 6D, panel 1 through 5). Similarly, stable DsRed expression could be monitored in transfected transposon-tagged NPFs only when Flp had been present (FIG. 6E), although these cells could not form hygromycin B-resistant colonies due to their limited passaging potential.

Transgenic NPFs Give Rise to Viable Porcine Blastocysts

Figure 7:
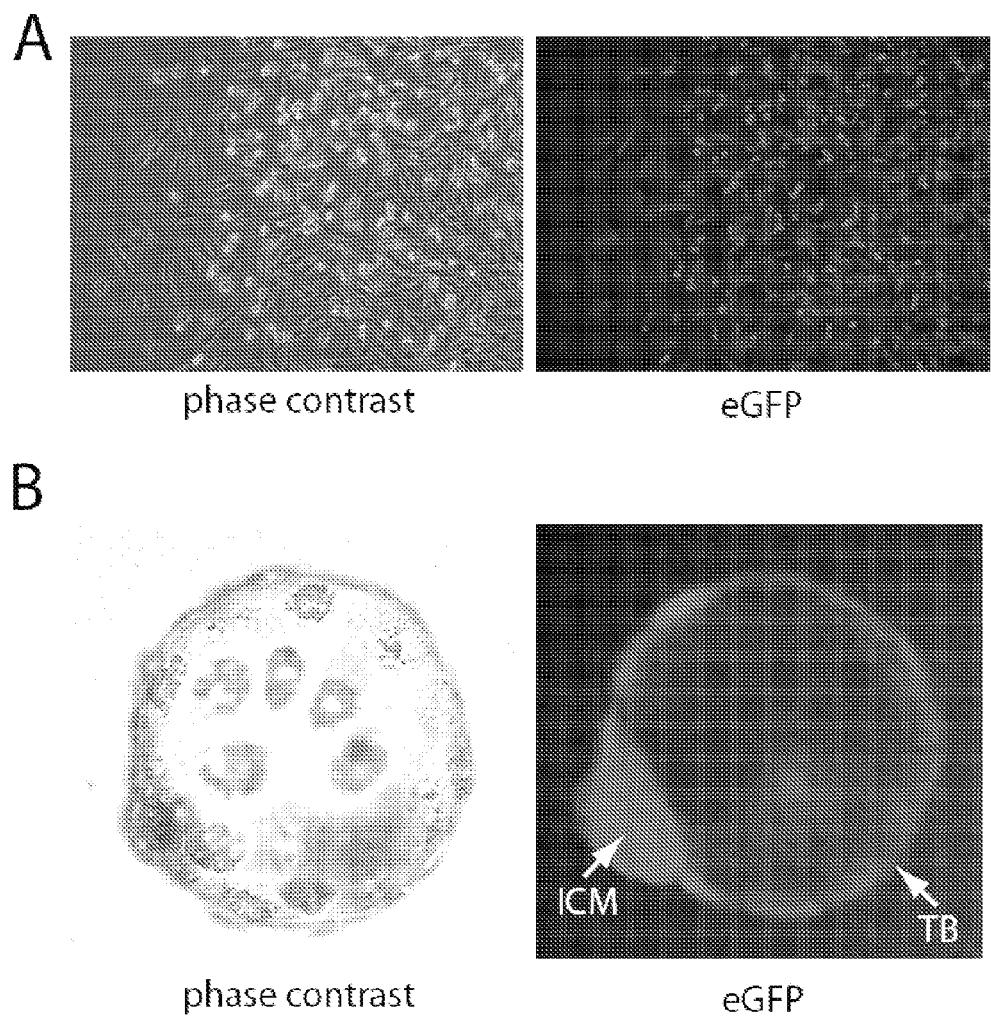
FIG. 7 shows that transgenic NPFs give rise to viable porcine blastocysts. A) Fluorescence analysis of the NPF colony used for nuclear transfer. The cell clone was derived from NPFs co-transfected with the pSBT/SV40-FGIP vector and the pCMV-HSB3.Topo plasmid coding for the hyperactive SB transposase. After selecting with puromycin for 9 days the cell clone was analyzed by microscopy and the cells subsequently propagated. B) SBT/SV40-FGIP-transgenic NPF cells give rise to viable blastocysts. A representative blastocyst derived by nuclear transfer from the cells shown in A) was analyzed by fluorescence microscopy. The green fluorescent colour is evident in the inner cell mass (ICM) and in the trophoblast (TB) layer in particular.

Due to the limited lifespan of the NPF cells, the porcine master cell line transgenic for the SBT/SV40-FGIP transposon could not be used for insertion of other transgenes in a second round of selection, and thus prevented us from demonstrating transgene insertion at a defined position in the NPF genome. Formal proof would therefore require generation of cloned 'master pigs' carrying the SBT/SV40-FGIP insertion and studies of gene insertion in primary cells derived from these pigs. We therefore examined the possibility of generating SBT/SV40-FGIP-transgenic animals from which cells with regained growth potential can be derived and used for Flp-mediated recombination and a subsequent second round of cloning. To this end we here addressed the question if transgenic NPFs have potential to generate transgenic blastocysts by the use of HMC-directed SCNT. After SB transposition using the pSBT/SV40-FGIP vector and selecting with puromycin for 9 days, NPF clones were isolated, expanded to about 1×10$^5$ cells and stored at −135° C. All clones expressed eGFP (FIG. 7A). Batches of cells were thawed and used for handmade cloning. Viable blastocysts were obtained. Fluorescent analysis showed that the blastocysts expressed eGFP in all cells (FIG. 7B). Thus, SBT/SV40-FGIP-transgenic NPFs are applicable for cloning by SCNT and expression of the transgene is maintained in both the inner cell mass and the trophoblast layer at the blastocyst stage of development.

Handmade Cloning (HMC) and Establishment of Pregnancies

Handmade cloning was performed as described herein. Briefly, oocytes with partially digested zona pellucida were enucleated by oriented bisection according to the position of the polar body. The part of the oocytes without chromatin, i.e. the cytoplasts, was collected and electrofused with transgenic NPFs. Another cytoplast was electrofused with each cytoplast-fibroblast pair during a second round of fusion which also activated the reconstructed embryos and transgenic blastocysts developed after 7 days of in vitro culture.

For the cloning and delivery of transgenic piglets, transgenic donor cells as described herein were used in HMC. Except where otherwise indicated all chemicals were obtained from Sigma Chemical Co. (St Louis, Mo., USA).

Oocyte Collection and In Vitro Maturation (IVM)

Cumulus-oocyte complexes (COCs) are aspirated from 2 to 6 mm follicles from slaughterhouse-derived sow ovaries and matured in groups of 50 in 400 µl IVM medium consisting of bicarbonate-buffered TCM-199 (GIBCO BRL) supplemented with 10% (v/v) cattle serum (CS), 10% (v/v) pig follicular fluid, 10 IU/ml eCG, 5 IU/ml hCG (Suigonan Vet; Skovlunde, Denmark) at 38.5° C. in 5% $CO_2$ in humidified air in the Submarine Incubation System (SIS; Vajta et al., 1997) for 41-44 h.

HMC is performed by a procedure based on partial digestion of the zona pellucida, as described earlier (Du et al., 2005 and 2007). Matured COCs was freed from cumulum cells in 1 mg/ml hyaluronidase in Hepes-buffered TCM-199. From this point (except where otherwise indicated) all manipulations are performed on a heated stage adjusted to 39° C., and all drops used for handling oocytes were of 20 µl covered with mineral oil. Zonae pellucidae of are partially digested with 3.3 mg/ml pronase solution dissolved in T33 (T for Hepes-buffered TCM 199 medium; the number means percentage (v:v) of CS supplement, here 33%) for 20 s, then oocytes are washed quickly in T2 and T20 drops. Oocytes with distended and softened zonae pellucidae are lined up in T20 drops supplemented with 2.5 μg/ml cytochalasin B. With a finely drawn glass pipette, oocytes are rotated to locate the polar body on the surface. By oriented bisection with an Ultra Sharp Splitting Blade (AB Technology, Pullman, Wash., USA) less than half of the cytoplasm close to the polar body is removed manually from the remaining putative cytoplast.

Transgenic donor fibroblasts grown to a confluent monolayer in DMEM supplemented with 10% FCS are trypsinized and kept in T20 (Kragh et al., 2004). Fusion is performed in two steps. For the first step, 50% of the available cytoplasts were transferred into 1 mg/ml of phytohemagglutinin (PHA; ICN Pharmaceuticals, Australia) dissolved in T0 for 3 s, then each one is quickly dropped over a single APPsw transgenic fibroblast. After attachment, cytoplast-fibroblast cell pairs are equilibrated in fusion medium (0.3 M mannitol and 0.01% PVA) for 10 s and transferred to the fusion chamber (BTX microslide 0.5 mm fusion chamber, model 450; BTX, SanDiego, Calif., USA). Using an alternating current (AC) of 0.6 kV/cm and 700 kHz, pairs are aligned to the wire of a fusion chamber with the somatic cells farthest from the wire, then is fused with a direct current of 2.0 kV/cm for 9 μs. After the electrical pulse, cell pairs are incubated in T10 drops to observe whether fusion has occurred.

Approximately 1 h after the first fusion, each pair is fused with another cytoplast and activated simultaneously in activation medium (0.3 M mannitol, 0.1 mM $MgSO_4$, 0.1 mM $CaCl_2$ and 0.01% PVA). By using an AC of 0.6 kV/cm and 700 kHz, one fused pair and one cytoplast is aligned to one wire of the fusion chamber, with fused pairs contacting the wire, followed by a single DC pulse of 0.85 kV/cm for 80 μs. When fusion is observed in T10 drops, reconstructed embryos are transferred into porcine zygote medium 3 (PZM-3; Yoshioka et al., 2002) supplemented with 5 μg/ml cytochalasin B and 10 μg/ml cycloheximide. After a 4 h incubation at 38.5° C. in 5% $CO_2$, 5% $O_2$ and 90% $N_2$ with maximum humidity, embryos are washed three times in PZM-3 medium before culture Embryo Culture and Transfer Embryos are cultured at 38.5° C. in 5% $CO_2$, 5% $O_2$ and 90% $N_2$ with maximum humidity in PZM-3 medium in the well of well system (WOWs; Vajta et al., 2000). Day 5 and 6 blastocysts with clearly visible inner cell mass are surgically transferred to Danish landrace sows on day 4 or 5 after weaning. Pregnancies are diagnosed by ultrasonography on day 21 and confirmed every second week. Piglets are delivered by Caesarean section on day 114, 24 h after treatment with prostaglandin F2.

Flp-Based Plasmid Insertion into Integrated SB Vectors

Figure 8:
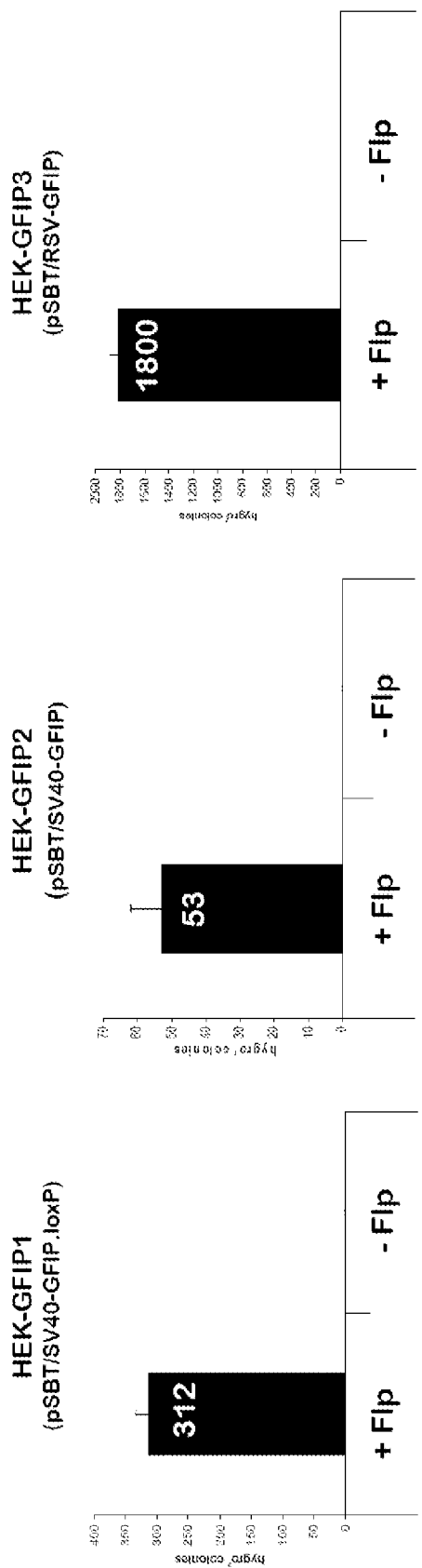
FIG. 8 To facilitate Flp-based gene insertion into integrated SB vectors HEK-GFIP1, HEK-GFIP2, and HEK-GFIP3 were co-transfected with pcDNA/FRT (containing the FRT-hygro fusion gene) and pCMV-Flpx9. Upon subsequent hygromycin B selection 312, 53, and 1800 drug-resistant colonies appeared in the three cell lines shown in FIG. 3.

To facilitate Flp-based gene insertion into integrated SB vectors HEK-GFIP1, HEK-GFIP2, and HEK-GFIP3 were co-transfected with pcDNA/FRT (containing the FRT-hygro fusion gene) and pCMV-Flpx9. Upon subsequent hygromycin B selection 312, 53, and 1800 drug-resistant colonies appeared in the three cell lines. (FIG. 8). Notably, for each of the three cell lines co-transfection with pUC19 instead of pCMV-Flpx9 did not result in colony formation, indicating that there was no background of false positives in the system. Subsequent PCR and sequence analysis confirmed correct Flp-based gene insertion (data not shown). We are currently investigating whether the variable number of hygromycin B-resistant colonies obtained is a result of different properties of the transposons used or perhaps variable SB copy numbers in the three cell lines.

Vector construction and procedure: The target transposon SBT/RSV-GFIP was inserted into the genome of HEK-293 cells by co-transfecting (using Fugene-6 from Roche) 1.5 μg pSBT/RSV-GFIP with 1.5 μg pCMV-SB (or 1.5 μg pCMV-mSB as a negative control). pCMV-SB, obtained from Perry Hackett, University of Minnesota, Minnesota, USA, encodes the Sleeping Beauty transposase reconstructed from fossil DNA transposable elements of salmoid fish. SB-tagged cell clones were generated by selecting transfected cells with puromycin (1 μg/ml). Clones were isolated and expanded and utilized as target clones for Flp-mediated gene insertion. To demonstrate site-specific insertion of transfected plasmid DNA 12 μg pCMV-Flp was co-transfected (by $CaPO_4$) with either (i) 3 μg pcDNA5/FRT or (ii) 3 μg pLV/FRT-hygro.PGK-puro into SBT/RSV-GFIP-tagged HEK-293 cells. To select for site-specific insertions cells were grown in medium containing hygromycin B (200 μg/ml).

Gene-Flanking Insulators Stabilize Gene Expression from Integrated Transposons.

In ongoing work we have demonstrated that expression from integrated SB-vectors, depending on the site of integration, can be transcriptionally silenced over time. Such silenced vectors can be re-activated by treating vector-containing cells with 5-azacytidine or trichostatin A indicating that epigenetic changes at the targeted locus are responsible for silencing. Based on these findings we flanked the gene expression cassette of these vectors with cHS4 insulators and monitored the effect on gene expression stability. Interestingly, we found in transposition assays, carried out in F9 embryonal carcinomal cells, that insulation of the PGK-puro cassette inside these transposons resulted in a dramatic 5-fold increase in the number of puromycin-resistant colonies compared to numbers achieved with un-insulated vectors (data not shown). These data strongly indicate that insulators stabilize gene expression from transposed SB vectors and therefore insulators are included in a novel generations of FRT-tagged SBT/GFIP vectors.

Figure 4:
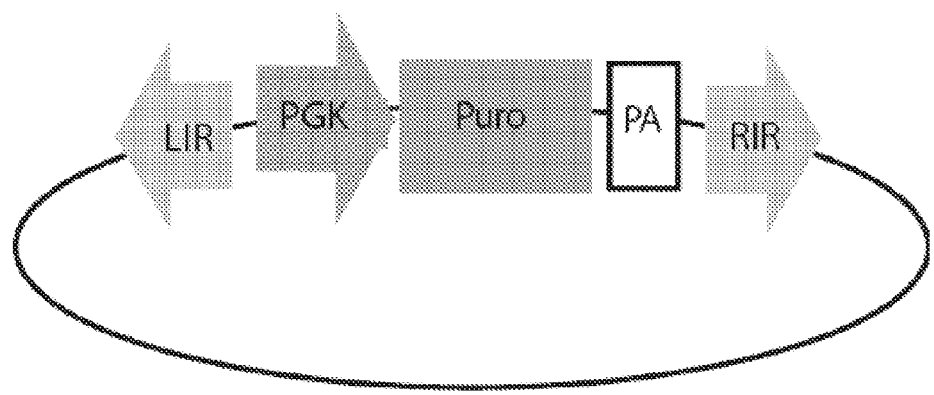
FIG. 4 shows Sleeping Beauty transposition in porcine fibroblasts. A) Schematic description of the pSBT/PGK-puro plasmid used to examine the potential of SB transposons for transgenesis in neonatal pig fibroblasts (NPFs). A puromycin resistance gene driven by the PGK promoter is flanked by LIR and RIR sequences. B) NPFs support SB transgenesis. $2.6 \times 10^4$ NPFs were co-transfected with pSBT/PGK-puro and with plasmid DNA encoding one of the following three variants of SB transposase: mSB which represents an inactive transposase variant, SB10 which is the original SB transposase, and HSB3 which is a hyperactive transposase variant. The experiments were carried out in triplicates and the number of cell colonies was counted after 9 days of puromycin selection.
Figure 4:
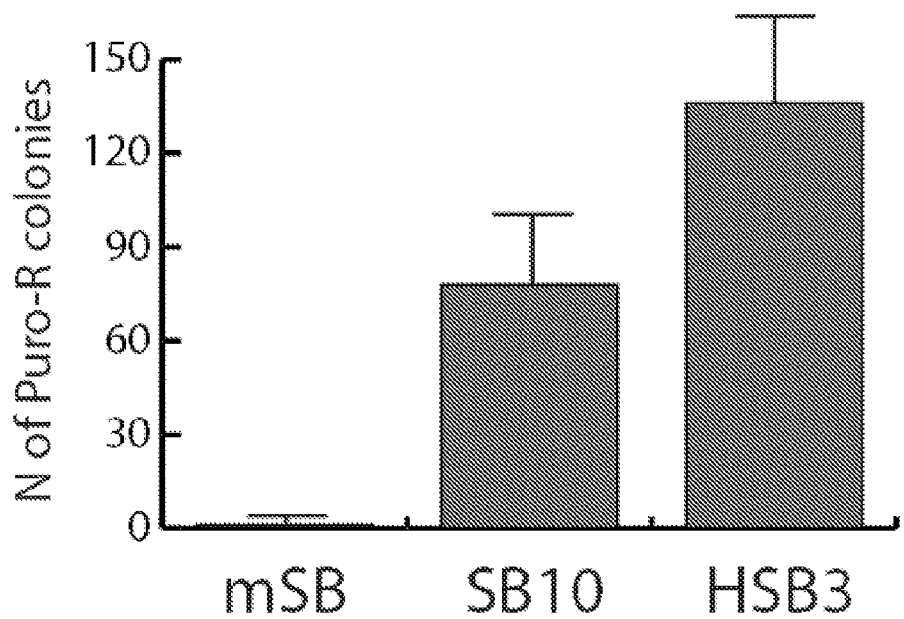
Figure 9:
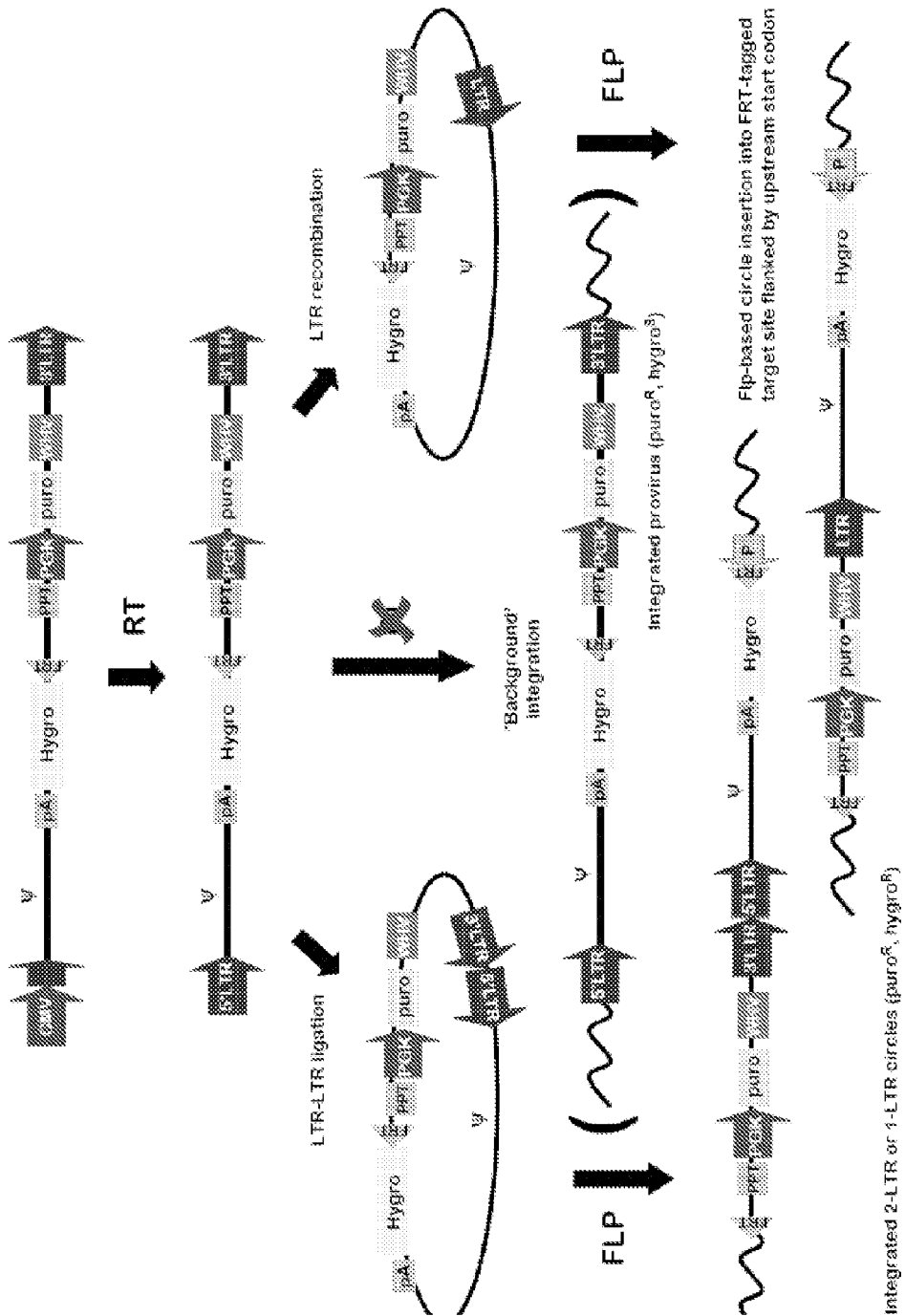
FIG. 9 shows a schematic representation of circular DNA intermediates that are generated during lentivirus infection and which are often considered dead-end reverse-transcribed products of infection. 2-LTR DNA circles are generated by DNA repair and ligation of the full-length linear viral DNA (FIG. 4, left), whereas 1-LTR DNA circles are generated by homologous recombination between the two LTRs of the episomal and linear viral DNA (FIG. 4, right). We hypothesized that these circles, generated during lentiviral vector transduction, may support Flp-based recombination, allowing site-specific integration of DNA circles devoid of bacterial sequences (FIG. 4, bottom)

Strategies for Flp-based insertion of circular virus-derived substrates. As long as genetically engineered cells are easy to transfect supercoiled plasmid DNA is an efficient substrate for Flp-based gene insertion into the genome. To facilitate site-specific gene insertion in hard-to-transfect cell lines or tissues that are not easily transfected in vivo we wanted to explore alternative substrates for site-specific recombination. We focused on circular DNA intermediates that are generated during lentivirus infection and which are often considered dead-end reverse-transcribed products of infection. 2-LTR DNA circles are generated by DNA repair and ligation of the full-length linear viral DNA (FIG. 9, left), whereas 1-LTR DNA circles are generated by homologous recombination between the two LTRs of the episomal and linear viral DNA (FIG. 4, right). We hypothesized that these circles, generated during lentiviral vector transduction, may support Flp-based recombination, allowing site-specific integration of DNA circles devoid of bacterial sequences (FIG. 9, bottom).

Figure 10:
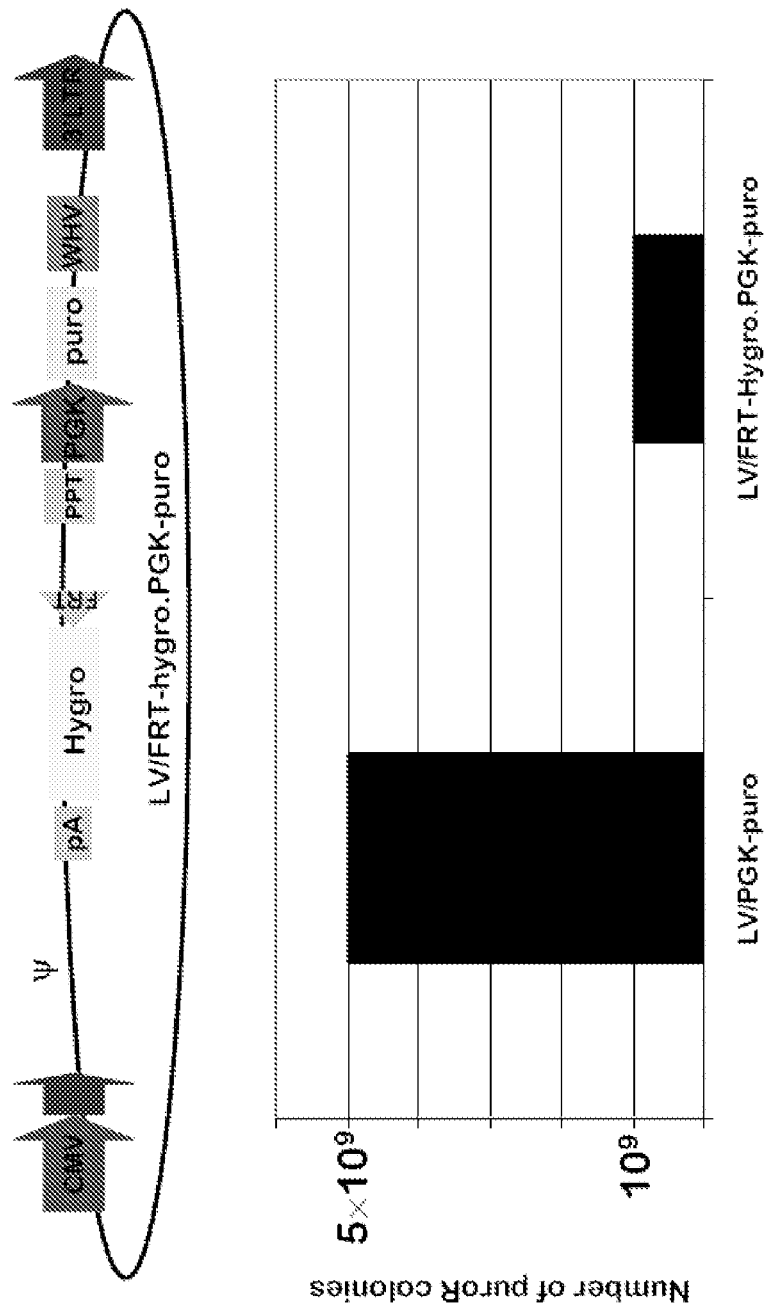
FIG. 10 To maximize circle formation and accumulation we generated integration-defective lentiviral vectors (ID-LVs) which contained a mutated inactive integrase protein. We generated a lentiviral vector, pLV/FRT-hygro.PGK-puro, that contains the FRT-hygro recombination sequence and found in transduction titer assays that this vector was only slightly less efficiently transferred in comparison to the original vector
Figure 11:
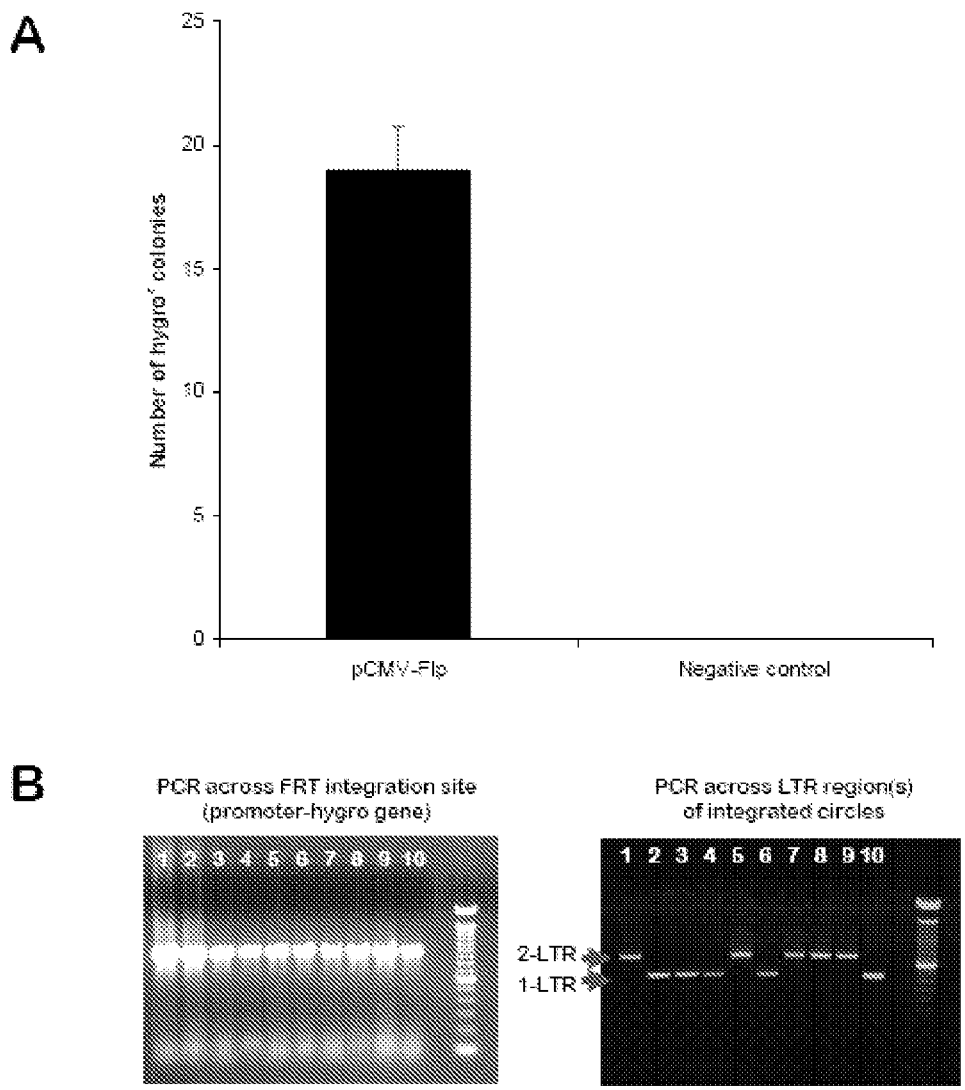
FIG. 11 shows HEK-GFIP3 cells were transfected with pCMV-Flpx9 and on the following day transduced transfected cells with ID-LV/FRT-hygro.PGK-puro at a MOI~100. Based on transfection and transduction of about $10^7$ cells, we obtained in triplicate assays on average approximately 20 hygromycin B-resistant colonies (FIG. 6A). Background activity was not registered in cells transfected with pUC19 prior to ID-LV/FRT-hygro.PGK-puro-transduction. PCR amplifications using as template genomic DNA from 10 of the hygromycin B-resistant colonies verified that DNA circles had been inserted site-specifically into SB-tagged loci (FIG. 6B). PCR across the FRT integration site resulted in band sizes indicative of specific gene insertion, whereas primers that amplified sequences containing the LTR region (s) of the integrated circles resulted in amplicons with either one or two LTRs (FIG. 6B)

1- and 2-LTR lentiviral DNA circles are efficient substrates for site-specific gene insertion. To maximize circle formation and accumulation we generated integration-defective lentiviral vectors (ID-LVs) which contained a mutated inactive integrase protein. We generated a lentiviral vector, pLV/FRT-hygro.PGK-puro, that contains the FRT-hygro recombination sequence and found in transduction titer assays that this vector was only slightly less efficiently transferred in comparison to the original vector (FIG. 10). We then transfected HEK-GFIP3 cells with pCMV-Flpx9 and on the following day transduced transfected cells with ID-LV/FRT-hygro.PGK-puro at a MOI~100. Based on transfection and transduction of about $10^7$ cells, we obtained in triplicate assays on average approximately 20 hygromycin B-resistant colonies (FIG. 11A). Background activity was not registered in cells transfected with pUC19 prior to ID-LV/FRT-hygro.PG K-puro-transduction.

PCR amplifications using as template genomic DNA from 10 of the hygromycin B-resistant colonies verified that DNA circles had been inserted site-specifically into SB-tagged loci (FIG. 11B). PCR across the FRT integration site resulted in band sizes indicative of specific gene insertion, whereas primers that amplified sequences containing the LTR region (s) of the integrated circles resulted in amplicons with either one or two LTRs (FIG. 11B). Hence, 1-LTR and 2-LTR integrations each were detected in 5 separate clones. We conclude that lentiviral DNA circles can act as substrates for Flp-based site-specific recombination.

Figure 12:
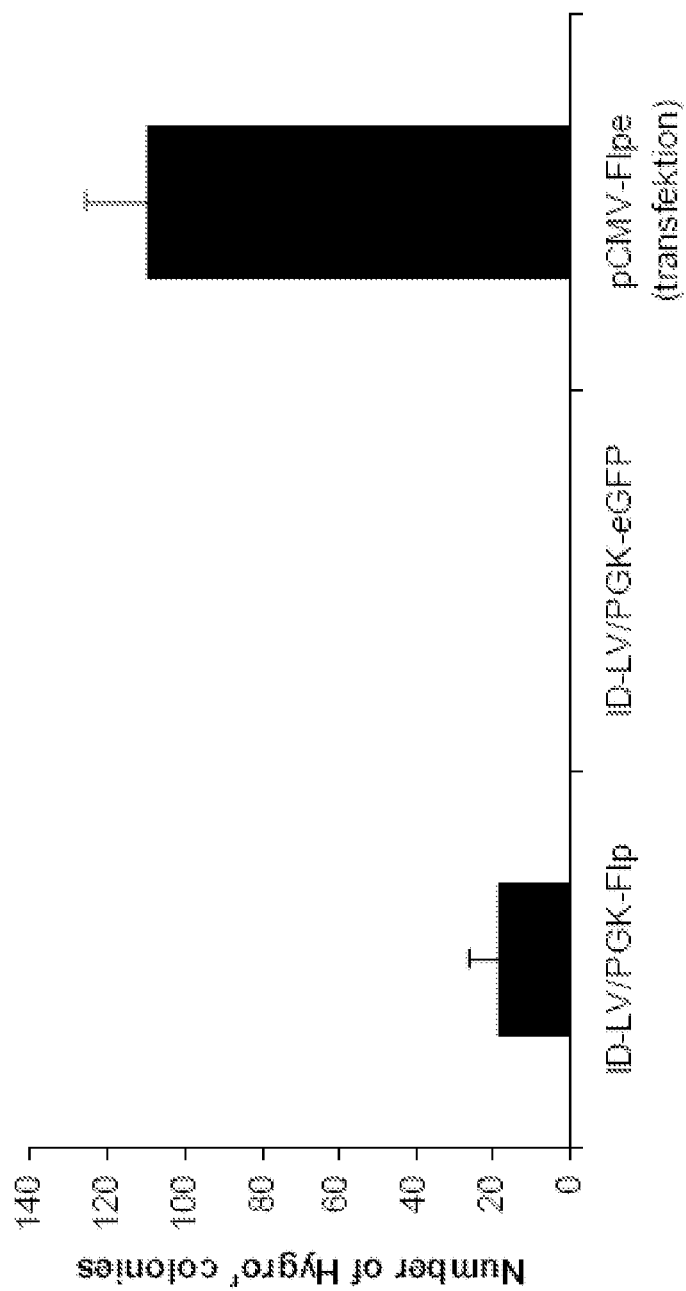
FIG. 12 shows triplicate assays using the indicated substrates.

ID-LV-encoded Flp supports Flp-based gene insertion. Based on this finding we set out to test whether Flp likewise could be delivered by ID-LVs. We therefore generated a lentiviral vector, pLV/PGK-Flp containing a PGK-driven Flp gene and transduced HEK-GFIP3 cells with ID-LV/PGK-puro at a MOI~100. Twenty four hours post-transduction cells were transfected with a FRT-tagged plasmid substrate (pcDNA5/FRT) and then treated with hygromycin B. Again, we detected in triplicate experiments about 20 drug-resistant colonies (FIG. 12). In comparison, transfection with pCMV-Flpx9 resulted in about 100 colonies, whereas transduction with a Flp-less vector, ID-LV/PGK-eGFP, did not result in colony formation. Flp-dependent colony formation in this assay indicates that Flp, generated from ID-LVs, is sufficient to confer substrate recombination and site-specific gene insertion.

ID-LV Co-Transduction Results In Site-Specific Lentiviral DNA Circle Insertion.

Figure 13:
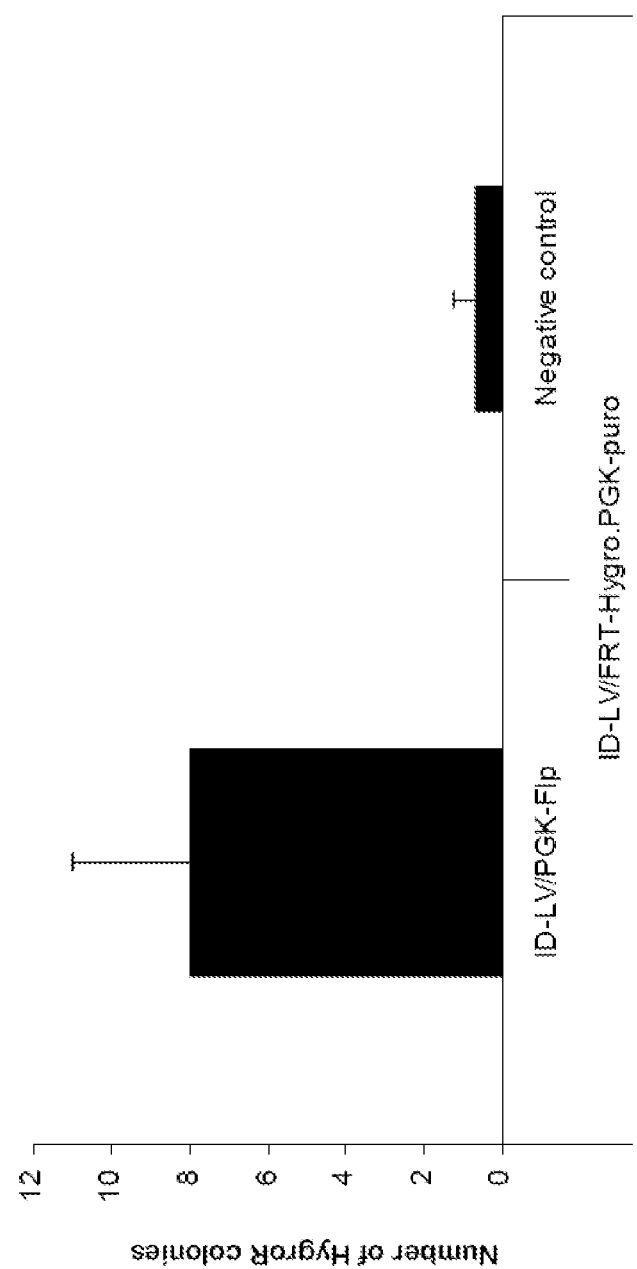
FIG. 13 ID-LV co-transduction results in site-specific lentiviral DNA circle insertion.

We finally combined the actions of ID-LV/FRT-hygro and ID-LV/PGK-Flpx9 vectors in one experiment by co-transducing HEK-GFIP3 cells and selecting transduced cells for hygromycin B resistance. In this setup we obtained on average 8 colonies per transduction (FIG. 13), demonstrating that Flp encoded by an integrating-defective vector facilitates insertion of lentiviral DNA circles carrying the Flp recognition sequence. This finding demonstrates for the first time site-specific insertion of lentiviral vectors and confirm that DNA circles generated during lentiviral transduction may serve as substrate for genomic integration. By integrating viral circles rather than plasmid DNA, we obtain insertions that are not potentially harnessed by bacterial sequences derived from the plasmid backbone and, moreover, pave the way for Flp-based gene insertions in hard-to-transfect cell lines or tissues.

Transduction of Cells with Integration-Proficient and -Deficient Lentiviral Vectors.

VSV-G-pseudotyped lentiviral vectors were generated by co-transduction of 293T cells with 13 µg pMDGPLg/RRE, 3 µg pRSV-Rev, 3.75 µg pMD2G, and 13 µg lentiviral vector plasmid. Vector production plasmid were obtained from Dr. Aebischer, Swiss Federal Institute of Technology, EPFL, Lausanne, Switzerland. Integration-defective lentiviral vectors (ID-LV) were generated by replacing pMDGPLg/RRE with pMDLg/pRREintD64V (obtained from Rafael Yáñez-Muñoz, University College London, UK) in the transfection mixture. pMDLg/pRREintD64V contains a point mutation in the integrase coding sequence rendering the encoded integrase inactive (14). Transduction titers of integration-proficient lentiviral vectors carrying the PGK-puro cassette were determined by transferring serially diluted supernatant from transfected 293T cells to HEK-293 target cells prior to puromycin selection. Maximal levels of lentiviral DNA circles were obtained by transducing SB-tagged target clones with ID-LVs at estimated MOIs of 100-500. In experiments involving transfected pCMV-Flp the cells were transfected one day prior to transduction with ID-LV/FRT-hygro.PGK-puro to ensure the presence of Flp at the time of circle formation. In the reciprocal experiment in which Flp was provided by lentiviral circles and plasmid DNA served as a substrate for recombination the cells were transduced with ID-LV/PGK-Flp one day prior to transfection. In ID-LV/FRT-hygro.PGK-puro+ID-LV/PGK-Flp co-transduction experiments the cells were simultaneously transduced with ID-LV/PGK-Flp and ID-LV/FRT-hygro.PGK-puro. After transfection/transduction of SBT/RSV-GFIP-tagged clones, cells were grown in medium containing hygromycin B. In selected experiments hygromycin B-resistant colonies were counted, isolated, expanded, and analyzed by insert-specific PCRs. PCRs included (i) selective amplification of sequences at the integration site and (ii) amplification of inserted 1- and 2-LTR sequences generated during lentiviral DNA circularization.

Construction of Alternative Vector and Transfer to Porcine Fibroblasts

The SB transposon-based vector used in this study was derived from the pSBT/SV40-GFIP.IoxP vector. This vector contains, within the context of a SB transposon, a bicistronic FRTeGFP-IRES-puro (GFIP) cassette flanked upstream by an ATG start codon and downstream by a poly A sequence. Moreover, the vector contains a recognition site for the Cre recombinase (IoxP) located between the upper inverted repeat of the vector and the SV40 promoter driving expression of the FRTeGFP-IRES-puro cassette.

Construction of pSBT/SV40-GFIP.IoxP Vector

Figure 14:
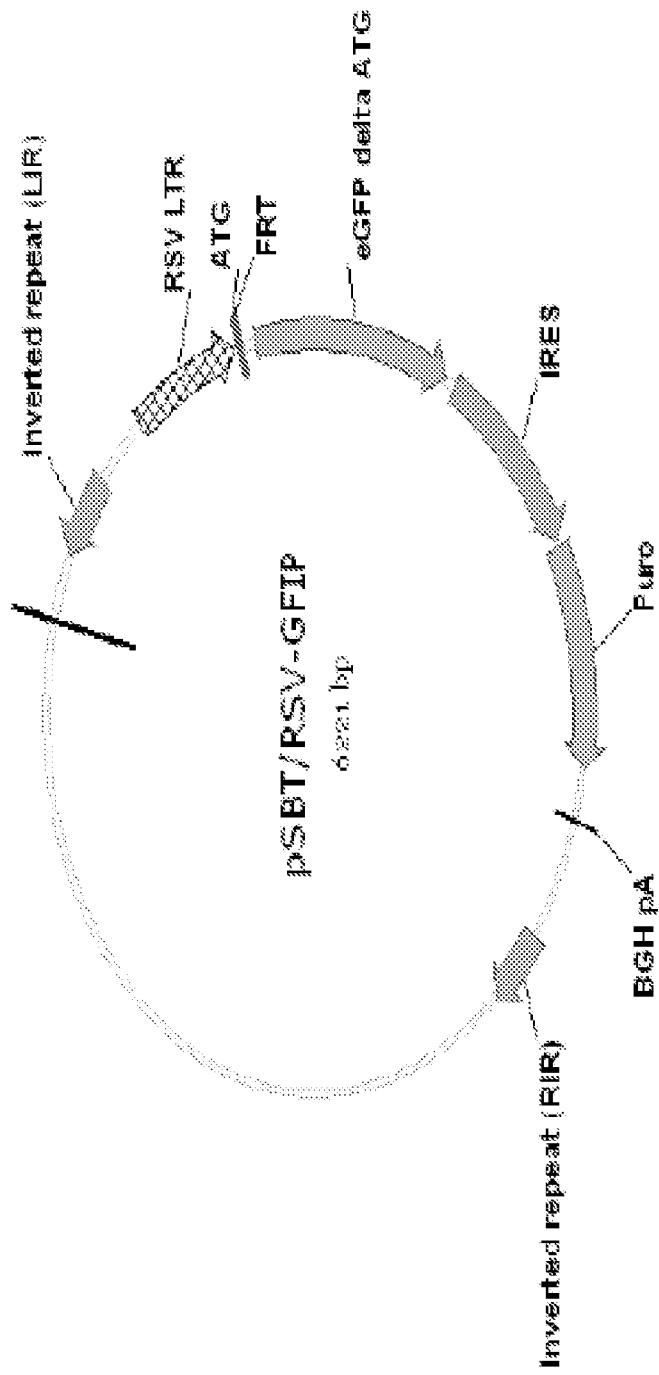
FIG. 14 shows a schematic representation of pSBT/RSV-GFIP.

The pSBT/RSV-GFIP vector contains the terminal inverted of the SB DNA transposon flanking a FRT-GFP.IRES.puro bicistronic gene cassette driven by a promotor derived from Rous sarcoma virus (RSV). The eGFP sequence was amplified from peGFP.N1 (Clontech) using a forward primer containing the 48-bp FRT sequence. To analyze FRT-GFP functionality, the FRT-eGFP fusion was inserted into an expression vector containing the SV40 promoter. The PCR-fragment containing FRT-tagged eGFP fusion gene was digested with MluI and XmaI and inserted into MluI/XmaI-digested pSBT/RSV-hAAT (pT/hAAT in ref. (8), obtained from Mark Kay, Stanford University, USA), generating a transposon vector with RSV-driven eGFP expression (pSBT/RSV-eGFP). An IRES-puro cassette was PCR-amplified from pecoenv-IRES-puro (provided by Finn Skou Pedersen, University of Aarhus, Denmark), digested with XmaI, and inserted into XmaI-digested pSBT/RSV-eGFP, generating pSBT/RSV-GFIP (see FIG. 14). Alternative versions of this vector containing the SV40 promoter (pSBT/SV40-GFIP) and the promoter derived from the human ubiquitin gene (pSBT/Ubi-GFIP), were generated. In addition, by inserting a Cre recombination target site (IoxP) into the MluI site located between the left inverted repeat of the transposon and the SV40 promoter of pSBT/SV40-GFIP, the vector pSBT/SV40-GFIP.IoxP was created. The donor plasmid pcDNA5/FRT, containing a FRT-hygro fusion gene without a start codon, was obtained from Invitrogen. The Flp-encoding plasmid, pCMV-Flp was obtained from A. Francis Stewart, University of California San Francisco, USA). This plasmid encodes the enhanced Flp variant designated Flpx9 (11). A SB-vector containing two copies of the 1.2-kb chicken DNase hypersensitive site 4 (cHS4)-derived insulator element (12, 13) was generated by inserting PCR-amplified cHS4 sequences and an intervening linker into NotI/SpeI-digested pSBT/PGK-puro (obtained from Mark Kay, Stanford University, USA). The PGK-puro cassette was cloned back into construct by using restriction sites located in the linker, generating pSBT/cHS4.PGK-puro.cHS4

For further use in pigs an alternative Cre recognition site (loxP-257) was inserted into a unique AscI site that was created by mutagenesis at a position located between the poly A sequence and the lower inverted repeat of the vector. This vector was designated pSBT/IoxP.SV40-GFIP.IoxP257. The presence of two Cre recombination sites allows Cre recombinase-mediated cassette exchange after Flp-based plasmid insertion, thereby facilitating, if needed, removal of plasmid sequences and selection genes.

SB Transposition in Primary Pig Fibroblasts

The SB transposon vectors, either SBT/PGK-puro or the target transposon SBT/IoxP.RSV-GFIP.IoxP257, were inserted into the genome of pig fibroblast by co-transfecting (using Fugene-6 from Roche) 1.5 µg pSBT/Iox.RSV-GFIP.IoxP257 (or pSBT/PGK-puro) with 1.5 µg pCMV-SB (or 1.5 µg pCMV-mSB as a negative control). pCMV-SB (rights held by Perry Hackett, University of Minnesota, Minnesota, USA) encodes the Sleeping Beauty transposase reconstructed from fossil DNA transposable elements of salmoid fish. pCMV-SB, pCMV-mSB, and the hyperactive variant pCMV-HSB3 were obtained from Mark Kay, Stanford University, USA. SB-tagged cell clones appeared as a result of selecting transfected cells with puromycin (0.5 µg/ml). Colonies were fixed and stained in methylene blue in methanol and subsequently counted.

Solid SB Transposition in Primary Pig Fibroblasts

Figure 15:
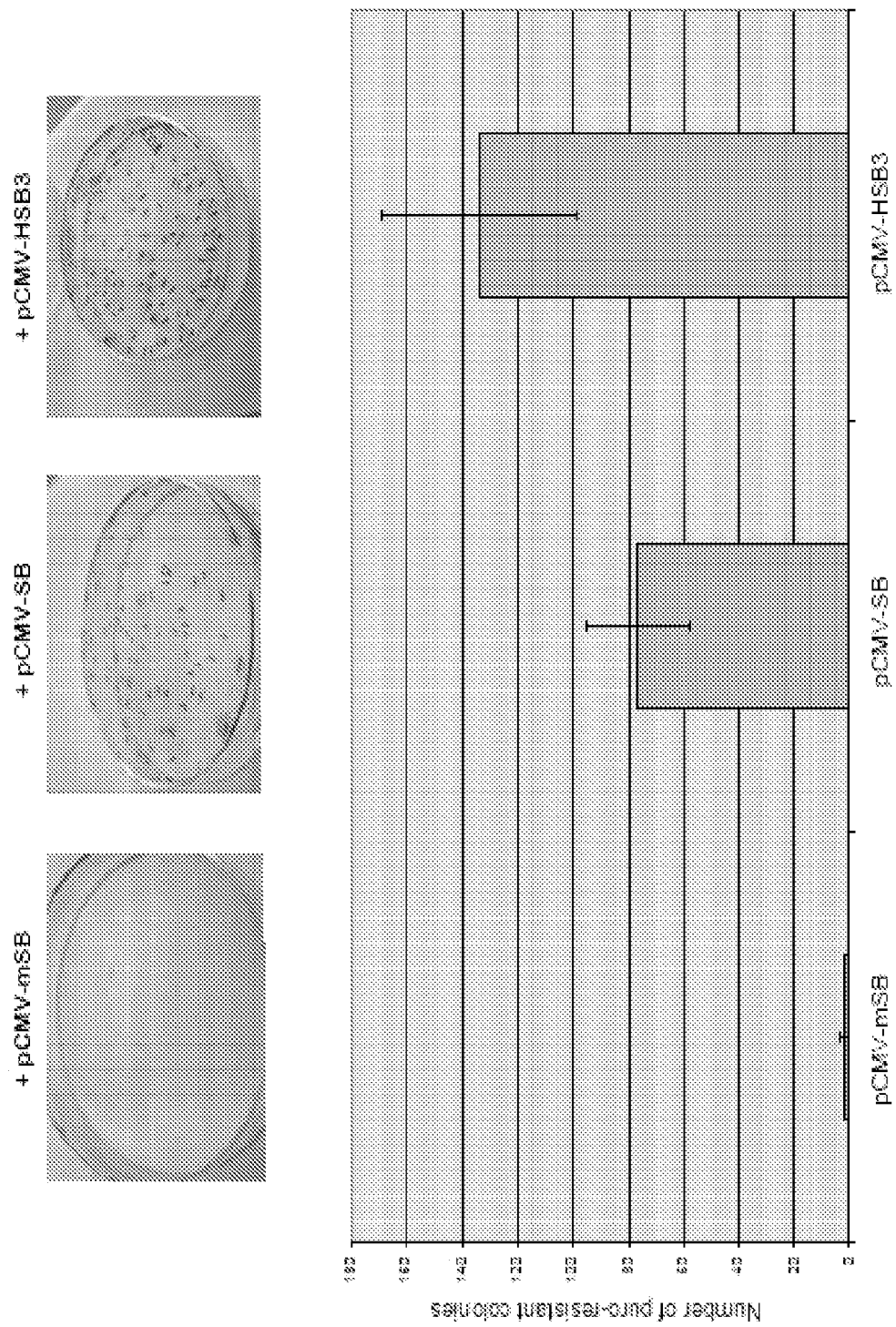
FIG. 15 shows transposition of SB vectors in porcine fibroblasts. A standard transposon encoding a puromycin resistance gene (SBT/PGK-puro) was employed and varying levels of transposition were detected, resulting in about 75 drug-resistant colonies in cultures of fibroblasts co-transfected with pSBT/PGK-puro and pCMV-SB, less than 3 colonies appeared after transfection with pSBT/PGK-puro and pCMV-mSB, the latter which encodes an inactive version of the transposase. Interestingly, a mean of almost 140 colonies was obtained using the hyperactive transposase variant HSB3, indicating that HSB3 also in porcine cells mediates higher levels of transposition compared to the original SB transposase.

SB transposes efficiently in most mammal cells but with higher efficacy in human cells than in murine cells. Transposition of SB vectors has never been analyzed in porcine cells, and we therefore initially tested activity in primary pig fibroblasts. We utilized a standard transposon encoding a puromycin resistance gene (SBT/PGK-puro) and found decent levels of transposition, resulting in about 75 drug-resistant colonies in cultures of fibroblasts co-transfected with pSBT/PGK-puro and pCMV-SB (FIG. 15). Less than 3 colonies appeared after transfection with pSBT/PGK-puro and pCMV-mSB, the latter which encodes an inactive version of the transposase. Interestingly, a mean of almost 140 colonies was obtained using the hyperactive transposase variant HSB3, indicating that HSB3 also in porcine cells mediates higher levels of transposition compared to the original SB transposase.

Efficient Insertion of a FRT-Tagged SB Vector in Pig Fibroblasts

Figure 16:
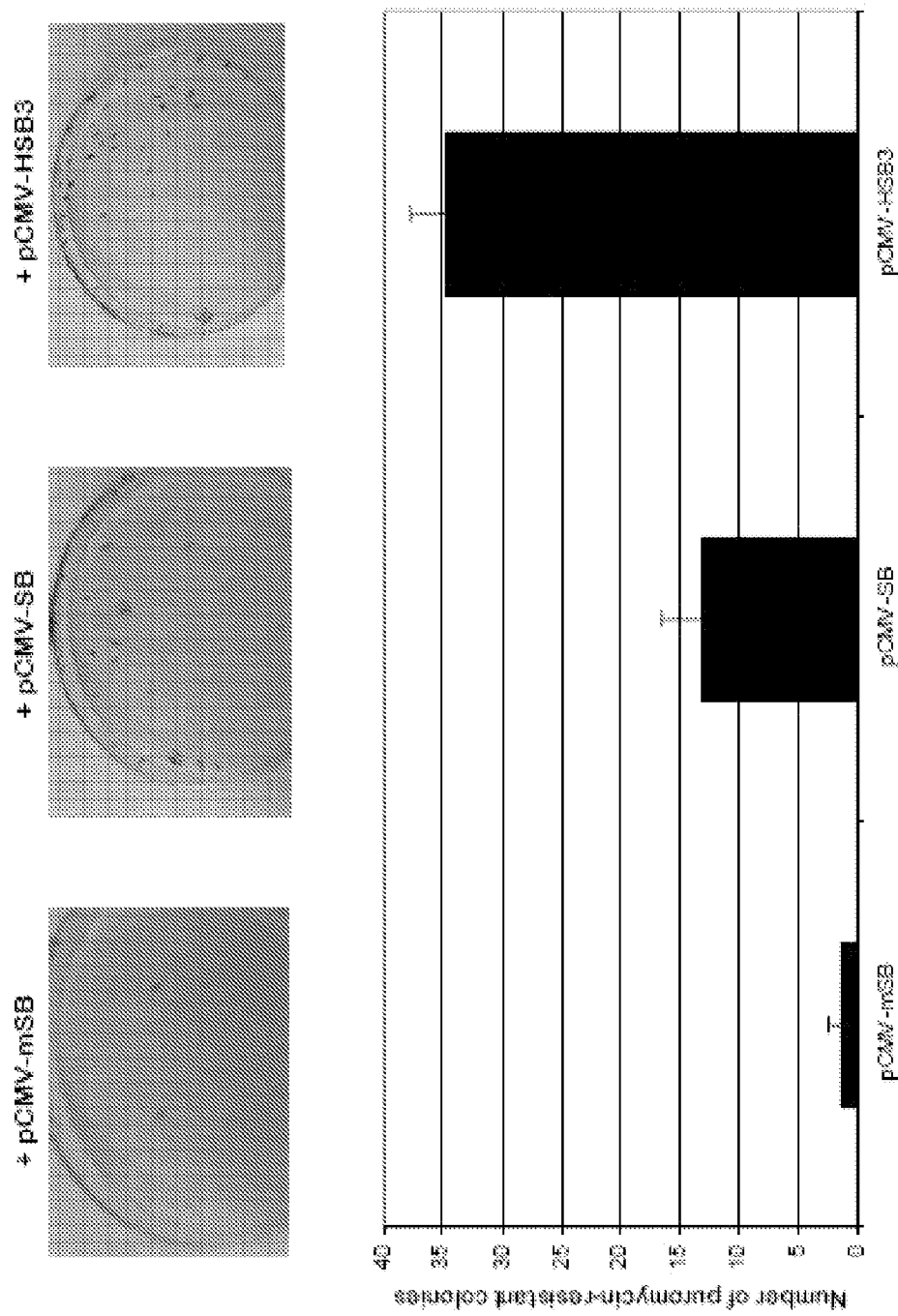
FIG. 16 shows efficient insertion of a FRT-tagged SB vector in pig fibroblasts SB-tagged cell clones containing a Flp recombination target site for site-specific gene insertion were co-transfected the pSBT/IoxP.SV40-lopP257 plasmid with pCMV-mSB, pCMV-SB, and pCMV-HSB3, respectively. HSB3 again showed the highest activity, resulting in about 30 drug-resistant colonies after transfection of 3 H $10^4$ fibroblasts.

To generate SB-tagged cell clones containing a Flp recombination target site for site-specific gene insertion, we co-transfected the pSBT/IoxP.SV40-lopP257 plasmid with pCMV-mSB, pCMV-SB, and pCMV-HSB3, respectively. HSB3 again showed the highest activity, resulting in about 30 drug-resistant colonies after transfection of 3H $10^4$ fibroblasts (FIG. 16).

Figure 17:
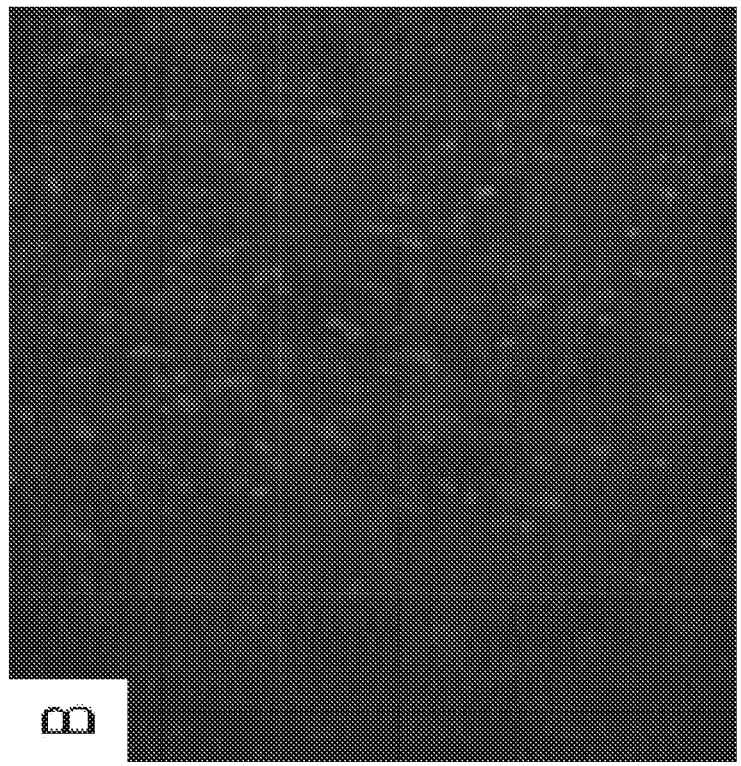
FIG. 17 shows clone analysis by fluorescence microscopy of isolated and expanded puromycin-resistant colonies demonstrates efficient FRTeGFP expression
Figure 17:
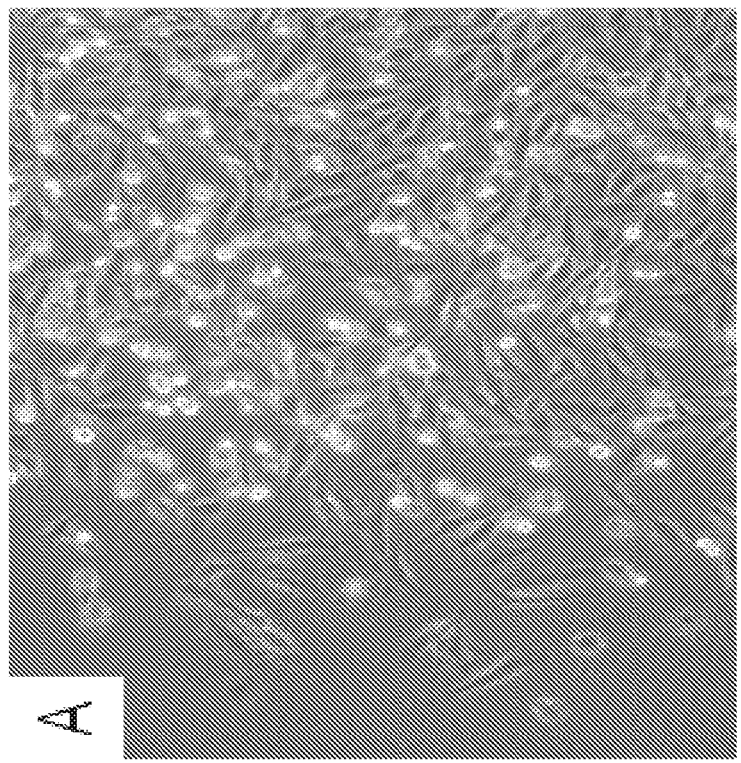

Puromycin-resistant colonies were isolated and expanded. Clone analysis by fluorescence microscopy demonstrated efficient FRTeGFP expression (FIG. 17), demonstrating vector functionality and easy FRTeGFP detection in pig fibroblasts. These fluorescent cell clones carrying the Flp FRT recombination sequence are currently being used for creation of cloned transgenic animals by hand-made cloning. Verification of SBT/IoxP.SV40-GFIP.IoxP257 as target for Flp recombination Due to limitations of long-term growth of primary pig fibroblasts in tissue culture we were not able to demonstrate Flp-based gene insertion into FRT-tagged SB vectors in pig fibroblasts. We therefore chose to test functionality of the FRT-containing vector by a standard set of recombination experiments carried out in HEK-293 cells. We generated clones of HEK-293 cells containing the transposed SBT/IoxP.SV40-GFIP.IoxP257 vector. By co-transfection of such clones with (i) a pcDNA5/FRT-derived substrate plasmid containing a FRT-hygro fusion gene and a red fluorescent protein (RFP) expression cassette and (ii) a plasmid encoding the Flp recombinase (pCMV-Flpx9), we subsequently identified hygromycin B resistant colonies. By fluorescence microscopy we observed that site-specifically engineered clones, as expected, turned-off eGFP expression and turned-on RFP expression (data not shown). This 'green-to-red' phenotypic change indicates that the integrated SB-derived target vector serves as acceptor site for Flp-based recombination.

Controlled Integration of Transgenes by Gene-Shifting

Figure 18:
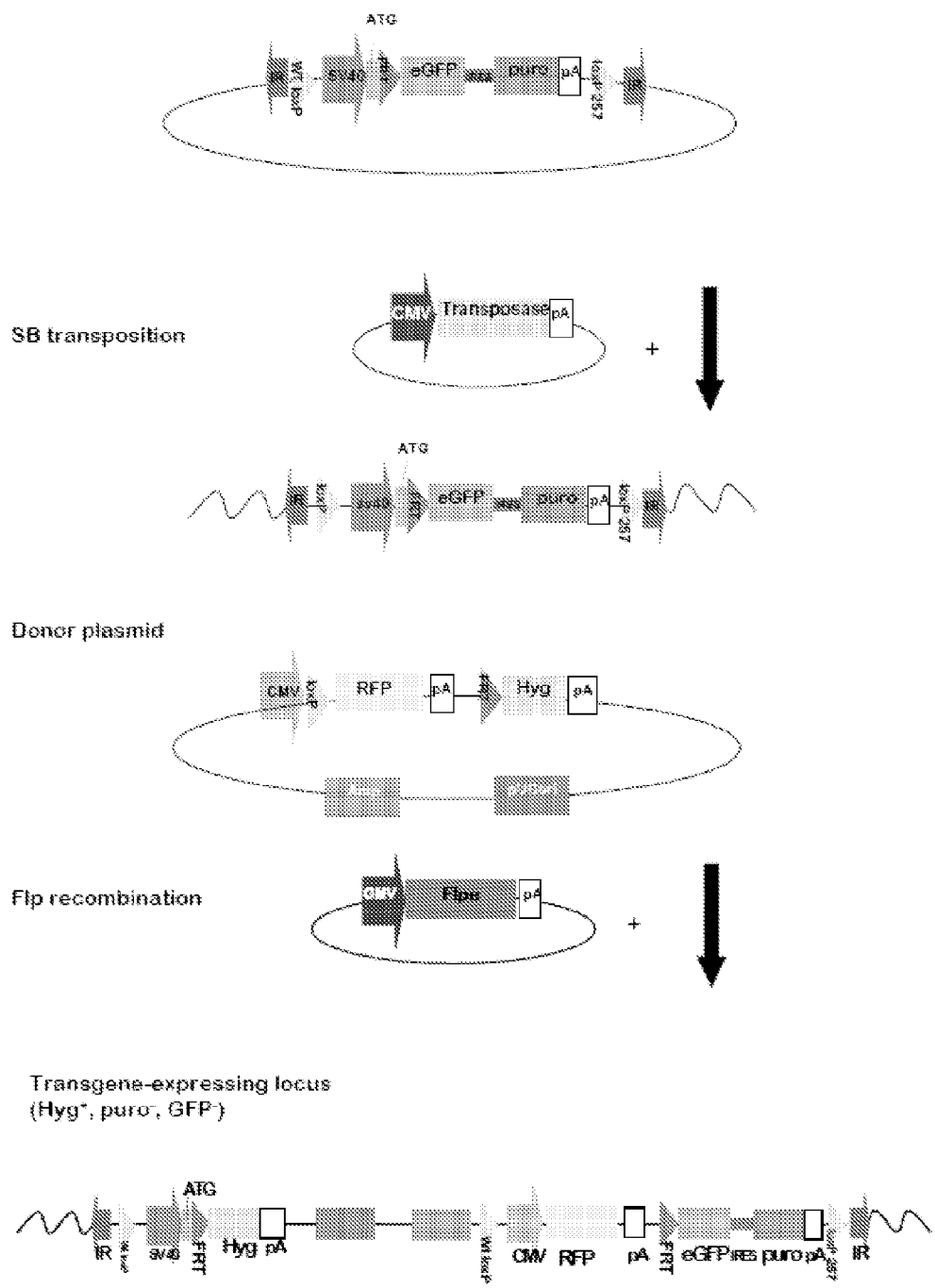
FIG. 18 shows a gene shift with the help of the Sleeping Beauty (SB) DNA transposon technology and Flpe recombination is presented in this example. We inserted into HEK 293 cells a SB transposon containing an eGFP gene and an frt site. The frt site enables gene shifting with a donor plasmid containing the RFP gene as well as an frt site.
Figure 19:
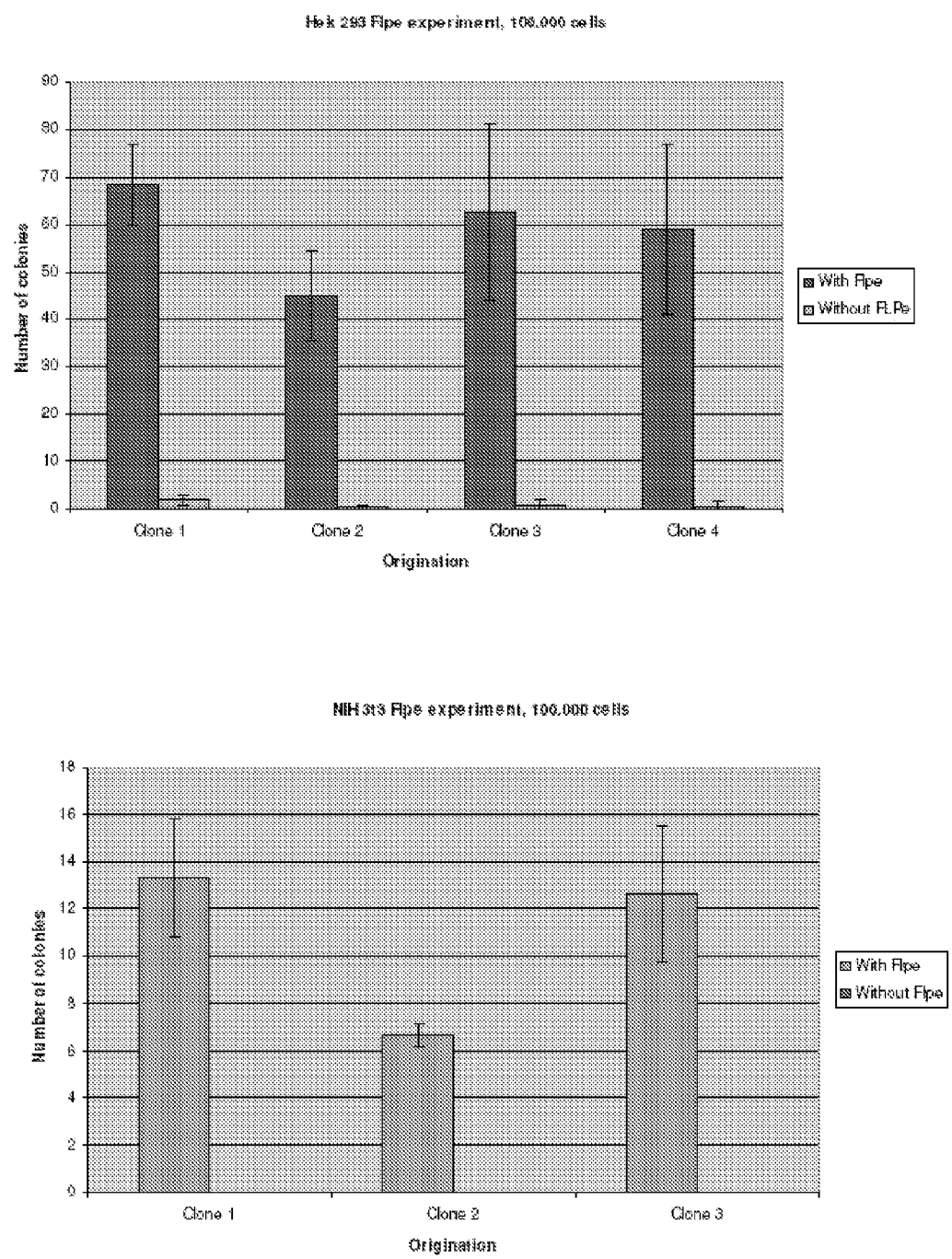
FIG. 19 shows gene shifts in HEK293 cells (upper panel) and NIH 3T3 cells (lower panel) with and without Flpe recombination.
Figure 20:
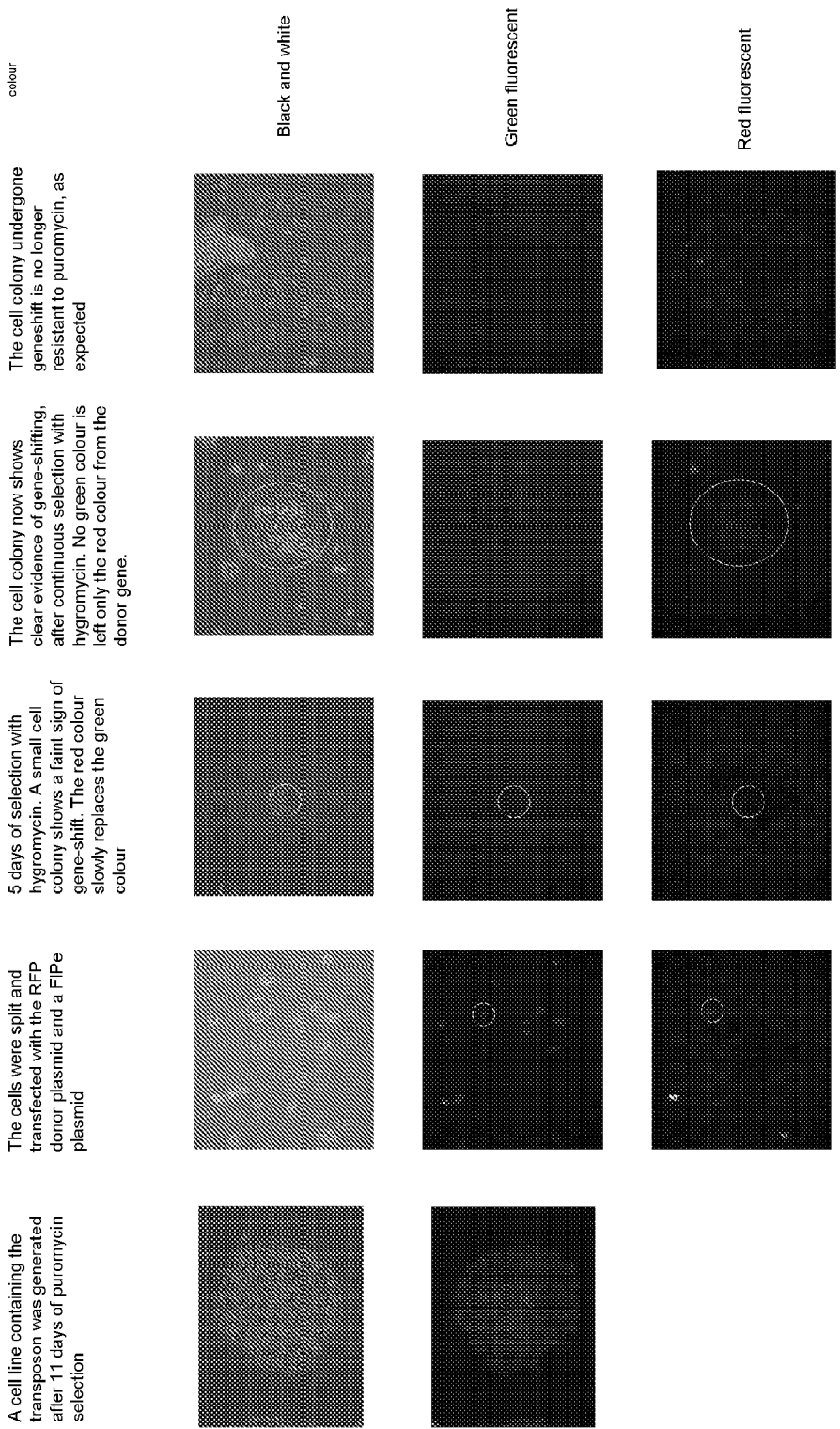
FIG. 20 shows a gene shift in HEK293 cells derived from clone 4. The eGFP gene linked to a puromycin resistant gene is shiftet with a RFP gene linked to a hygromycin gene.

A gene shift with the help of the Sleeping Beauty (SB) DNA transposon technology and Flpe recombination is presented in this example. We inserted into HEK 293 cells a SB transposon containing an eGFP gene and an frt site. The frt site enables gene shifting with a donor plasmid containing the RFP gene as well as an frt site (see FIG. 18). Cells which underwent complete gene shifting, changed colour from green to red fluorescence and also changed antibiotic resistance, as the eGFP is linked to a puromycin resistance gene, and the RFP to a hygromycine B resistance gene. One clone with such characteristics was examined by LM-PCR and the location of the transposon, including the eGFP and frt site was found on chromosome 10. The insertion site showed typical signs of SB integration in the form of TA duplication flanked by distinctive consensus sequences. The transposon was sequenced before and after gene shifting, which confirmed that the transposon was intact, initially without the RFP gene, and with RFP after gene shifting (FIGS. 19 and 20).

Figure 21:
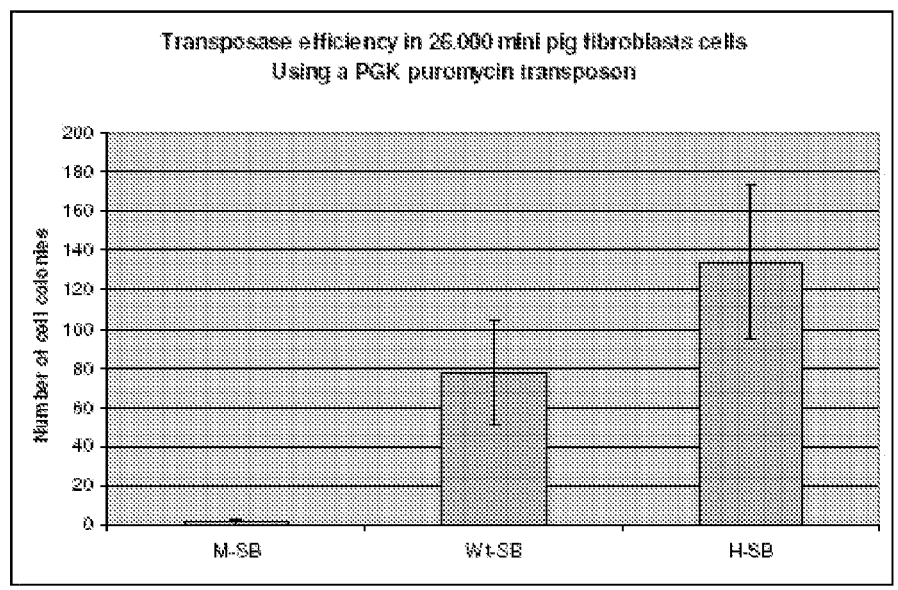
FIG. 21 top shows the transposase efficiency in fibroblast cells of a mini pig, using a PGK (phosphoglycerate kinase) promoter—puromycin transposon; lower diagram shows the transposase efficiency in fibroblast cells of a mini pig, using a modified GFIP transposon.
Figure 21:
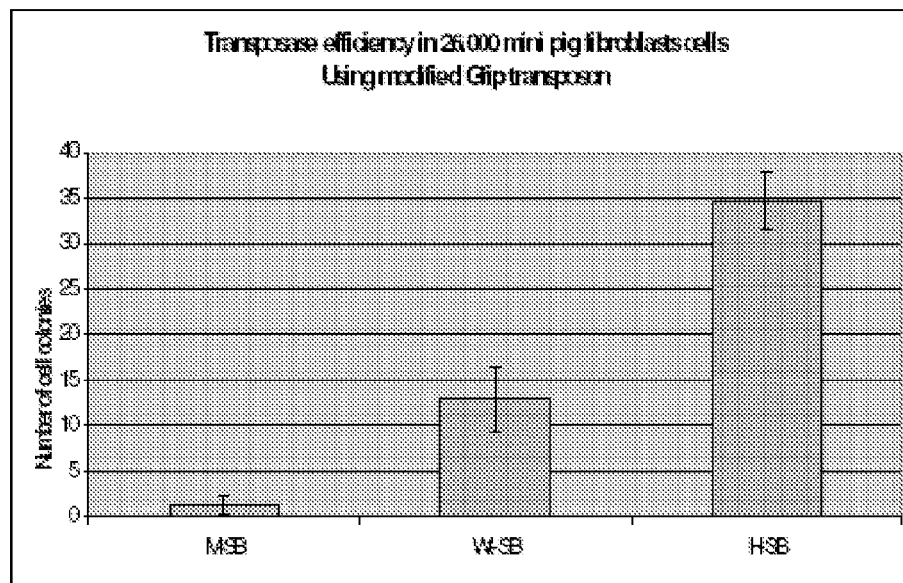
Figure 22:
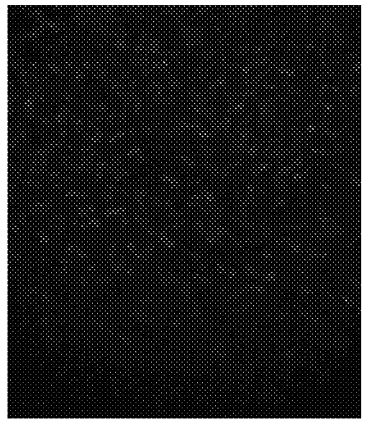
FIG. 22 shows viable cells and blastocysts comprising a transposon tagged genome carrying an eGFP gene.
Figure 22:
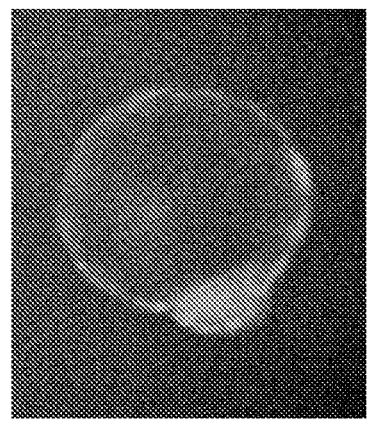
Figure 22:
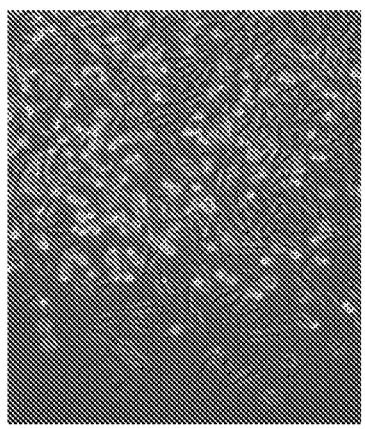
Figure 22:
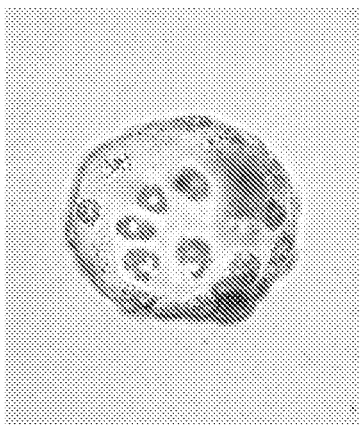

These findings imply that gene shifting can be controlled at a precise place in the genome. The potential of SB and the transposon was investigated in minipig cells. The results showed that primary pig fibroblasts also support SB insertion thus creating a platform for gene shifting in pig cells (see FIG. 21). We prepared minipig cells for SB-mediated gene shifting, and by hand made cloning (HMC) we show that such cells give rise to viable blastocysts expressing the transgene (see FIG. 22).

In conclusion, the Sleeping Beauty DNA transposon-based vector of the present invention serves in its integrated form as a target for recombinase-based gene insertion. The SB vector is efficiently transferred by cut-and-paste transposition into the genome of primary porcine fibroblasts and therefore is not flanked by plasmid-derived bacterial sequences. Use of these genetically engineered primary cells in for example microinjection and hand-made cloning allows subsequent detailed analyses of SB vector-derived eGFP expression in cloned pigs and identification of animals with attractive expression profiles (e.g. ubiquitous, tissue-specific). Primary fibroblasts from such 'master pigs' is further modified by Flp-based recombination, allowing site-directed gene insertion in a SB vector-tagged locus which is not silenced in the tissue of interest. Cloned pigs harboring a site-specifically inserted disease gene of interest or a shRNA expression cassette for downregulation of endogenous genes can be generated by a second round of animal cloning.

Except where otherwise indicated all chemicals for the nuclear transfer procedure were obtained from Sigma Chemical Co. (St Louis, Mo., USA).

Oocyte Collection and In Vitro Maturation (IVM)

Cumulus-oocyte complexes (COCs) were aspirated from 2-6 mm follicles from slaughterhouse-derived sow or gilt ovaries. COCs were matured in groups of 50 in 400 µl bicarbonate-buffered TCM-199 (GIBCO BRL) supplemented with 10% (v/v) cattle serum (CS), 10% (v/v) pig follicular fluid, 10 IU/ml eCG, 5 IU/ml hCG (Suigonan Vet; Skovlunde, Denmark) at 38.5° C. in the "Submarine Incubation System" (SIS; Vajta, et al. 1997) in 5% $CO_2$ in humidified air for 41-44 hours.

In Vitro Fertilization (IVF)

IVF experiments were performed with in vitro matured oocytes in 3 identical replicates. After maturation, COCs were washed twice with mTBM containing 2 mM caffeine ($mTBM_{fert}$) and transferred in groups of 50 to 400 µl mTB-$M_{fert}$. Freshly ejaculated semen was treated as described previously (Booth, et al., in press). After 2 h capacitation at 38.5° C. and in 5% $CO_2$ in humidified air, sperm was added to the oocytes with the adjusted final concentration of $1 \times 10^5$ sperm/ml. Fertilization was performed at 38.5° C. and in 5% $CO_2$ in humidified air in the SIS for 3 h. After the insemination, the presumptive zygotes were vortexed in $mTBM_{fert}$ to remove cumulus cells before washing in IVC medium and placing in culture dishes (see Embryo culture and evaluation).

Handmade Cloning (HMC)

Figure 23:
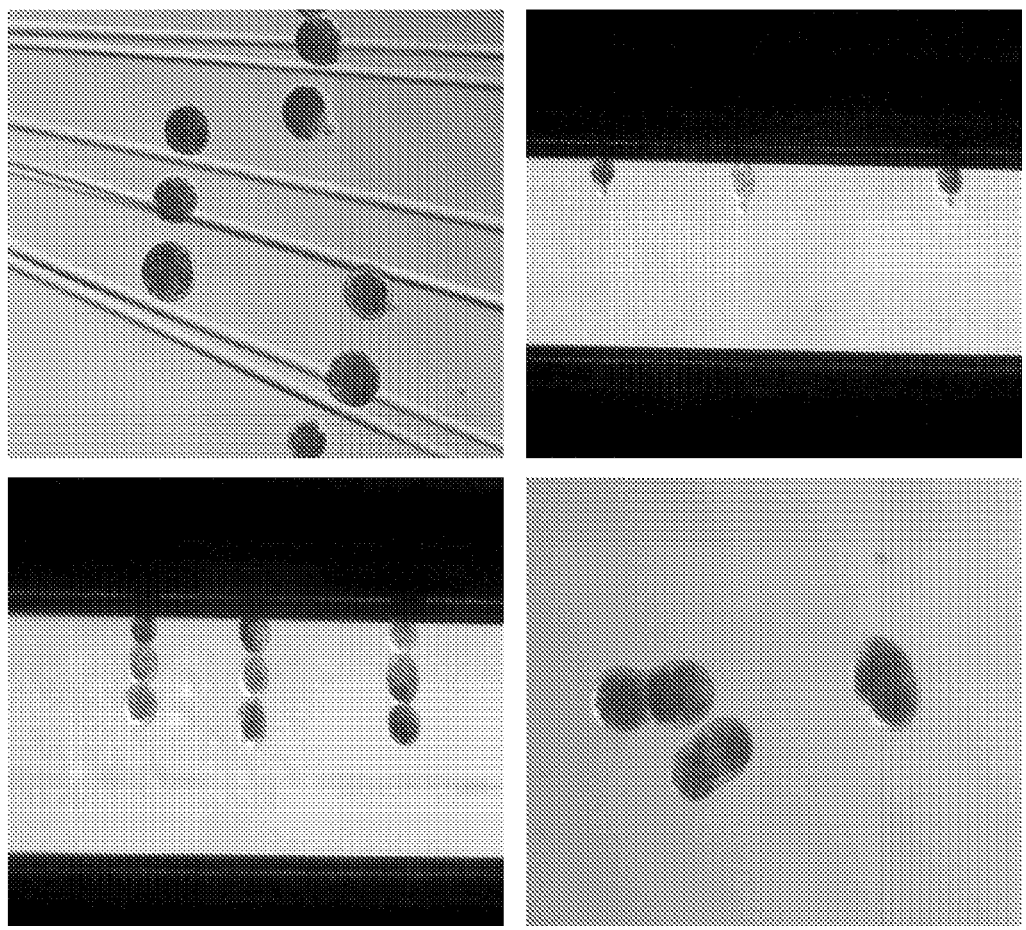
FIG. 23. (a) Oocytes trisection; (b) couplets of fibroblast-oocyte fragment for the first fusion; (c) embryos reconstructed with triplets (note elongation under the AC currency); (d) triplets fusion. Scale bar=50 µm.

The applied HMC method was based on our previous work in cattle and pig (Kragh, et al., 2004; Peura and Vajta, 2003; Vajta, et al., 2003), but with significant modifications. Briefly, at 41 h after the start of maturation, the cumulus investment of the COCs was removed by repeated pipetting in 1 mg/ml hyaluronidase in Hepes-buffered TCM199. From this point (except where otherwise indicated), all manipulations were performed on a heated stage adjusted to 39° C., and all drops used for handling oocytes were of 20 µl volume covered with mineral oil. Oocytes were briefly incubated in 3.3 mg/ml pronase dissolved in T33 (T for Hepes-buffered TCM 199 medium; the number means percentage (v/v) of CS supplement, here 33%) for 5 s. Before the oocytes started to become misshaped in pronase solution, they were picked out and washed quickly in T2 and T20 drops. Oocytes with partially digested but still visible zona were lined up in drops of T2 supplemented with 3 mg/ml polyvinyl alcohol (TPVA) and 2.5 µg/ml cytochalasin B. Trisection instead of bisection was performed manually under stereomicroscopic control with Ultra Sharp Splitting Blades (AB Technology, Pullman, Wash., USA; FIG. 23a). Fragments of trisected oocytes were collected and stained with 5 µg/ml Hoechst 33342 fluorochrome in TPVA drops for 5 min, then placed into 1 µl drops of the TPVA medium on the bottom of a 60 mm Falcon Petri dish covered with oil (3-4 fragments per drop). Using an inverted microscope and UV light, positions of fragments without chromatin staining (cytoplasts) were registered and later collected under a stereomicroscope in T10 drops until the start of the fusion.

Fetal fibroblast cells were prepared as described previously (Kragh, et al., in press). Fusion was performed in two steps where the second one included the initiation of activation, as well. For the first step, one third of the selected cytoplasts (preferably the smaller parts) were used. With a finely drawn and fire-polished glass pipette, 10 cytoplasts were transferred as a group to 1 mg/ml of phytohaemagglutinin (PHA; ICN Pharmaceuticals, Australia) for 3 s, then quickly dropped onto one of the few fibroblast cells individually that were sedimented in a T2 drop. After attachment, 10 cytoplast-fibroblast cell pairs were equilibrated in fusion medium (0.3 M mannitol and 0.01% PVA) for 10 s. Using an alternative current (AC) of 0.6 KV/cm and 700 KHz, cell pairs were aligned to the wire of a fusion chamber (BTX microslide 0.5 mm fusion chamber, model 450; BTX, SanDiego, Calif., USA) with the donor cells farthest from the wire (FIG. 23b), then fused with a direct current (DC) of 2.0 KV/cm for 9 µs. After the electrical pulse, cell pairs were removed carefully from the wire, transferred to T10 drops and incubated to observe whether fusion had occurred.

Approximately 1 hour after the first fusion, fused pairs together with the remaining two thirds of cytoplasts were equilibrated in activation medium drops separately (0.3 M mannitol, 0.1 mM $MgSO_4$, 0.1 mM $CaCl_2$ and 0.01% polyvinylalcohol (PVA)). Under a 0.6 KV/cm AC, cytoplast—fused pair—cytoplast triplets were aligned sequentially to the wire in groups of 10, with fused pairs located in the middle (FIG. 23c). A single DC pulse of 0.7 KV/cm for 80 µs was used for the second fusion and initiation of activation. The triplets were then removed from the wire and transferred carefully to T10 drops to check the fusion (FIG. 23d). Reconstructed embryos were incubated in culture medium (see Embryo culture and evaluation) supplemented with 5 µg/ml cytochalasin B and 10 µg/ml cycloheximide for 4 h at 38.5° C. in 5% $CO_2$, 5% $O_2$ and 90% $N_2$ with maximum humidity, then washed thoroughly for 3 times in IVC medium before culture.

Parthenogenetic Activation (PA)

Parthenogenetically activated oocytes were produced either separately or in parallel with HMC. Oocytes were denuded in the same way as above except that a longer incubation in pronase was used to get the zona pellucida completely removed. Zona free (ZF) oocytes were then equilibrated for 10 s in activation medium (0.3 M mannitol, 0.1 mM $MgSO_4$, 0.1 mM $CaCl_2$ and 0.01% PVA) and transferred to the fusion chamber (BTX microslide 0.5 mm fusion chamber, model 450; BTX, SanDiego, Calif., USA). A single DC pulse of 0.85 KV/cm for 80 µs was generated with a BLS CF-150/B cell fusion machine (BLS, Budapest, Hungary) and applied to ZF oocytes. For zona intact (ZI) oocytes, a single DC pulse of 1.25 KV/cm for 80 µs was used (according to our unpublished preliminary experiments, these parameters resulted in the highest activation and subsequent in vitro development for ZI and ZF oocytes, respectively). The procedure after the electrical pulse was the same as for HMC reconstructed embryos.

Embryo Culture and Evaluation

All porcine embryos produced by the above treatments were cultured in a modified NCSU37 medium (Kikuchi, et al., 2002) containing 4 mg/ml BSA at 38.5° C. in 5% $O_2$, 5% $CO_2$ and 90% $N_2$ with maximum humidity. The culture medium was supplied with 0.17 mm sodium pyruvate and 2.73 mm sodium lactate from Day 0 (the day for fertilization and activation) to Day 2, then sodium lactate and sodium pyruvate was replaced with 5.5 mm glucose from Day 2 to Day 7. All ZF embryos were cultured in the WOW system (Vajta, et al., 2000) in the same culture medium and gas mixture as used above, with careful medium change on Day 2 without removing the embryos from the WOWs. The blastocyst rate was registered on Day 7. To determine total cell numbers, blastocysts were fixed and mounted to a glass microscopic slide in glycerol containing 20 µg/µl Hoechst 33342 fluorochrome. After staining for 24 h, embryos were observed under a Diaphot 200 inverted microscope with epifluorescent attachment and UV-2A filter (Nikon, Tokyo, Japan).

Example 1

Differences in developmental competence between sow (2.5 years, 170 Kg in weight) derived oocytes and gilt (5.5~6 months, 75 Kg in weight) derived oocytes were investigated through ZF and ZI PA after 44 h in vitro maturation. Four combined groups were investigated in 3 identical replicates: (1) ZF oocytes from sows (2) ZI oocytes from sows (3) ZF oocytes from gilts (4) ZI oocytes from gilts. For ZF activation, a single DC pulse of 0.85 KV/cm for 80 µs was applied, while a single 1.25 KV/cm pulse was used to activate ZI oocytes. Following 7 days culture as described above, the percentage of blastocysts per activated embryo was determined.

The in vitro developmental competence of parthenogenetically activated oocytes derived from either sows or gilts was investigated. As shown in Table 1, the blastocyst rates of parthenogenetically activated oocytes from sows were significantly higher than those from gilts, either after ZF or ZI PA.

TABLE 1

Blastocyst development of Day 7 parthenogenetically activated sow and gilt oocytes

|  | Zona Free | | Zona Intact | |
| --- | --- | --- | --- | --- |
|  | No. of activated oocytes | No. of blastocysts (%)* | No. of activated oocytes | No. of blastocysts (%)* |
| sow | 103 | 43(42 ± 4)[a] | 110 | 61(55 ± 6)[c] |
| gilt | 85 | 17(20 ± 2)[b] | 137 | 36(26 ± 5)[d] |

[a,b]Different superscripts mean significant differences ($p < 0.05$).
[c,d]Different superscripts mean significant differences ($p < 0.05$).
*Percentage (Mean ± S.E.M) of embryos developed to blastocysts.

The difference in oocytes developmental competence between sows and gilts has been examined in in vitro production (IVP) and somatic cell nuclear transfer (SCNT) embryos separately, resulting in a similar conclusion as in the earlier publication of other research groups (Sherrer, et al., 2004; Hyun, et al., 2003), i.e. that embryos from sow-derived oocytes are superior to those from gilt-derived oocytes in supporting blastocyst development. Although gilts used in our study were at the borderline of maturity, the difference between Day 7 blastocyst rates after PA was significant, proving the superior developmental competence of sow oocytes.

Example 2

The feasibility of modified porcine HMC was investigated in 6 identical replicates, with IVF and in parallel ZF PA as controls. The more competent sow oocytes (according to Example 1) were used in Example 2. Seven days after reconstruction and/or activation, the number of blastocysts per reconstructed embryo and total cell numbers of randomly selected blastocysts were determined.

More than 90% of oocyte fragments derived from morphologically intact oocytes could be recovered for HMC after the trisection. In average, 37 embryos could be reconstructed out of 100 matured oocytes. The developmental competence of all sources of porcine embryos is shown in Table 2. On Day 7, the development of reconstructed embryos to the blastocyst stage was 17±4% with mean cell number of 46±5, while the blastocyst rates for IVF, and ZF PA were 30±6% and 47±4% (n=243, 170, 97) respectively.

TABLE 2

In vitro development of embryos produced by HMC, IVF and ZF PA

| Embryo origins | No. of embryos/oocytes in culture | No. of blastocysts | blastocyst rates (Mean ± S.E.M). | Mean cell number of blastocysts |
| --- | --- | --- | --- | --- |
| HMC | 243 | 41 | 17 ± 4[a] | 46 ± 5[d] |
| IVF | 170 | 52 | 30 ± 6[b] | 74 ± 6[e] |
| ZF PA | 97 | 46 | 47 ± 4[c] | 53 ± 7[d] |

[a,b,c]Different superscripts mean significant differences ($p < 0.05$).
[d,e]Different superscripts mean significant differences ($p < 0.05$).

Although the theoretical maximum efficiency was still not approached, the integration of zona partial digestion and oocyte trisection almost doubled the number of reconstructed embryos compared to our earlier system (Kragh, et al., 2004 Reprod. Fertil. Dev 16, 315-318). This increase in reconstruction efficiency may have special benefits in porcine cloning since oocyte recovery after aspiration is more demanding and time-consuming than in cattle. An even more important point is the high embryo number required for establishment of pregnancies following porcine nuclear transfer. IVC in pigs is also regarded as a demanding and inefficient procedure (Reed, et al., 1992 Theriogeneology 37, 95-109). A disadvantage of ZF systems is that the embryos have to reach at least the compacted morula or early blastocyst stage in vitro to avoid disintegration in the oviduct without the protective layer of the zona pellucida. On the other hand, once in the blastocyst stage, zona free embryos can be transferred successfully as proved by calves born after either embryonic or somatic cell nuclear transfer (Peura et al., 1998; Tecirlioglu et al., 2004; Oback et al., 2003; Vajta, et al., 2004) and also by the piglets born after zona-free IVP of oocytes (Wu, et al., 2004). NCSU37 medium has been the most widely and successfully used medium for the culture of pig embryos. However, despite the improved embryo development compared with other media, the viability of IVP porcine embryos is still compromised after IVC. Some reports suggested that glucose is not metabolized readily by early porcine embryos before the eight-cell stage but used in higher amounts in embryos between the compacted morula and blastocysts stages (Flood, et al., 1988). The replacement of glucose with pyruvate and lactate in NCSU37 for the first 2 days culture resulted in a blastocyst rate of 25.3% for IVP porcine embryos in Kikuchi's study (Kukuchi, et al., 2002), which was further corroborated by our present studies with an IVP blastocysts rate of 30% in average. Moreover, the first evaluation of this sequential culture system on porcine HMC and ZF PA embryos has resulted in blastocyst rates of 17% and 47% respectively. Sometimes, the blastocyst rate of ZI PA could even reach levels as high as 90% (Du, unpublished)

Statistical Analysis

ANOVA analysis was performed using SPSS 11.0. A probability of $P<0.05$ was considered to be statistically significant.

Example 3

Vitrification of hand-made cloned porcine blastocysts produced from delipated in vitro matured oocytes.

Recently a noninvasive procedure was published for delipation of porcine embryos with centrifugation but without subsequent micromanipulation (Esaki et al. 2004 Biol Reprod. 71, 432-6).

Cryopreservation of embryos/blastocysts was carried out by vitrification using Cryotop (Kitazato Supply Co, Fujinomiya Japan) as described previously (Kuwayama et al. 2005a; 2005b). At the time of vitrification, embryos/blastocysts were transferred into equilibration solution (ES) consisting of 7.5% (V/V) ethylene glycol (EG) and 7.5% dimethylsulfoxide (DMSO) in TCM199 supplemented with 20% synthetic serum substitute (SSS) at 39° C. for 5 to 15 min. After an initial shrinkage, embryos regained their original volume. 4~6 embryos/blastocysts were transferred into 20 ul drop of vitrification solution (VS) consisting of 15% (V/V) EG and 15% (DMSO) and 0.5M sucrose dissolved in TCM199 supplemented with 20% SSS. After incubation for 20 s, embryos were loaded on Cryotop and plunged into liquid nitrogen. The process from exposure in VS to plunging was completed with 1 min.

Embryos/blastocysts were thawed by immersing Cryotop directly into thawing solution (TS) consisting of 1.0M sucrose in TCM199 plus 20% SSS for 1 min, then transferred to dilution solution (DS) consisting of 0.5 M sucrose in TCM199 plus 20% SSS for 3 min. To remove cryoprotectant, embryos/blastocysts were kept twice in a washing solution (WS; TCM199 plus 20% SSS), 5 min for each time. Survival of vitrified blastocysts was determined according to reexpansion rates after 24 h recovery in culture medium supplemented with 10% calf serum (CS).

The non-invasive delipation method was applied to in vitro matured porcine oocytes and further development of delipated oocytes after parthenogenetic activation was investigated in 4 identical replicates. Oocytes were randomly separated into delipation and control groups.

Figure 24:
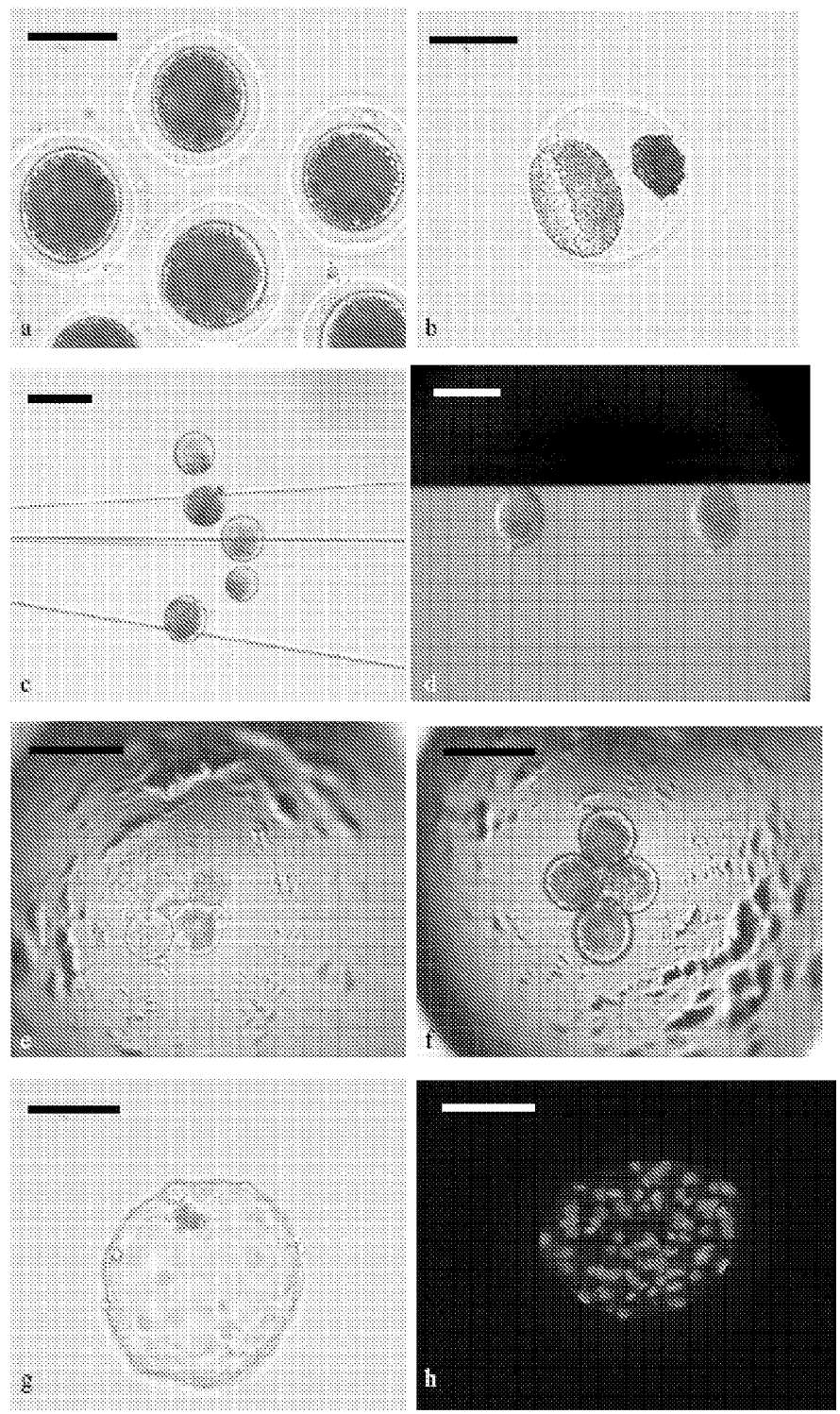
FIG. 24 (a) In vitro matured oocytes after partial zona digestion. (b) Delipated oocytes after centrifugation. (c) Bisection of delipated oocytes. (d) Couplets of fibroblast-oocyte fragment for the first fusion. (e) Four-cell stage reconstructed embryos developed from delipated oocytes. (f) Four-cell stage reconstructed embryos developed from intact oocytes. (g) Re-expanded blastocysts from delipated embryos after warming. (h) Hoechst staining and UV illumination of re-expanded blastocysts from delipated embryos after warming. Bar represents 100 µm.

For delipation, oocytes were digested with 1 mg/ml pronase in the presence of 50% cattle serum (CS) for 3 min, and washed in Hepes-buffered TCM-199 medium supplemented with 20% CS which results in partial zona pellucida digestion (FIG. 24a). Subsequently 40-50 oocytes were centrifuged (12000×g, 20 min) at room temperature in Hepes-buffered TCM-199 medium supplemented with 2% CS, 3 mg/ml PVA and 7.5 µg/ml cytochalasin B (CB) (FIG. 24b). Zonae pellucidea of both centrifuged and intact oocytes were removed completely with further digestion in 2 mg/ml pronase solution. For activation, a single direct current of 85 Kv/cm for 80 us was applied to both groups, followed by 4 h treatment with 5 µg/ml CB and 10 µg/ml cycloheximide (CHX). All embryos were then cultured in the modified NCSU37 medium. Day 7 blastocysts were vitrified and warmed by using the Cryotop technique (Kuwayama et al., RBM Online, in press) at 38.5° C. Survival of vitrified blastocysts was determined according to reexpansion rates after 24 h recovery in culture medium supplemented with 10% CS. Cell numbers of reexpanded blastocysts from both groups were determined after Hoechst staining. Results were compared by ANOVA analysis. Partial zona digestion and centrifugation resulted in successful delipation in 173/192 (90%) of oocytes. The development to blastocysts was not different between delipated and intact oocytes (28±7% vs. 28±5% respectively; P>0.05). However, survival rates of blastocysts derived from delipated oocytes were significantly higher than those developed from intact oocytes (85±6% vs. 32±7% respectively; P<0.01). There is no difference in average cell number of reexpanded blastocysts derived from either delipated or intact oocytes (36±7 vs. 38±9, respectively; P>0.05). The results demonstrate that the simple delipation technique does not hamper the in vitro development competence of activated porcine oocytes, and improves the cryosurvival of the derived blastocysts without significant loss in cell number.

After delipation, zona pellucida of oocytes from both groups was removed completely. The same parameters as described above for electrical activation were applied to both groups. Seven days after activation, blastocyst rates and blastocyst cell numbers were determined.

The feasibility of applying a non-invasive delipation technique to in vitro matured porcine oocytes was investigated. 90% (173/192) oocytes can be delipated successfully. As shown in table 3, the development to blastocysts was not different between delipated and intact oocytes (28±7% vs. 28±5% respectively; P>0.05). However, survival rates of blastocysts derived from delipated oocytes were significantly higher than those developed from intact oocytes (85±6% vs. 32±7% respectively; P<0.01). There is no difference in average cell number of reexpanded blastocysts derived from either delipated or intact oocytes (36±7 vs. 38±9, respectively; P>0.05).

TABLE 3

Developmental competence and cryosurvival of vitrified-thawed embryos from delipated and intact activated oocytes.

| Oocyte treatment | Activated oocyte | Blastocyst rate (%) | Reexpanded blastocyst after warming (%) | Mean cell number of reexpanded blastocysts |
|---|---|---|---|---|
| Delipated | 173 | 28 ± 7 | 85 ± 6 | 36 ± 7 |
| Intact | 156 | 28 ± 5 | 32 ± 7 | 39 ± 9 |

Handmade Cloning of Delipated Oocytes

Delipated oocytes were used for HMC in 5 replicates. Four identical replicates of non-delipated oocytes for HMC were used as a control system. Seven days after reconstruction, blastocysts produced from both groups were vitrified with Cryotop. Survival rates and cell numbers of re-expanded blastocysts were determined as described for the blastocysts produced by PA.

Except where otherwise indicated, all manipulations were performed on a heated stage adjusted to 39° C., and all drops used for handling oocytes were of 20 µl volume covered with mineral oil. For somatic cell nuclear transfer, the handmade cloning (HMC) described in our previous work (Du, et al., 2005) was applied with a single modification: for enucleation of both delipated and control oocytes, bisection instead of trisection was applied.

Briefly, after the removal of cumulus investment, control oocytes were incubated in 3.3 mg/ml pronase dissolved in T33 for 10 s. Before the oocytes started to become misshaped in pronase solution, they were picked out and washed quickly in T2 and T20 drops. Delipated oocytes after centrifugation were digested in the 3.3 mg/ml pronase solution for an additional 5 s.

Both control and delipated oocytes with partially digested, distended and softened zonae pellucidae were lined up in T2 drops supplemented with 2.5 µg/ml cytochalasin B. Bisection was performed manually under stereomicroscopic control (FIG. 24c) with Ultra Sharp Splitting Blades (AB Technology, Pullman, Wash., USA). Halves were collected and stained with 5 µg/ml Hoechst 33342 fluorochrome in T2 drops for 5 min, and then placed into 1 µl drops of T2 medium on the bottom of a 60 mm Falcon Petri dish covered with oil (3-4 halves per drop). Using an inverted microscope and UV light, positions of halves without chromatin staining (cytoplasts) were registered. Cytoplasts were later collected under a stereomicroscope and stored in T10 drops.

Porcine foetal fibroblast cells were prepared with trypsin digestion from monolayers as described previously (Kragh, et al., 2005). Fusion was performed in two steps where the second one included the initiation of activation, as well. For the first step, 50% of the available cytoplasts were transferred into 1 mg/ml of phytohaemagglutinin (PHA; ICN Pharmaceuticals, Australia) dissolved in TO for 3 s, then quickly dropped over single fibroblast cells. After attachment, cytoplast-fibroblast cell pairs were equilibrated in fusion medium (0.3 M mannitol and 0.01% PVA) for 10 s and transferred to the fusion chamber. Using an alternating current (AC) of 0.6 KV/cm and 700 KHz, pairs were aligned to the wire of a fusion chamber with the somatic cells farthest from the wire (FIG. 24d), then fused with a direct current of 2.0 KV/cm for 9 µs. After the electrical pulse, cell pairs were removed carefully from the wire, transferred to T10 drops and incubated to observe whether fusion had occurred.

Approximately 1 hour after the first fusion, each pair was fused with another cytoplast in activation medium. AC current and a single DC pulse of 0.7 KV/cm for 80 μs were applied as described above. Fusion was detected in T10 drops, then reconstructed embryos were transferred into IVC0-2 medium (see Embryo culture and evaluation) supplemented with 5 μg/ml cytochalasin B and 10 μg/ml cycloheximide. After a 4 h incubation at 38.5° C. in 5% $CO_2$, 5% $O_2$ and 90% $N_2$ with maximum humidity, embryos were washed 3 times in IVC0-2 medium before culture.

TABLE 4

Developmental competence and cryosurvival of vitrified-thawed embryos of SCNT porcine embryos derived from delipated and intact oocytes.

| HMC group | No. of reconstructed embryos | Blastocyst rate (%)* | Reexpanded blastocyst after warming (%)* | Mean cell number of reexpanded blastocysts* |
|---|---|---|---|---|
| Delipated | 240 | 21 ± 6[a] | 79 ± 6[b] | 41 ± 7[d] |
| Intact | 150 | 23 ± 6[a] | 32 ± 8[c] | 39 ± 5[d] |

Different superscripts mean significant differences (p < 0.05).
*mean ± S.E.M.

In vitro developmental competence was observed in HMC with delipated oocytes when Day 7 blastocyst rates were compared with control HMC group (21±6% vs. 23±6% respectively; P>0.05; Table 4). Cryosurvival rate after vitrification of cloned blastocysts derived from delipated oocytes was significantly higher than those developed from intact oocytes (79±6% vs. 32±8, respectively; P<0.01).

Example 4

Chemically Assisted Handmade Enucleation (CAHE) and Comparison to Existing Methods After 41-42 h maturation in vitro, COCs were further cultured for 45 min in the same solution supplemented by 0.4 μg/ml demecolcine. Cumulus cells were then removed by pipetting in 1 mg/ml hyaluronidase dissolved in Hepes-buffered TCM-199. From this point (except where otherwise indicated), all manipulations were performed on a heated stage adjusted to 39° C. All drops used for handling oocytes were of 20 μl in volume, and were covered with mineral oil.

Figure 25:
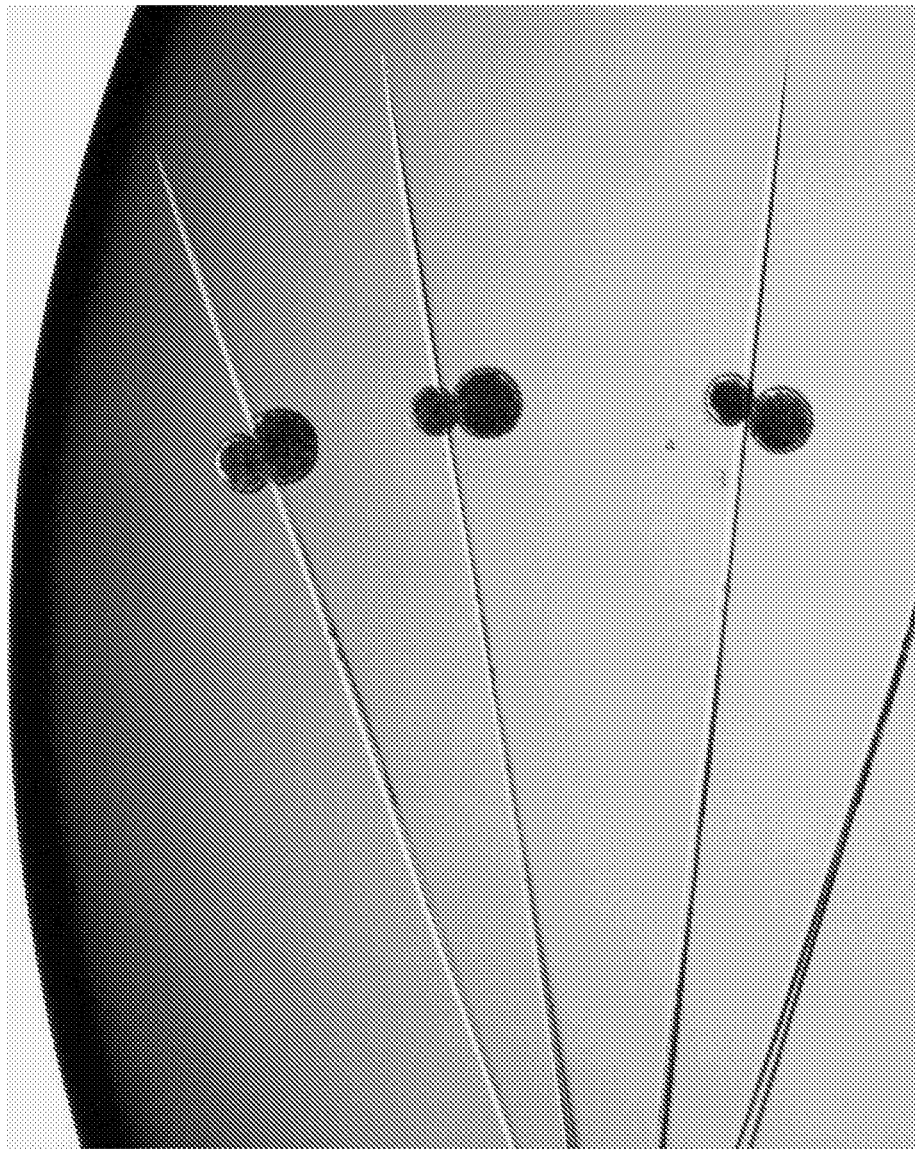
FIG. 25. Bisection at chemically assisted enucleation. Note the extrusion cone or polar body connected to the smaller part (putative karyoplast). Stereomicroscopic picture. Bar represents 50 µm.

Basic steps of the HMC procedure have been described elsewhere herein. Briefly, oocytes without cumulus cells were incubated in 3.3 mg/ml pronase dissolved in T33 (T for Hepes-buffered TCM 199 medium; the number means percentage [v/v] of CS supplement, here 33%) for 20 s. When partial lyses of zonae pellucidae and slight deformation of oocytes occurred, they were picked up and washed quickly in T2 and T20 drops. Nine oocytes were lined up in one T2 drop supplemented with 2.5 μg/ml cytochalasin B (CB). By using a finely drawn and fire-polished glass pipette, oocytes were rotated to find a light extrusion cone and/or strongly attached polar body on the surface, and oriented bisection was performed manually under stereomicroscopic control with a microblade (AB Technology, Pullman, Wash., USA). Less than half of the cytoplasm (close to the extrusion or PB) was separated from the remaining part (FIG. 25). After bisection of all 9 oocytes in the drop, larger parts and smaller parts (with the extrusion or attached PB) were collected and placed into separate drops of T2, respectively.

Oriented Handmade Enucleation without Demecolcine Treatment (OHE)

All steps were similar to the previously described procedure, but demecolcine preincubation was not applied.

Random Handmade Bisection for Enucleation (RHE)

Demecolcine preincubation was omitted from the pretreatment of this group, as well. After removal of cumulus cells, zonae pellucidae were partially digested by pronase as described above. Random handmade equal bisection was applied in drops of T2 supplemented with 2.5 μg/ml CB. All demi-oocytes were selected and stained with 10 μg/ml Hoechst 33342 in T2 drops for 10 min, then placed into 1 μl drops of T2 medium covered with mineral oil (three demi-oocytes into each drop). Using an inverted microscope and UV light, the positions of chromatin free demi-oocytes, i.e. cytoplasts were registered. These cytoplasts were later collected under a stereomicroscope and stored in T2 drops before further manipulations.

Fusion and Initiation of Activation

Porcine fetal fibroblast cells were prepared as described previously (Kragh, et al., 2005, Du, et al., 2005). Fusion was performed in two steps, where the second one included the initiation of activation as well. For the first step, with a finely drawn and fire-polished glass pipette, approximately 100 somatic cells were placed into a T2 drop, and 20-30 cytoplasts were placed into a T10 drop. After a short equilibration, groups of 3 cytoplasts were transferred to 1 mg/ml of phyto-haemagglutinin (PHA) for 2-3 sec, then each was quickly dropped over a single somatic cell. Following attachment, cytoplast-somatic cell pairs were picked up again and transferred to a fusion medium (0.3 M mannitol supplemented with 0.01% [w/v] PVA). By using an alternative current (AC) of 0.6 KV/cm and 700 KHz, equilibrated pairs were aligned to one wire of a fusion chamber (BTX microslide 0.5 mm fusion chamber, model 450; BTX, San Diego, Calif.) with the somatic cells farthest from the wire, then fused with a single direct current (DC) impulse of 2.0 KV/cm for 9 μsec. Pairs were then removed carefully from the wire to a T10 drop, and incubated further to observe whether fusion had occurred.

Approximately 1 h after the fusion, fused pairs and the remaining cytoplasts were separately equilibrated in activation medium (0.3 M mannitol, 0.1 mM $MgSO_4$, 0.1 mM $CaCl_2$, supplemented with 0.01% [w/v] PVA). By using a 0.6 KV/cm AC, one pair and one cytoplast was aligned to one wire of the fusion chamber, with fused pairs contacting the wire. A single DC pulse of 0.86 KV/cm for 80 μsec was used for the second fusion and initiation of activation. Fusion was checked in after incubation in T10 drops.

Traditional Cloning (TC)

Micromanipulation was conducted with a Diaphot 200 inverted microscope (Nikon, Tokyo, Japan), as described before (Chen et al., 1999; Zhang et al., 2005). Briefly, after 42-44 h in vitro maturation, the cumulus cells were removed as described above. All manipulations were performed on a heated stage adjusted to 39° C. A single 50 μL micromanipulation solution drop was made in the central area on a lid of 60 mm culture dish and covered with mineral oil. Groups of 20-30 oocytes and fetal fibroblast cells were placed in the same drop. After incubation for 15-30 min, the oocyte was secured with a holding pipette (inner diameter=25-35 μm and outer diameter=80-100 μm). After being placed at the position of 5-6 o' clock, the first polar body and the adjacent cytoplasm (approx. 10% of the total volume of the oocyte) presumptively containing metaphase plate were aspirated and removed with a beveled injection pipette (inner diameter=20 μm). A fetal fibroblast cell was then injected into the space through the same slit. After nuclear transfer (NT), reconstructed couplets were transferred into drops of media covered with mineral oil for recovery for 1-1.5 h until fusion and activation was conducted. The recovery medium was NCSU-23 supplemented with 4 mg/mL BSA and 7.5 µg/mL CB. Reconstructed couplets were incubated in fusion medium for 4 min. Couplets were aligned manually using a finely pulled and polished glass capillary to make the contact plane parallel to electrodes. A single, 30 µsec, direct current pulse of 2.0 kV/cm was then applied. After culture in drops of IVC0-2 (specified in "Embryo culture and evaluation") supplemented with 7.5 µg/mL CB for 30-60 min, fusion results were examined under a stereomicroscope. Fused couplets were subjected to a second pulse in activation solution. After 30 min incubation in T10 they were transferred to IVC0-2 to evaluate in vitro development.

Further Steps of Activation

After the activation impulse, all reconstructed embryos were incubated in IVC0-2 supplemented with 5 µg/ml CB and 10 µg/ml cycloheximide at 38.5° C. in 5% $CO_2$, 5% $O_2$, and 90% $N_2$, with maximum humidity.

Embryo Culture and Evaluation 4 h later, all reconstructed and activated embryos were washed and cultured in Nunc four-well dishes in 400 µl IVC0-2 covered by mineral oil at 38.5° C. in 5% $CO_2$, 5% $O_2$, and 90% $N_2$, with maximum humidity. IVC0-2 was a modified NCSU37 medium (Kikuchi, et al., 1999), containing 4 mg/ml BSA, 0.17 mM sodium pyruvate, and 2.73 mM sodium lactate from Day 0 (the day for activation) to Day 2. Sodium pyruvate and sodium lactate were replaced with 5.5 mM glucose from Day 2 to Day 7 (IVC2-7). All zonae free embryos were cultured in the Well of the Well (WOW) system (Vajta et al., 2000) in the same culture medium and gas mixture as used above, with careful medium change on Day 2 without removing the embryos from the WOWs. TC embryos were cultured in groups of 15 to 30 in wells of four-well dishes by using the same medium amount and composition. Cleavage and blastocyst rates were registered on Day 2 and Day 7, respectively. To determine total cell numbers, blastocysts were fixed and mounted to a glass microscope slide in a small amount (<2 µl) of glycerol containing 10 µg/ml Hoechst 33342. After staining for several hours at room temperature, embryos were observed under a Diaphot 200 inverted microscope with epifluorescent attachment and UV-2A filter (Nikon, Tokyo, Japan).

Comparison of Efficiency of CAHE Vs. OHE

Figure 26:
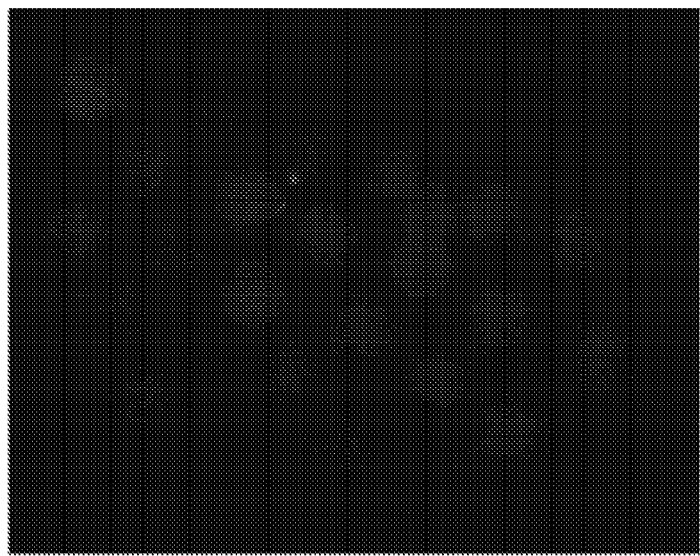
FIG. 26. Hoechst staining and UV illumination of the absence and presence of chromatin. UV light, inverted fluorescent microscopic picture. Bar represents 50 µm. (a) The absence of chromatin in putative cytoplasts (b) The presence of chromatin in putative karyoplasts.
Figure 26:
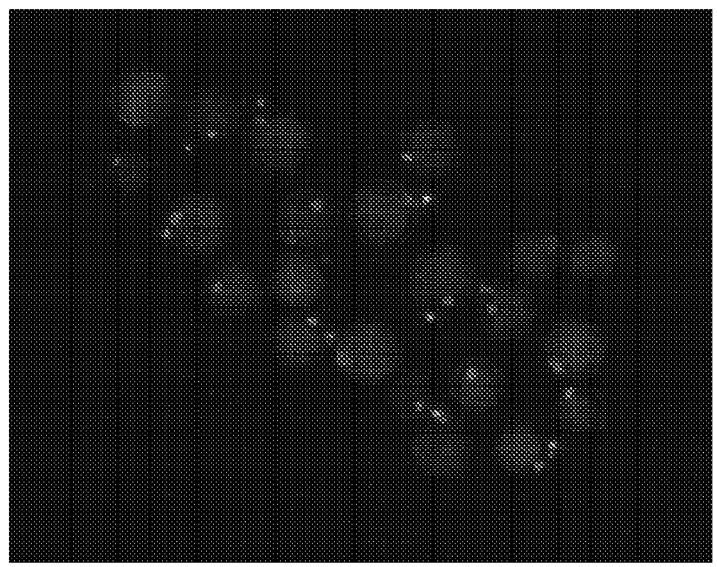

The efficiency and reliability of CAHE was tested in 12 identical replicates by using a total of 620 oocytes. After 41-42 h maturation, oocytes were subjected to demecolcine incubation. Oriented bisection was performed in oocytes where an extrusion cone and/or a strongly attached PB was detected after partial pronase digestion. Percentages of bisected vs. total oocytes and surviving vs. bisected oocytes were registered. Subsequently both putative cytoplasts and karyoplasts were collected separately and stained with Hoechst 33342 (10 µg/ml in T2 for 10 min). The presence or absence of chromatin was detected under an inverted fluorescent microscope (FIG. 26).

The efficiency and reliability of OHE was investigated in 9 identical replicates using a total of 414 oocytes. After 42-43 h in vitro maturation, oriented bisection was performed in matured oocytes where an extrusion cone and/or a PB was detected after partial pronase digestion. Results were evaluated as described in the previous paragraph.

The results are shown in Table 5.

TABLE 5

The efficiency of chemically assisted handmade enucleation (CAHE) and oriented handmade enucleation (OHE)

| Groups | No. of treated oocytes | Bisected/ total oocytes (%)* | Cytoplast/ bisection (%)* | Cytoplast/ total oocyte (%)* |
|---|---|---|---|---|
| CAHE | 620 | 96 ± 1$^a$ | 94 ± 2$^b$ | 90 ± 3$^c$ |
| OHE | 414 | 92 ± 2$^a$ | 88 ± 3$^b$ | 81 ± 4$^d$ |

*mean ± A.D. (absolute deviations)
Different superscripts mean difference (P < 0.05)

No differences between groups regarding extrusion cones and/or attached polar bodies allowing oriented bisection or in the lysis rates were detected, and the successful enucleation per bisected oocyte ratio was also similar. However the overall efficiency of the procedure measured by the cytoplast per total oocyte number was higher in the CAHE than in the OHE group.

Comparison of in vitro development of embryos produced with CAHE, RHE and TC

In 8 replicates, a total of 468 in vitro matured oocytes were randomly distributed and subjected to three of the enucleation procedures described above. Fusion rates between cytoplast and donor fibroblasts were registered. Reconstructed embryos were activated and cultured as described earlier. Cleavage and blastocyst rates were determined on Day 2 and Day 7, respectively. Stereomicroscopic characteristics of the developed blastocysts were compared between groups.

TABLE 6

Developmental competence of embryos derived from chemically assisted handmade enucleation (CAHE), random handmade enucleation (RHE) and traditional, micromanipulator based cloning (TC).

| Groups | No. of reconstructed embryos | Fusion rate (%)* | Cleavage rate (%)* | Blastocyst rate (%)* | Cell no. of blastocysts (Day 7) |
|---|---|---|---|---|---|
| CAHE | 150 | 87 ± 7$^a$ | 97 ± 6$^b$ | 28 ± 9$^d$ | 57 ± 6$^e$ |
| RHE | 86 | 81 ± 4$^a$ | 87 ± 8$^b$ | 21 ± 9$^d$ | 49 ± 7$^e$ |
| TC | 178 | 81 ± 10$^a$ | 69 ± 9$^c$ | 21 ± 6$^d$ | 53 ± 6$^e$ |

*mean ± A.D. (absolute deviations)
Different superscripts mean difference (P < 0.05).

Fusion rates after enucleation were similar between CAHE, RHE and TC, respectively. The second fusion and activation resulted in negligible (<1%) losses in the first two groups. Although TC resulted in lower cleavage per reconstructed embryo rates than the other two groups, this difference was not present in the blastocyst per reconstructed embryo rates.

Figure 27:
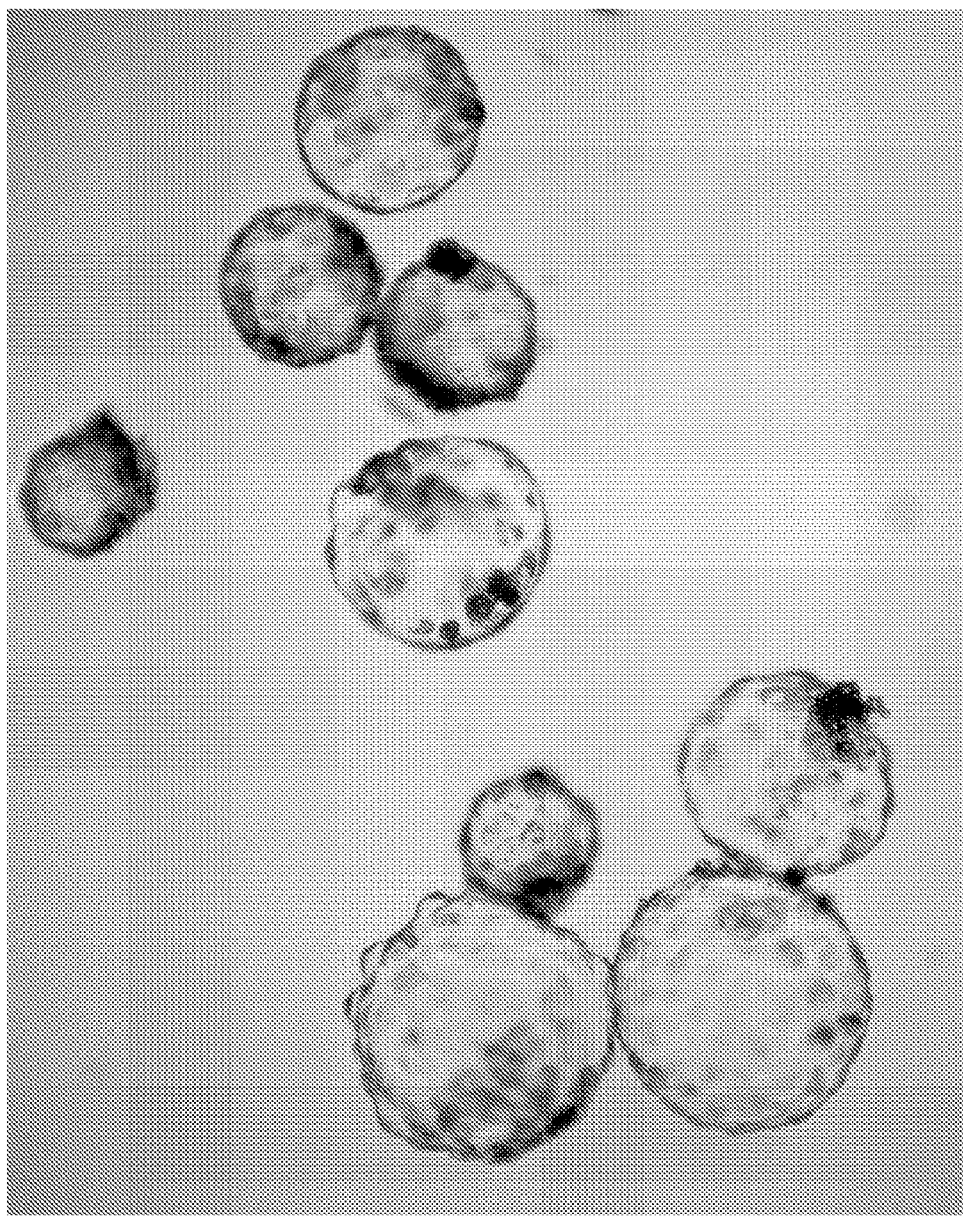
FIG. 27. Stereomicroscopic picture of Day 7 blastocysts produced with chemically assisted handmade enucleation (CAHE). Bar represents 50 µm.
Figure 28:
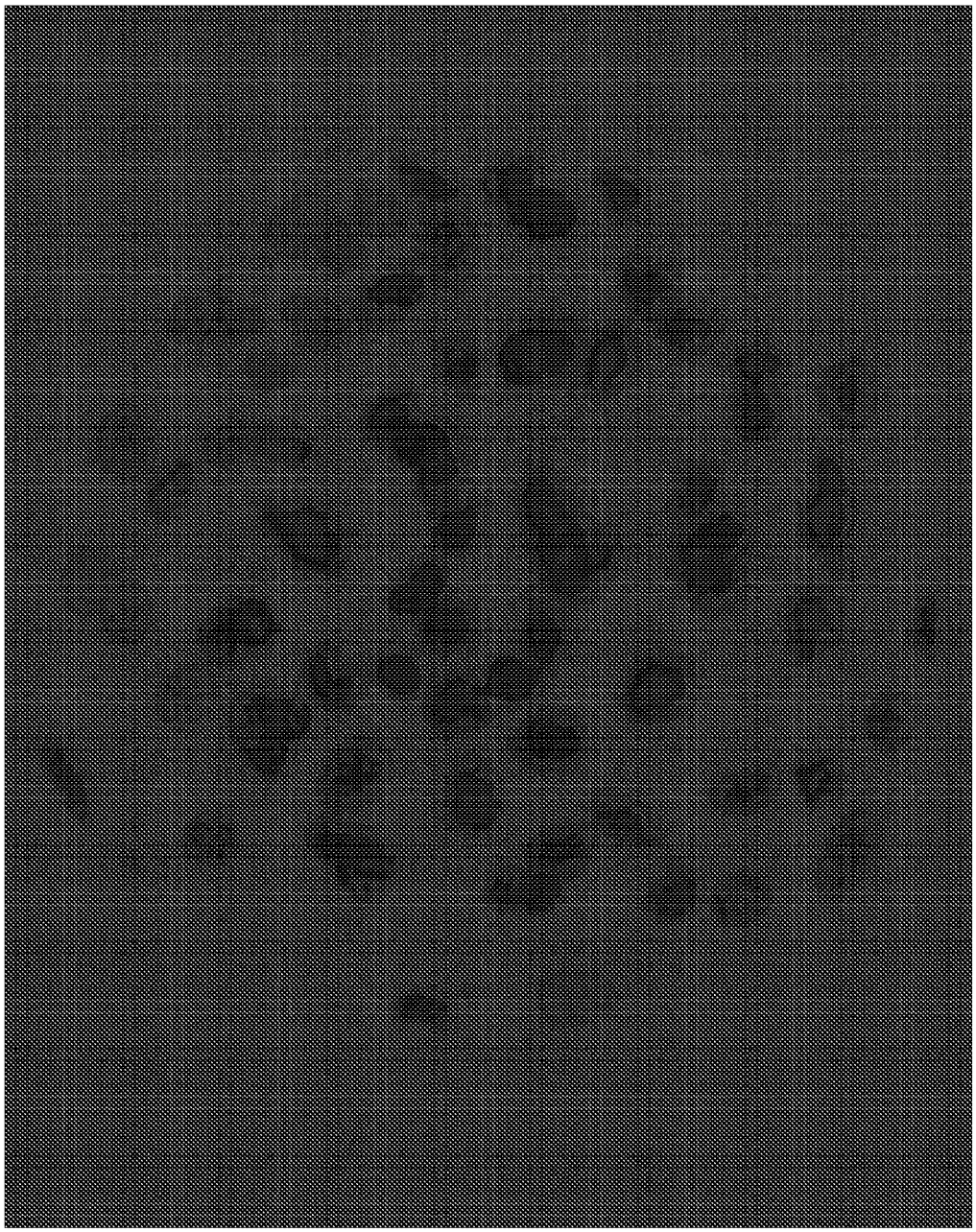
FIG. 28. Hoechst staining and UV illumination of blastocyst developed after chemically assisted handmade enucleation (CAHE). Bar represents 50 µm.

Stereomicroscopic characteristics (size; estimated proportion and outlines of the inner cell mass) did not differ between groups. Cell numbers (57±6 vs. 49±7 vs. 53±6) of the produced blastocysts from CAHE, RHE and TC are shown in Table 6, FIG. 27 and FIG. 28.

Statistical Analysis

AVEDEV was performed by Microsoft XP Excel software and ANOVA was performed by SAS system. A probability of $P<0.05$ was considered to be statistically significant.

Example 5

Production of Piglets
Handmade Cloning (HMC)

Forty one hrs after the start of in vitro maturation, the cumulus investment of the COCs was removed by repeated pipetting in 1 mg/ml hyaluronidase in Hepes-buffered TCM199. From this point (except where otherwise indicated) all manipulations were performed on a heated stage adjusted to 39° C., and all drops used for handling oocytes were of 20 µl volume covered with mineral oil. Oocytes were briefly incubated in 3.3 mg/ml pronase dissolved in T33 (T for Hepes-buffered TCM 199 medium; the number means percentage (v/v) of calf serum (CS) supplement, here 33%) for 20 sec and then quickly washed in T2 and T20 drops. Oocytes with partially digested but still visible zona were lined up in drops of T2 supplemented with 2.5 µg/ml cytochalasin B (CB). With a finely drawn and fire-polished glass pipette, oocytes were rotated to find the polar body (PB) on the surface, and oriented bisection was performed manually under stereomicroscopic control with a microblade (AB Technology, Pullman, Wash., USA). Thus, less than half of the oocyte cytoplasm (close to the extrusion or PB) was removed from the remaining putative cytoplast. Cytoplasts were washed twice in T2 drops and collected in a T10 drop.

Fetal fibroblast cells were prepared as described previously (Kragh, P. M. et al. *Theriogenology* 64, 1536-1545 (2005).

Fusion was performed in two steps where the second one included the initiation of activation, as well. For the first step, halves of putative cytoplasts were used. With a finely drawn and fire-polished glass pipette, 10 cytoplasts were transferred as a group to 1 mg/ml of phytohaemagglutinin (PHA; ICN Pharmaceuticals, Australia) for 3 sec, then quickly dropped individually onto one of the few fibroblast cells that were sedimented in a T2 drop. After attachment, 10 cytoplast-fibroblast cell pairs were equilibrated in fusion medium (0.3 M mannitol and 0.01% PVA) for 10 sec. Using an alternative current (AC) of 0.6 KV/cm and 700 KHz, cell pairs were aligned to the wire of a fusion chamber (BTX microslide 0.5 mm fusion chamber, model 450; BTX, San Diego, Calif., USA) with the somatic cells farthest from the wire, then fused with a direct current (DC) of 2.0 KV/cm for 9 µsec. After the electrical pulse, cell pairs were removed carefully from the wire, transferred to T10 drops and incubated to observe whether fusion had occurred.

Approximately 1 hr after the first fusion, fused pairs together with the remaining cytoplasts were equilibrated in activation medium drops separately (0.3 M mannitol, 0.1 mM $MgSO_4$, 0.1 mM $CaCl_2$ and 0.01% PVA). Under a 0.6 KV/cm AC, cytoplast—fused pair were aligned sequentially to the wire in groups of 10, with fused pairs far from the wire. A single DC pulse of 0.7 KV/cm for 80 µsec was used for the second fusion and initiation of activation. The pairs were then removed from the wire and transferred carefully to T10 drops to check the fusion. Reconstructed embryos were incubated in PZM-3 medium supplemented with 5 µg/ml CB and 10 µg/ml cycloheximide for 4 hr at 38.5° C. in 5% $CO_2$, 5% $O_2$ and 90% $N_2$ with maximum humidity, then washed thoroughly before culture.

Traditional Cloning (TC)

Micromanipulation was conducted with a Diaphot 200 inverted microscope (Nikon, Tokyo, Japan). Cumulus cells were removed as described above after 42 to 44 hr maturation. All manipulations were performed on a heated stage adjusted to 39. A single 50 µL drop of micromanipulation solution (NCSU-23 supplemented with 4 mg/mL BSA and 7.5 µg/mL CB) was made in the central area on a lid of 60 mm culture dish and covered with mineral oil. Groups of 20 to 30 oocytes and fetal fibroblast cells were placed in the same drop. After incubation for 15 to 30 min, one oocyte was secured with a holding pipette (inner diameter=25-35 µm and outer diameter=80-100 µm). After being placed at the position of 5-6 o'clock, the first polar body and the adjacent cytoplasm (approx. 10% of the total volume of the oocyte) presumptively containing metaphase plate were aspirated and removed with a beveled injection pipette (inner diameter=20 µm). A fetal fibroblast cell was then injected into the space through the same slot. After nuclear transfer (NT), reconstructed couplets were transferred into drops of media covered with mineral oil for recovery for 1 to 1.5 hrs until fusion and activation was conducted. Reconstructed couplets were incubated in fusion medium for 4 min. Couplets were aligned manually using a finely pulled and polished glass capillary to make the contact plane parallel to electrodes. A single, 30 µsec, direct current pulse of 2.0 kV/cm was then applied. After culture in drops of PZM-3 medium supplemented with 7.5 µg/mL CB for 30-60 min, fusion results were examined under a stereomicroscope. Fused couplets were subjected to a second pulse in activation solution. After 30 min incubation in T10 they were transferred to PZM-3 medium to evaluate in vitro development.

Embryo Culture and Transfer

Reconstructed embryos were cultured in PZM-3 medium (Dobrinsky, J. T. et al. *Biol Reprod* 55, 1069-1074 (1996) supplemented with 4 mg/ml BSA. Zona-free embryos produced from HMC were cultured in the modified WOWs system (Feltrin, C. Et al. *Reprod Fertil Dev* 18, 126 (2006). Two different cell lines (LW1-2 for HMC, LW2 for TC) were used as nuclear donor cells for HMC and TC to allow the identification of the offspring from the two procedures. LW1-2 and LW2 originate from fetuses from a cross (with Duroc) and pure Danish landrace, respectively.

The average blastocyst per reconstructed embryo rate after in vitro culture for 7 days was 50.1±2.8% (mean±S.E.M), which is significantly higher (p<0.01) for HMC than that of TC performed in parallel in our laboratory (Table 7) and also the highest one that has ever been reported in pig cloning.

TABLE 7

In vitro development of embryos produced from handmade cloning and traditional cloning

| Group | Somatic cell donor | No. of reconstructed embryos | Cleavage rate (%) | Blastocyst rate (%) |
|---|---|---|---|---|
| HMC | LW1-2 | 643 | 83.7 ± 4.90[a] | 50.06 ± 2.80[a] |
| TC | LW2 | 831 | 74.86 ± 13.16[b] | 28.98 ± 2.84[b] |

[a,b]Values of different superscripts within columns are significantly different (p < 0.05).
*mean ± S.E.M.

Mixed blastocysts produced from both HMC and TC were surgically transferred to 11 naturally synchronized sows on Day 4 or 5 of estrous cycle. Six (55%) recipients were diagnosed pregnant by ultrasonography, 2 aborted and by the time of writing 2 have delivered 3 and 10 piglets, respectively. A litter size of 10 cloned piglets is, according to our knowledge, the largest litter size so far achieved in pig cloning. All of them are healthy and behave normally except one showed rigid flexure of distal joint of one foreleg. %).

Preliminary results suggest that when embryos of similar stages were transferred, recipients on Day 4 of the estrous cycle supported pregnancy establishment better than those of Day 5 (Table 8).

TABLE 8

| | In vivo development of cloned porcine embryos | | | | | | | |
|---|---|---|---|---|---|---|---|---|
| | Embryos transferred | | Embryo | Recipient | | No. of piglets born | | |
| Recipient number | HMC embryo | TC embryo | stage (Day) | cycle (Day) | Pregnancy status | piglets from HMC | No. piglets from TC | Gestation length (Day) |
| 1327 | 22 | 10 | D 5, 6, 7 | 4 | Y | 2 | 1 | 116 |
| 1539 | 36 | 10 | D 7 | 4 | Y | 8 | 2 | 115 |
| 1309 | 30 | 28 | D 5, 6 | 4 | Y | | | |
| 1553 | 45 | 44 | D 5, 6 | 4 | Y | | | |
| 1668 | 48 | 18 | D 5, 6 | 5 | Y, aborted | | | |
| 1428 | 78 | 22 | D 5, 6 | 5 | Y, aborted | | | |
| 1725 | 44 | 4 | D 5, 6, 7 | 5 | N | — | — | — |
| 1643 | 22 | 11 | D 5, 6, 7 | 4 | N | — | — | — |
| 1520 | 30 | 26 | D 5, 6 | 4 | N | — | — | — |
| 1363 | 37 | 7 | D 6, 7 | 5 | N | — | — | — |
| 1560 | 99 | 42 | D 5, 6, 7 | 5 | N | — | — | — |

Microsatellite Analysis

Parental analysis using 10 different porcine microsatellite markers confirmed the identical genotype of cloned piglets and donor cells used for nuclear transfer. Identification was done by microsatellite analysis of genomic DNA from each of the newborn piglets, the surrogate sow, and the donor skin fibroblasts LW1-2 and LW2 originating from two fetuses that represent Danish landrace and Duroc, respectively. Ten polymorphic microsatellite loci (SW886, SW58, SW2116, SW1989, SW152, SW378, KS139, SO167, SW1987, SW957) located on different porcine chromosomes were amplified by 3-color multiplex PCR and the products analyzed on the Genetic Analyzer 3130×1 (Applied Biosystems) using the program Gene Mapper 3.7.

For the second recipient, the offspring per embryo rate (22%) was the highest one ever reported so far in pig cloning (Walker, S. C. et al. *Cloning Stem Cells* 7, 105-112 (2005); Hoshino, Y. et al. *Cloning Stem Cells* 7, 17-26 (2005)). Comparable live birth/transferred embryo efficiencies were obtained in HMC (17%) and TC (15%).

Statistical Analysis

Differences between the experimental groups were evaluated using independent-samples t-test by SPSS 11.5. $P<0.05$ was considered significant.

References

1. S. O'Gorman, D. T. Fox, G. M. Wahl, *Science* 251, 1351 (Mar. 15, 1991).
2. J. R. Broach, J. B. Hicks, *Cell* 21, 501 (September, 1980).
3. B. Thyagarajan, E. C. Olivares, R. P. Hollis, D. S. Ginsburg, M. P. Calos, *Mol Cell Biol* 21, 3926 (June, 2001).
4. A. M. Geurts et al., *Nucleic Acids Res* 34, 2803 (2006).
5. Z. Ivics, P. B. Hackett, R. H. Plasterk, Z. Izsvak, *Cell* 91, 501 (Nov. 14, 1997).
6. J. G. Mikkelsen et al., *Mol Ther* 8, 654 (October, 2003).
7. T. J. Vigdal, C. D. Kaufman, Z. Izsvak, D. F. Voytas, Z. Ivics, *J Mol Biol* 323, 441 (Oct. 25, 2002).
8. S. R. Yant et al., *Nat Genet.* 25, 35 (May, 2000).
9. C. S. Branda, S. M. Dymecki, *Dev Cell* 6, 7 (January, 2004).
10. A. L. Garcia-Otin, F. Guillou, *Front Biosci* 11, 1108 (2006).
11. F. Buchholz, P. O. Angrand, A. F. Stewart, *Nat Biotechnol* 16, 657 (July, 1998).
12. J. H. Chung, M. Whiteley, G. Felsenfeld, *Cell* 74, 505 (Aug. 13, 1993).
13. T. M. Yusufzai, G. Felsenfeld, *Proc Natl Acad Sci USA* 101, 8620 (Jun. 8, 2004).
14. R. J. Yanez-Munoz et al., *Nat Med* 12, 348 (March, 2006).
8. Onishi A, Iwamoto M, Akita T, Mikawa S, Takeda K, Awata T, Hanada H, Perry A C: Pig cloning by microinjection of fetal fibroblast nuclei. *Science* (New York, N.Y. 2000, 289 (5482):1188-1190.
9. Polejaeva I A, Chen S H, Vaught T D, Page R L, Mullins J, Ball S, Dai Y, Boone J, Walker S, Ayares D L et al: Cloned pigs produced by nuclear transfer from adult somatic cells. *Nature* 2000, 407(6800):86-90.
10. Kragh P M, Vajta G, Corydon T J, Purup S, Bolund L, Callesen H: Production of transgenic porcine blastocysts by hand-made cloning. *Reprod Fertil Dev* 2004, 16(3):315-318.
11. Kragh P M, Du Y, Corydon T J, Purup S, Bolund L, Vajta G: Efficient in vitro production of porcine blastocysts by handmade cloning with a combined electrical and chemical activation. *Theriogenology* 2005, 64(7):1536-1545.
12. Du Y, Kragh P M, Zhang Y, Li J, Schmidt M, Bogh I B, Zhang X, Purup S, Jorgensen A L, Pedersen A M et al: Piglets born from handmade cloning, an innovative cloning method without micromanipulation. *Theriogenology* 2007, 68(8):1104-1110.
13. Dorer D R, Henikoff S: Expansions of transgene repeats cause heterochromatin formation and gene silencing in Drosophila. *Cell* 1994, 77(7):993-1002.
14. Garrick D, Fiering S, Martin D I, Whitelaw E: Repeat-induced gene silencing in mammals. *Nature genetics* 1998, 18(1):56-59.
15. Ivics Z, Hackett P B, Plasterk R H, Izsvak Z: Molecular reconstruction of Sleeping Beauty, a Tc1-like transposon from fish, and its transposition in human cells. *Cell* 1997, 91(4):501-510.
16. Yant S R, Wu X, Huang Y, Garrison B, Burgess S M, Kay M A: High-resolution genome-wide mapping of transposon integration in mammals. *Mol Cell Biol* 2005, 25(6):2085-2094.
17. Liu G, Geurts A M, Yae K, Srinivasan A R, Fahrenkrug S C, Largaespada D A, Takeda J, Horie K, Olson W K, Hackett P B: Target-site preferences of Sleeping Beauty transposons. *J Mol Biol* 2005, 346(1):161-173.
18. Dupuy A J, Clark K, Carlson C M, Fritz S, Davidson A E, Markley K M, Finley K, Fletcher C F, Ekker S C, Hackett P B et al: Mammalian germ-line transgenesis by transposition. *Proc Nat/Acad Sci USA* 2002, 99(7):4495-4499.
19. Fischer S E, Wienholds E, Plasterk R H: Regulated transposition of a fish transposon in the mouse germ line. *Proc Natl Acad Sci USA* 2001, 98(12):6759-6764.

20. Horie K, Kuroiwa A, Ikawa M, Okabe M, Kondoh G, Matsuda Y, Takeda J: Efficient chromosomal transposition of a Tc1/mariner-like transposon Sleeping Beauty in mice. *Proc Natl Acad Sci USA* 2001, 98(16):9191-9196.

21. Luo G, Ivics Z, Izsvak Z, Bradley A: Chromosomal transposition of a Tc1/mariner-like element in mouse embryonic stem cells. *Proc Natl Acad Sci USA* 1998, 95(18): 10769-10773.

22. Wilber A, Linehan J L, Tian X, Woll P S, Morris J K, Belur L R, McIvor R S, Kaufman D S: Efficient and stable transgene expression in human embryonic stem cells using transposon-mediated gene transfer. *Stem Cells* 2007, 25(11):2919-2927.

23. Mikkelsen J G, Yant S R, Meuse L, Huang Z, Xu H, Kay M A: Helper-Independent Sleeping Beauty transposon-transposase vectors for efficient nonviral gene delivery and persistent gene expression in vivo. *Mol Ther* 2003, 8(4): 654-665.

24. Yant S R, Meuse L, Chiu W, Ivics Z, Izsvak Z, Kay M A: Somatic integration and long-term transgene expression in normal and haemophilic mice using a DNA transposon system. *Nat Genet.* 2000, 25(1):35-41.

25. Collier L S, Carlson C M, Ravimohan S, Dupuy A J, Largaespada D A: Cancer gene discovery in solid tumours using transposon-based somatic mutagenesis in the mouse. *Nature* 2005, 436(7048):272-276.

26. Dupuy A J, Akagi K, Largaespada D A, Copeland N G, Jenkins N A: Mammalian mutagenesis using a highly mobile somatic Sleeping Beauty transposon system. *Nature* 2005, 436(7048):221-226.

27. Clark K J, Carlson D F, Foster L K, Kong B W, Foster D N, Fahrenkrug S C: Enzymatic engineering of the porcine genome with transposons and recombinases. *BMC Biotechnol* 2007, 7:42.

28. Moldt B, Staunstrup N H, Jakobsen M, Yanez-Munoz R J, Mikkelsen J G: Site-directed genomic insertion of lentiviral DNA circles. Submitted for publication.

29. Izsvak Z, Ivics Z, Plasterk R H: Sleeping Beauty, a wide host-range transposon vector for genetic transformation in vertebrates. *J Mol Biol* 2000, 302(1):93-102.

30. Manuelidis L: Heterochromatic features of an 11-megabase transgene in brain cells. *Proceedings of the National Academy of Sciences of the United States of America* 1991, 88(3):1049-1053.

31. Henikoff S: Conspiracy of silence among repeated transgenes. *Bioessays* 1998, 20(7):532-535.

32. Robertson G, Garrick D, Wilson M, Martin D I, Whitelaw E: Age-dependent silencing of globin transgenes in the mouse. *Nucleic acids research* 1996, 24(8):1465-1471.

33. Schroder A R, Shinn P, Chen H, Berry C, Ecker J R, Bushman F: HIV-1 integration in the human genome favors active genes and local hotspots. *Cell* 2002, 110(4):521-529.

34. Wu X, Li Y, Crise B, Burgess S M: Transcription start regions in the human genome are favored targets for MLV integration. *Science* (New York, N.Y. 2003, 300(5626): 1749-1751.

35. Wilson M H, Coates C J, George A L, Jr.: PiggyBac Transposon-mediated Gene Transfer in Human Cells. *Mol Ther* 2007, 15(1):139-145.

36. Ivics Z, Katzer A, Stuwe E E, Fiedler D, Knespel S, Izsvak Z: Targeted Sleeping Beauty transposition in human cells. *Mol Ther* 2007, 15(6):1137-1144.

37. Yant S R, Huang Y, Akache B, Kay M A: Site-directed transposon integration in human cells. *Nucleic Acids Res* 2007, 35(7):e50.

38. Yant S R, Park J, Huang Y, Mikkelsen J G, Kay M A: Mutational analysis of the N-terminal DNA-binding domain of sleeping beauty transposase: critical residues for DNA binding and hyperactivity in mammalian cells. *Mol Cell Biol* 2004, 24(20):9239-9247.

39. Chen Z Y, He C Y, Ehrhardt A, Kay M A: Minicircle DNA vectors devoid of bacterial DNA result in persistent and high-level transgene expression in vivo. *Mol Ther* 2003, 8(3):495-500.

40. Riu E, Chen Z Y, Xu H, He C Y, Kay M A: Histone Modifications are Associated with the Persistence or Silencing of Vector-mediated Transgene Expression In Vivo. *Mol Ther* 2007, 15(7):1348-1355.

41. Chen Z Y, He C Y, Kay M A: Improved production and purification of minicircle DNA vector free of plasmid bacterial sequences and capable of persistent transgene expression in vivo. *Hum Gene Ther* 2005, 16(1):126-131.

The invention claimed is:

1. A genetically modified pig, porcine blastocyst, embryo, fetus, donor cell and/or cell nucleus, whose genome comprises at least one heterologous site-specific recombination site for insertion of at least one transgene and further comprises a transposon tag, wherein said recombination site and transposon tag are inserted in the genome using a recombinant target vector comprising a DNA-transposon based construct, and/or a genetically modified porcine blastocyst, embryo, fetus, donor cell and/or cell nucleus derived from said genetically modified pig, wherein the genome of the derived pig, porcine blastocyst, embryo, fetus, donor cell and/or cell nucleus comprises at east one heterologous site-specific recombination site for insertion of at least one transgene and further comprises a transposon tag.

2. The genetically modified pig, porcine embryo, blastocyst, fetus and/or donor cell, according to claim 1, wherein the pig, porcine embryo, blastocyst, fetus, donor cell and/or cell nucleus is a mini-pig or is obtained from a mini-pig.

3. The genetically modified pig, porcine embryo, blastocyst, fetus and/or donor cell, according to claim 1, wherein said pig, porcine embryo, blastocyst, fetus and/or donor cell, comprises a transposon tagged genome prepared by use of a bi-phase system comprising a recombinant target vector comprising a bicistronic gene cassette comprising (i) at least one site-specific recombination site for site specific integration of at least one transgene after genomic integration of the vector and (ii) an IRES- driven selection gene, and a recombination substrate.

4. The genetically modified pig, porcine embryo, blastocyst, fetus and/or donor cell, according to claim 1, further comprising at least one transgene.

5. The genetically modified pig, porcine embryo, blastocyst, fetus and/or donor cell, according to claim 4, displaying a phenotype associated with disease.

6. A genetically modified pig, porcine embryo, blastocyst, fetus and/or donor cell, according to claim 1, whose genome further comprises at least one gene of interest obtained by recombination into the at least one recombination site for insertion of at least one transgene as defined in claim 1.

7. A recombinant target vector for obtaining a genetically modified pig, porcine blastocyst, embryo, fetus, donor cell and/or cell nucleus according to claim 1, wherein said vector comprises a DNA-transposon-based construct comprising a bicistronic gene cassette comprising (i) at least one site-specific recombination site for site specific integration of at least one transgene after genomic integration of the vector, (ii) an IRES-driven selection gene and (iii) a reporter gene serving as a reporter for continuous gene expression and a selective marker gene, wherein said reporter gene and selective marker gene are disrupted by site specific integration of a transgene.

8. A porcine cell comprising a DNA transposon tagged genome containing at least one heterologous site-specific recombination site for site-specific gene integration of at least one transgene and further comprises a transposon tag as defined in claim 1.

9. A method for producing a porcine cell whose genome comprises at least one heterologous site-specific recombination site for insertion of at least one transgene and further comprises a transposon tag, the method comprising the steps of
   a) providing a porcine cell,
   b) transfecting the cell of a) with a plasmid expressing a transposase and a recombinant vector comprising a DNA transposon-based construct carrying a bicistronic gene cassette comprising (i) a site-specific recombination site and ii) an IRES-driven selection gene, and
   c) selecting DNA transposon tagged cells.

10. A method for obtaining the genetically modified pig, porcine embryo, blastocyst, fetus and/or donor cell according to claim 1 comprising the steps of
    i) providing a donor cell
    ii) genetically modifying the donor cell of i) by inserting into the genome of said donor cell a recombinant target vector comprising a DNA-transposon-based construct comprising a bicistronic gene cassette comprising (i) at least one recombination site for site specific integration of at least one transgene as defined in claim 1 and (ii) an IRES-driven selection gene,
    iii) transferring the modified genome of the donor cell obtained in ii) into a host cell
    iv) obtaining a reconstructed embryo and forming an embryo
    v) culturing said embryo; and
    vi) transferring said cultured embryo to a host pig such that the embryo develops into a genetically modified fetus and then into a pig whose genome comprises at least one heterologous site-specific recombination site for insertion of at least one transgene and further comprises a transposon tag,
    wherein said genetically modified embryo is obtainable by nuclear transfer comprising steps i) to iv) and optionally v),
    wherein said genetically modified blastocyst is obtainable by nuclear transfer comprising steps i) to v) and optionally vi), and
    wherein said genetically modified fetus is obtainable by nuclear transfer comprising steps i) to vi).

11. The genetically modified pig porcine embryo, blastocyst, fetus and/or donor cell according to claim 1 obtainable by nuclear transfer comprising the steps of
    i) establishing at least one oocyte having at least a part of a modified zona pellucida,
    ii) separating the oocyte into at least two parts whereby an oocyte having a nucleus and at least one cytoplast is obtained,
    iii) establishing a donor cell or membrane surrounded cell nucleus with desired genetic properties by genetically modifying the donor cell or membrane surrounded cell nucleus by inserting into the genome of said donor cell or membrane surrounded cell nucleus a recombinant target vector comprising a DNA-transposon-based construct comprising a bicistronic gene cassette comprising (i) at least one recombination site for site specific integration of at least one transgene as defined in claim 1 and (ii) an IRES-driven selection gene,
    iv) fusing said at least one cytoplast with the donor cell or membrane surrounded cell nucleus,
    v) obtaining a reconstructed embryo,
    vi) activating the reconstructed embryo to form an embryo and culturing said embryo; and
    vii) transferring said cultured embryo to a host pig such that the embryo develops into a genetically modified fetus,
    wherein said genetically modified embryo is obtainable by nuclear transfer comprising steps i) to v) and optionally vi),
    wherein said genetically modified blastocyst is obtainable by nuclear transfer comprising steps i) to vi) and optionally vii), and
    wherein said genetically modified fetus is obtainable by nuclear transfer comprising steps i) to vii) and
    wherein the genome of said pig, porcine blastocyst, embryo, fetus, donor cell and/or cell nucleus comprises at least one heterologous site-specific recombination site for insertion of at least one transgene and further comprises a transposon tag.

12. A method for producing a genetically modified pig, porcine embryo, blastocyst, fetus and/or donor cell, comprising at least one heterologous site-specific recombination site comprising:
    i) establishing at least one oocyte,
    ii) separating the oocyte into at least three parts whereby at least one cytoplast is obtained,
    iii) establishing a donor cell or membrane surrounded cell nucleus whose genome comprises heterologous site-specific recombination sites having desired genetic properties by genetically modifying the donor cell or membrane surrounded cell nucleus by inserting into the genome of said donor cell or membrane surrounded cell nucleus a recombinant target vector comprising a DNA-transposon-based construct comprising a bicistronic gene cassette comprising (i) at least one recombination site for site specific integration of at least one transgene as defined in claim 1 and (ii) an IRES-driven selection gene,
    iv) fusing said at least one cytoplast with the donor cell or membrane surrounded cell nucleus,
    v) obtaining a reconstructed embryo,
    vi) activating the reconstructed embryo to form an embryo and culturing said embryo, and
    vii) transferring said cultured embryo to a host mammal such that the embryo develops into a genetically modified fetus,
    wherein said genetically modified embryo is obtainable by nuclear transfer comprising steps i) to v) and optionally vi), wherein said genetically modified blastocyst is obtainable by nuclear transfer comprising steps i) to vi) and optionally vii), and wherein said genetically modified fetus is obtainable by nuclear transfer comprising steps i) to vii), and wherein the pig, porcine embryo, blastocyst, fetus or cell's genome comprises at least one heterologous site-specific recombination site for insertion of at least one transgene and further comprises a transposon tag.

13. A method for producing a genetically modified pig, porcine embryo, blastocyst, fetus and/or donor cell comprising at least one heterologous site-specific recombination site according to claim 1, said method comprising:
  i) establishing at least one oocyte,
  ii) separating the oocyte into at least three parts whereby at least one cytoplast is obtained,
  iii) establishing a donor cell or membrane surrounded cell nucleus whose genome comprises at least one heterologous site-specific recombination site for insertion of at least one transgene and further comprises a transposon tag, wherein the donor cell is established from a genetically modified pig whose genome comprises at least one heterologous site-specific recombination site for insertion of at least one transgene and further comprises a transposon tag,
  iv) providing a transgene and integrating said transgene into the donor cell of iii),
  v) fusing said at least one cytoplast with the donor cell or membrane surrounded cell nucleus,
  vi) obtaining a reconstructed embryo,
  vii) activating the reconstructed embryo to form an embryo;
  viii) culturing said embryo; and
  ix) transferring said cultured embryo to a host pig such that the embryo develops into a genetically modified fetus and then into a pig,
  wherein said genetically modified embryo is obtainable by nuclear transfer comprising steps i) to vi) and optionally vii),
  wherein said genetically modified blastocyst is obtainable by nuclear transfer comprising steps i) to vii) and optionally viii), and
  wherein said genetically modified fetus obtainable by nuclear transfer comprises steps i) to ix), and wherein the pig, porcine embryo, blastocyst, fetus or cell's genome comprises at least one heterologous site-specific recombination site for insertion of at least one transgene and further comprises a transposon tag.

14. The genetically modified pig model, porcine embryo, blastocyst, fetus and/or donor cell according to claim 1 obtainable by nuclear transfer comprising the steps of
  i) establishing at least one oocyte having at least a part of a modified zona pellucida,
  ii) separating the oocyte into at least two parts whereby an oocyte having a nucleus and at least one cytoplast is obtained,
  iii) establishing a donor cell or membrane surrounded cell nucleus whose genome comprises at least one heterologous site-specific recombination site for insertion of at least one transgene and further comprises a transposon tag, wherein the donor cell is established from a genetically modified pig whose genome comprises at least one heterologous site-specific recombination site for insertion of at least one transgene and further comprises a transposon tag,
  iv) providing a transgene and integrating said transgene into the donor cell of iii),
  v) fusing said at least one cytoplast with the donor cell or membrane surrounded cell nucleus,
  vi) obtaining a reconstructed embryo,
  vii) activating the reconstructed embryo to form an embryo and culturing said embryo; and
  viii) transferring said cultured embryo to a host pig such that the embryo develops into a genetically modified fetus and then into a pig whose genome comprises at least one heterologous site-specific recombination site for insertion of at least one transgene and further comprises a transposon tag.

* * * * *

UNITED STATES PATENT AND TRADEMARK OFFICE
CERTIFICATE OF CORRECTION

| | |
|---|---|
| PATENT NO. | : 8,581,021 B2 |
| APPLICATION NO. | : 12/529958 |
| DATED | : November 12, 2013 |
| INVENTOR(S) | : Jacob Giehm Mikkelsen et al. |

It is certified that error appears in the above-identified patent and that said Letters Patent is hereby corrected as shown below:

Title page, Item [54] and in the Specification, Column 1, the title should read as follows:

A PIG WHOSE GENOME COMPRISES A HETEROLOGOUS SITE-SPECIFIC RECOMBINATION SITE AND A TRANSPOSON TAG

Signed and Sealed this
Fourth Day of February, 2014

Michelle K. Lee
*Deputy Director of the United States Patent and Trademark Office*